United States Patent
Ahrens et al.

(10) Patent No.: US 8,114,816 B2
(45) Date of Patent: Feb. 14, 2012

(54) HERBICIDALLY ACTIVE 4-(3-ALKYLSULFINYLBENZOYL)PYRAZOLES

(75) Inventors: Hartmut Ahrens, Egelsbach (DE); Andreas Almsick, Karben (DE); Jan Dittgen, Frankfurt (DE); Simon Dörner, Neu-Anspach (GE); Dieter Feucht, Eschborn (DE); Isolde Häuser-Hahn, Leverkusen (DE); Stefan Lehr, Liederbach (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 122 days.

(21) Appl. No.: 12/472,682

(22) Filed: May 27, 2009

(65) Prior Publication Data

US 2010/0004129 A1 Jan. 7, 2010

(30) Foreign Application Priority Data

May 29, 2008 (EP) .................... 08009758

(51) Int. Cl.
- *A01N 43/56* (2006.01)
- *C07D 231/20* (2006.01)
- *C07C 325/02* (2006.01)
- *A61P 13/00* (2006.01)

(52) U.S. Cl. .............. 504/282; 504/350; 548/369.4; 568/20

(58) Field of Classification Search .............. None
See application file for complete search history.

(56) References Cited

U.S. PATENT DOCUMENTS

| | | | |
|---|---|---|---|
| 4,885,022 | A | 12/1989 | Baba et al. |
| 4,986,845 | A | 1/1991 | Oya et al. |
| 5,013,659 | A | 5/1991 | Bedbrook et al. |
| 6,291,682 | B1 | 9/2001 | Otten et al. |
| 2005/0282709 | A1 | 12/2005 | van Almsick et al. |
| 2008/0305956 | A1 | 12/2008 | Ahrens et al. |

FOREIGN PATENT DOCUMENTS

| | | |
|---|---|---|
| EP | 0142924 | 5/1985 |
| EP | 0193259 | 1/1986 |
| EP | 0221044 | 6/1987 |
| EP | 0242236 | 10/1987 |
| EP | 0242246 | 11/1987 |
| EP | 0257993 | 3/1988 |
| EP | 0309862 | 9/1988 |
| EP | 0464461 | 9/1991 |
| EP | 0 961 774 | 12/1999 |
| JP | 1052759 | 2/1989 |
| WO | 8402919 | 8/1984 |
| WO | 9113972 | 9/1991 |
| WO | 9200377 | 1/1992 |
| WO | 9211376 | 7/1992 |
| WO | 9214827 | 9/1992 |
| WO | 9741106 | 11/1997 |
| WO | 0003993 | 1/2000 |
| WO | 0034270 | 6/2000 |
| WO | 2007069771 | 6/2007 |

OTHER PUBLICATIONS

International Search Report Based on PCT/EP2009/003474 Mailed Jan. 27, 2011.

*Primary Examiner* — Kamal Saeed
(74) *Attorney, Agent, or Firm* — Baker Donelson Bearman, Caldwell & Berkowitz, PC

(57) ABSTRACT

4-(3-Alkylsulfinylbenzoyl)pyrazoles of the formula (I) are described as herbicides.

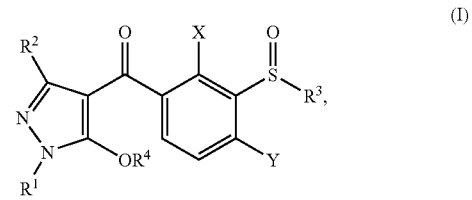

In this formula (I), $R^1$ to $R^4$, X and Y are radicals such as hydrogen, organic radicals such as alkyl, and other radicals such as halogen.

19 Claims, No Drawings

HERBICIDALLY ACTIVE 4-(3-ALKYLSULFINYLBENZOYL)PYRAZOLES

CROSS REFERENCE TO RELATED APPLICATIONS

This application claims priority to European Application No. 08009758.7 filed May 29, 2008, the entire contents of which are incorporated by reference.

BACKGROUND OF THE INVENTION

1. Field of the Invention

The invention relates to the technical field of the herbicides, in particular to that of the herbicides for the selective control of broad-leafed leaves and grass weeds in crops of useful plants.

2. Description of Related Art

It has already been disclosed in various publications that certain 4-benzoylpyrazoles substituted by sulfur-containing radicals in the 3-position of the phenyl ring have herbicidal properties. Thus, EP 0 352 543 and WO 97/41106 mentions benzoylpyrazoles which may be substituted at the phenyl ring inter alia by an alkylsulfinyl radical. WO 00/03993 and WO 2008/151719 disclose inter alia 3-cyclopropyl-4-(3-alkylsulfinyl benzoyl)pyrazoles.

However, the compounds known from these publications frequently do not display a sufficient herbicidal activity. It is therefore an object of the present invention to provide alternative herbicidally active compounds.

SUMMARY OF THE INVENTION

It has now been found that certain 4-benzoylpyrazoles whose phenyl ring carries an alkylsulfinyl radical in the 3-position are especially suitable as herbicides.

The present invention relates to 4-(3-alkylsulfinylbenzoyl) pyrazoles of the formula (I) or their salts in which
$R^1$ is $(C_1-C_4)$-alkyl,
$R^2$ is hydrogen or $(C_1-C_4)$-alkyl,
$R^3$ is $(C_1-C_6)$-alkyl,
$R^4$ is hydrogen, $(C_1-C_6)$-alkylsulfonyl, $(C_1-C_4)$-alkoxy-$(C_1-C_6)$-alkylsulfonyl, or is phenylsulfonyl, thiophenyl-2-sulfonyl, benzoyl, benzoyl-$(C_1-C_6)$-alkyl or benzyl, each of which is substituted by m identical or different radicals from the group consisting of halogen, $(C_1-C_4)$-alkyl and $(C_1-C_4)$-alkoxy,
X is hydrogen, mercapto, nitro, halogen, cyano, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^5$, $OCOR^5$, $OSO_2R^5$, $S(O)_nR^5$, $SO_2OR^5$, $SO_2N(R^5)_2$, $NR^5SO_2R^5$, $NR^5COR^5$, $(C_1-C_6)$-alkyl-$S(O)_nR^5$, $(C_1-C_6)$-alkyl-$OR^5$, $(C_1-C_6)$-alkyl-$OCOR^5$, $(C_1-C_6)$-alkyl-$OSO_2R^5$, $(C_1-C_6)$-alkyl-$SO_2OR^5$, $(C_1-C_6)$-alkyl-$SO_2N(R^5)_2$ or $(C_1-C_6)$-alkyl-$NR^5COR^5$;
Y is fluorine, chlorine, bromine, iodine, nitro or the group $SO_2R^7$,
$R^5$ is hydrogen, $(C_1-C_6)$-alkyl, $(C_2-C_6)$-alkenyl, $(C_2-C_6)$-alkynyl, $(C_3-C_6)$-cycloalkyl, phenyl or phenyl-$(C_1-C_6)$-alkyl, where the six last-mentioned radicals are substituted by s radicals from the group consisting of hydroxy, mercapto, amino, cyano, nitro, thiocyanato, $OR^6$, $SR^6$, $N(R^6)_2$, $NOR^6$, $OCOR^6$, $SCOR^6$, $NR^6COR^6$, $CO_2R^6$, $COSR^6$, $CON(R^6)_2$, $(C_1-C_4)$-alkyliminooxy, $(C_1-C_4)$-alkylcarbonyl, $(C_1-C_4)$-alkoxy-$(C_2-C_6)$-alkoxycarbonyl and $(C_1-C_4)$-alkylsulfonyl;
$R^6$ is hydrogen, $(C_1-C_6)$-alkyl, $(C_2-C_6)$-alkenyl or $(C_2-C_6)$-alkynyl,
$R^7$ is $(C_1-C_4)$-alkyl,
m is 0, 1, 2, 3, 4 or 5,
n is 0, 1 or 2,
s is 0, 1, 2 or 3.

In formula (I) and all formulae given below, alkyl radicals which have more than two carbon atoms may be straight-chain or branched. Alkyl radicals are, for example, methyl, ethyl, n- or i-propyl, n-, i-, t- or 2-butyl, pentyls, hexyls, such as n-hexyl, i-hexyl and 1,3-dimethylbutyl. Halogen is fluorine, chlorine, bromine or iodine.

If a group is polysubstituted by radicals, this is to be understood as meaning that this group is substituted by one or more of the abovementioned radicals which are identical or different.

Owing to the center of chirality of the sulfinyl group, the compounds of the formula (I) are present as enantiomers. In addition, depending on the nature of the substituents and on how they are attached, there may be further stereoisomers, for example in the case of asymmetrically substituted carbon atoms. Stereoisomers, if not already obtained in pure form in the synthesis, can be obtained from the mixtures generated in the course of the preparation using customary separation methods, for example by chromatographic separation methods. Equally, stereoisomers can be prepared selectively using stereoselective reactions and employing optically active starting materials and/or auxiliaries. The invention also relates to all stereoisomers and their mixtures which are embraced by the formula (I), but are not specifically defined.

Preference is given to compounds of the formula (I) in which
$R^1$ is methyl, ethyl, n-propyl or isopropyl,
$R^2$ is hydrogen, methyl, ethyl, n-propyl or isopropyl,
$R^3$ is $(C_1-C_4)$-alkyl,
$R^4$ is hydrogen, $(C_1-C_3)$-alkylsulfonyl, $(C_1-C_2)$-alkoxy-$(C_1-C_4)$-alkylsulfonyl, or is phenylsulfonyl, thiophenyl-2-sulfonyl, benzoyl, benzoyl-$(C_1-C_6)$-alkyl or benzyl, each of which is substituted by m methyl groups,
X is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonyl methyl, methylsulfonylethoxymethyl, methoxyethylsulfonyl methyl, methylsulfonylethylsulfonylmethyl,
Y is fluorine, chlorine, bromine, iodine or the group $SO_2R^7$,
$R^7$ is methyl, ethyl, n-propyl or isopropyl,
m is 0, 1, 2 or 3.

Particular preference is given to compounds of the formula (I) in which
$R^1$ is methyl or ethyl,
$R^2$ is hydrogen, methyl or ethyl,
$R^3$ is methyl, ethyl, n-propyl or isopropyl,
$R^4$ is hydrogen, X is nitro, halogen, ($C_1$-$C_4$)-alkyl, trifluoromethyl, ($C_1$-$C_4$)-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonyl methyl, methylsulfonylethoxymethyl, methoxyethylsulfonyl methyl, methylsulfonylethylsulfonylmethyl, Y is fluorine, chlorine, bromine, iodine or the group $SO_2R^7$, $R^7$ is methyl or ethyl.

DETAILED DESCRIPTION OF A PREFERRED EMBODIMENT

Unless otherwise defined, the substituents and symbols in all the formulae mentioned hereinbelow have the same meaning as described in formula (I).

Compounds according to the invention in which $R^4$ is hydrogen can be prepared, for example, by the process shown in Scheme 1 and known from WO2005/122768 by reacting a benzoic acid of the formula (II) with a pyrazole of the formula (III) in the presence of a condensing agent such as N-(3-dimethylaminopropyl)-N'-ethylcarbodiimide hydrochloride, followed by cyanide-catalyzed rearrangement.

Scheme 1

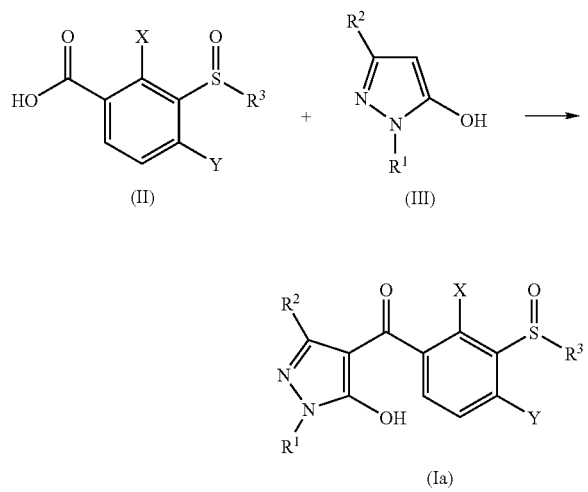

Compounds of the formula (I) can be prepared, for example, by the process shown in Scheme 2 and described in WO2005/122768 by reacting a compound of the formula (Ia) with compounds of the formula (IV) in which E is a nucleophilic leaving group.

Scheme 2

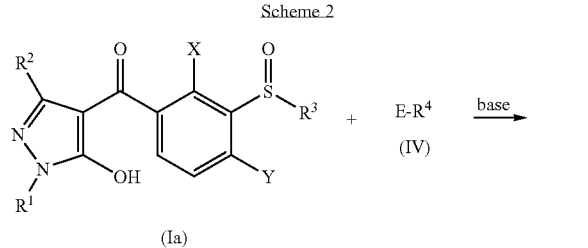

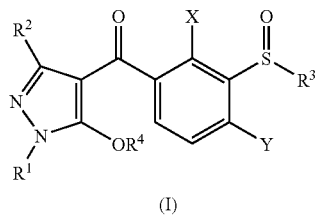

Compounds according to the invention in which $R^4$ is hydrogen can also be prepared, for example, by the process shown in Scheme 3 by nucleophilic aromatic substitution from compounds of the formula (V) in which $L^2$ is, for example, a fluorine or chlorine atom using a thiolate (VI) in which M is a metal cation, followed by oxidation.

Scheme 3

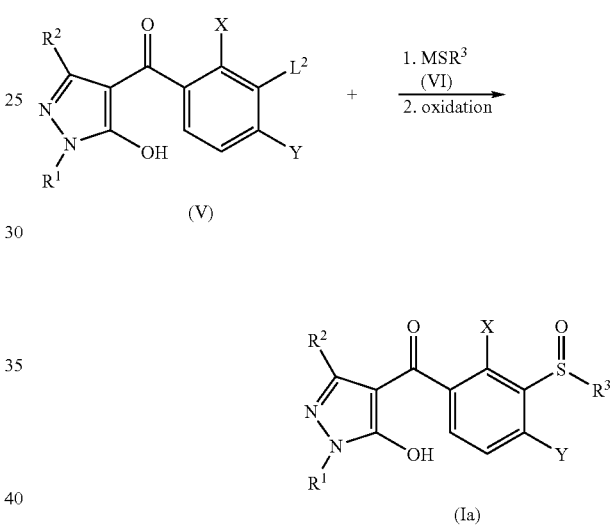

Compounds of the formula (II) can be prepared, for example, by the process shown in Scheme 4 from benzoic acids of the formula (VII) by introducing the substituent X, followed by nucleophilic aromatic substitution and then oxidation. Suitable reactions for introducing the substituent X are known, for example, from J. Chem. Soc. Perkin Trans. 1 1995, p. 1265 ff, J. Heterocyclic Chem. 1999, 36, p. 1453 ff., Angew. Chem. 2005, 117, 380-398, J. Org. Chem. 2003, 68, 2030-2033 and J. Org. Chem. 1994, 59, 4042-4044.

Scheme 4

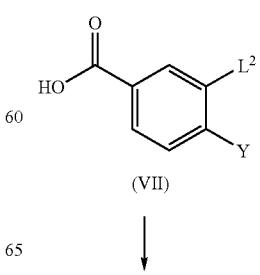

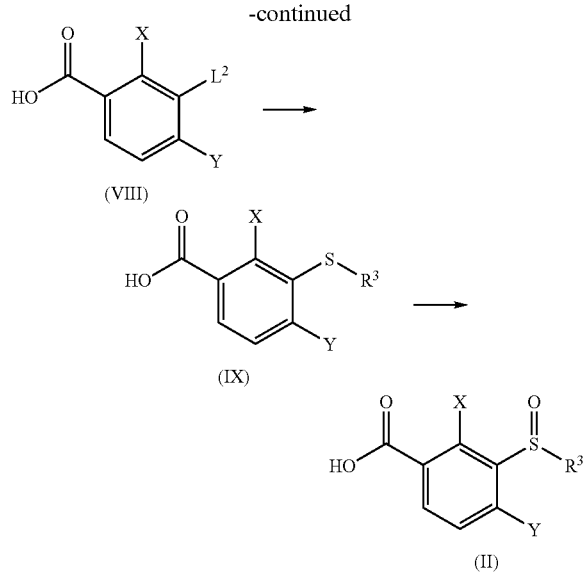

Compounds of the formula (II) are novel and also form part of the subject matter of the present invention.

Collections of compounds of the formula (I) and/or their salts which can be synthesized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning a procedure as described for example by D. Tiebes in Combinatorial Chemistry—Synthesis, Analysis, Screening (Editor Gunther Jung), Wiley 1999, on pages 1 to 34.

A series of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Gunther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation in accordance with the processes described herein generates compounds of the formula (I) and their salts in the form of substance collections, which are referred to as libraries. The present invention also relates to libraries which comprise at least two compounds of the formula (I) and their salts.

The compounds of the formula (I) according to the invention (and/or their salts), hereinbelow together referred to as "compounds according to the invention", have an outstanding herbicidal activity against a broad spectrum of economically important monocotyledonous and dicotyledonous annual harmful plants. The active substances also act efficiently on perennial harmful plants which produce shoots from rhizomes, rootstocks or other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranun-*

*culus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active substances are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active substances can also be employed for controlling harmful plants in crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

It is preferred to use the compounds according to the invention or their salts in economically important transgenic crops of useful plants and ornamentals, for example of cereals such as wheat, barley, rye, oats, sorghum and millet, rice, cassaya and maize or else crops of sugar beet, cotton, soybean, oil seed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product. To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active substances according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be employed in the customary preparations in the form of wettable powders, emulsifiable concentrates, sprayable solutions, dusts or granules. The invention therefore also relates to herbicidal and plant-growth-regulating compositions which comprise the compounds according to the invention.

The compounds according to the invention can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Wettable powders are preparations which are uniformly dispersible in water and which, besides the active substance, also comprise ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Active substances which can be employed in combination with the compounds according to the invention in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers. In this context, one and in some cases also several use forms are mentioned by way of example:

acetochlor, acibenzolar, acibenzolar-5-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifopbutyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulf-allate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryne, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

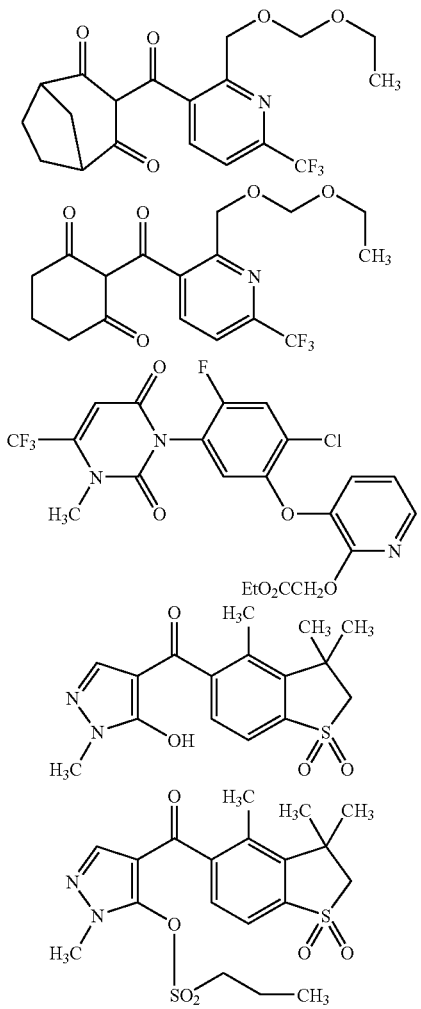

For use, the formulations, which are present in commercially available form, if appropriate, are diluted in the customary manner, for example using water in the case of wettable powders, emulsifiable concentrates, dispersions and water-dispersible granules. Preparations in the form of dusts, soil granules, granules for broadcasting, and sprayable solutions, are usually not diluted further with further inert substances prior to use.

The application rate required of the compounds of the formula (I) varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

The examples which follow are intended to illustrate the invention.

A. CHEMICAL EXAMPLES

1. Preparation of 4-(4-chloro-3-ethylsulfinyl-2-methyl benzoyl)-5-hydroxy-1,3-dimethylpyrazole (No. 3-238 of Table 3)

Step 1: Synthesis of methyl 4-chloro-3-(dimethylaminothiocarbonyloxy)-2-methylbenzoate Under an atmosphere of nitrogen, 12.3 g (109.7 mmol) of 1,4-diazabicyclo[2.2.2]octane and then 13.6 g (109.7 mmol) of dimethylaminothiocarbonyl chloride were added to 11.0 g (54.8 mmol) of methyl 4-chloro-3-hydroxy-2-methylbenzoate in 200 ml of N,N-dimethylformamide. The mixture was stirred at room temperature (RT) for 16 h and, for work-up, poured on ice-water. The product precipitated out and was removed by filtration. The residue was washed with 1M HCl. This gave 14.7 g of clean product.

Step 2: Synthesis of methyl 4-chloro-3-(dimethylaminocarbonylthio)-2-methylbenzoate Under an atmosphere of nitrogen, 12.1 g (42.0 mmol) of methyl 4-chloro-3-(dimethylaminothiocarbonyloxy)-2-methylbenzoate in 30 ml of 1,3-dimethoxybenzene were heated at 220° C. for 6 h. For work-up, the reaction mixture was cooled and concentrated under reduced pressure. After chromatographic purification of the residue, 5.2 g of clean product were isolated.

Step 3: Synthesis of 4-chloro-3-mercapto-2-methylbenzoic acid 6.61 g (85% by weight pure, 100.1 mmol) of potassium hydroxide were added to 4.80 g (16.7 mmol) of methyl 4-chloro-3-(dimethylaminocarbonylthio)-2-methylbenzoate in 150 ml of methanol, and the mixture was stirred under reflux for two days. The reaction mixture was freed from the solvent, water was added to the residue, the mixture was acidified with 1M HCl and the solid was removed by filtration. This gave 3.2 g of clean product.

Step 4: Synthesis of 4-chloro-3-ethylthio-2-methylbenzoic acid 3.71 g (11.3 mmol) of cesium carbonate were added to 1.10 g (5.42 mmol) of 4-chloro-3-mercapto-2-methylbenzoic acid in 20 ml of acetonitrile. The reaction mixture was stirred at RT for 10 min, and 1.02 g (6.51 mmol) of iodoethane were then slowly added dropwise. The reaction mixture was then stirred at RT for 16 h. The solvent was then removed, and a mixture of 20 ml of methanol and 2 ml of 20% strength aqueous sodium hydroxide solution was then added to the reaction mixture. For the hydrolysis of the ethyl ester formed, the mixture was stirred at RT for 16 h and then freed from the solvents. The residue was taken up in water and acidified with diluted HCl, and the mixture was stirred at RT for 10 min and then filtered. The residue was washed with water and sucked dry. 1.15 g of clean product were isolated.

Step 5: Synthesis of 4-chloro-3-ethylsulfinyl-2-methylbenzoic acid (No. 4-238)

1.15 g (4.98 mmol) of 4-chloro-3-ethylthio-2-methylbenzoic acid in 10 ml of glacial acetic acid were heated to a temperature of 50° C.-60° C. At this temperature, 484 mg (35% strength, 4.98 mmol) of an aqueous hydrogen peroxide solution were added dropwise. The mixture was stirred at this temperature for 5 h. The reaction mixture was cooled, washed with an aqueous saturated sodium bisulfite solution and, after analytical proof of absence of peroxides, freed from the solvents. Water was added to the residue, and the mixture was acidified with 6M HCl. The mixture was extracted with ethyl acetate, and the combined organic phases were dried, filtered and, under reduced pressure, freed from the solvent. 1.24 g of the product (purify about 95% by weight) were isolated.

Step 6: Synthesis of 4-(4-chloro-3-ethylsulfinyl-2-methyl benzoyl)-5-hydroxy-1,3-dimethylpyrazole 128 mg (1.14 mmol) of 5-hydroxy-1,3-dimethylpyrazole were added to 270 mg (purity 95% by weight; 1.04 mmol) of 4-chloro-3-ethylsulfinyl-2-methylbenzoic acid in 20 ml of dichloromethane ($CH_2Cl_2$). 239 mg (1.24 mmol) of 1-(3'-dimethylaminopropyl)-3-ethylcarbodiimide hydrochloride were added, and the mixture was stirred at RT for 16 h. For work-up, 3 ml of 1M HCl were added, and the organic phase was freed from the solvent. 210 mg (2.07 mmol) of triethylamine, 10 drops of acetone cyanohydrin and a spatula tip of potassium cyanide were added to the residue in 20 ml of acetonitrile. The reaction mixture was stirred at RT for 16 h and then freed from the solvent. The residue was stirred at RT with 25 ml of a mixture of aqueous saturated sodium bicarbonate solution and diethyl ether for 10 min. The phases were separated, and the aqueous phase was acidified with dilute HCl and then extracted with $CH_2Cl_2$. The organic phase was freed from the solvent and the residue was then purified chromatographically. This gave 100 mg of clean product.

2. Preparation of 5-hydroxy-1-methyl-4-(2-methyl-3-methylsulfinyl-4-methylsulfonylbenzoyl)pyrazole (No. 1-9 of Table 1)

Step 1: Synthesis of 2-methyl-3-methylsulfinyl-4-methylsulfonylbenzoic acid (No. 4-9)

900 mg (3.45 mmol) of 2-methyl-4-methylsulfonyl-3-methylthiobenzoic acid in 10 ml of glacial acetic acid were heated to a temperature of 50° C.-60° C. At this temperature, 336 mg (35% strength, 3.45 mmol) of an aqueous hydrogen peroxide solution were added dropwise. The mixture was stirred at 60° C. for 5 h. The reaction mixture was cooled, washed with an aqueous 10% strength sodium bisulfite solution and, after analytical proof of absence of peroxides, freed from the solvents. Water was added to the residue, and the aqueous phase was extracted three times with ethyl acetate. The combined organic phases were dried, filtered and, under reduced pressure, freed from the solvent. 950 mg of the clean product were isolated.

Step 2: Synthesis of 5-hydroxy-1-methyl-4-(2-methyl-3-methylsulfinyl-4-methylsulfonylbenzoyl)pyrazole 90 mg (0.91 mmol) of 5-hydroxy-1-methylpyrazole and a spatula tip of 4-(dimethylamino)pyridine were added to 230 mg (0.83 mmol) of 2-methyl-3-methylsulfinyl-4-methylsulfonylbenzoic acid in 20 ml of $CH_2Cl_2$. 191 mg (0.99 mmol) of 1-(3'-dimethylaminopropyl)-3-ethylcarbodiimide hydrochloride were added, and the mixture was stirred at RT for 90 min. 3 ml of 1M HCl were then added, and the organic phase was freed from the solvent. 168 mg (1.66 mmol) of triethylamine, 10 drops of acetone cyanohydrin and a spatula tip of potassium cyanide were added to the residue in 15 ml of acetonitrile. The reaction mixture was stirred at RT for 16 h and then freed from the solvent. 15 ml of $CH_2Cl_2$ were added to the residue, and 2 ml of 1M HCl were then added. After phase separation, the organic phase was freed from the solvent. The residue was stirred with 25 ml of a mixture of aqueous saturated sodium bicarbonate solution and diethyl ether at RT for 10 min. The phases were separated, and the aqueous phase was acidified with dilute HCl and then extracted three times with $CH_2Cl_2$. The combined organic phases were freed from the solvent. This gave 171 mg of clean product.

The examples listed in the tables hereinbelow were prepared analogously to abovementioned methods or are obtainable analogously to above-mentioned methods. These compounds are very particularly preferred.

TABLE 1

Compounds of the formula (I) according to the invention in which $R^1$ is methyl, $R^2$ and $R^4$ are each hydrogen.

| No. | X | $R^3$ | Y | Physical data: $^1$H—NMR: δ [$CDCl_3$] |
|---|---|---|---|---|
| 1-1 | Cl | Me | $SO_2Me$ | |
| 1-2 | Cl | Et | $SO_2Me$ | 8.23 (d, 1 H), 7.66 (d, 1 H), 7.32 (s, 1 H), 3.92 (m, 1 H), 3.73 (s, 3 H), 3.45 (s, 3 H), 3.28 (m, 1 H), 1.53 (t, 3 H) |
| 1-3 | Cl | n-Pr | $SO_2Me$ | |
| 1-4 | Cl | i-Pr | $SO_2Me$ | |
| 1-5 | Br | Me | $SO_2Me$ | |
| 1-6 | Br | Et | $SO_2Me$ | |
| 1-7 | Br | n-Pr | $SO_2Me$ | |
| 1-8 | Br | i-Pr | $SO_2Me$ | |
| 1-9 | Me | Me | $SO_2Me$ | 8.08 (d, 1 H), 7.62 (d, 1 H), 7.27 (s, 1 H), 3.72 (s, 3 H), 3.38 (s, 3 H), 3.18 (s, 3 H), 2.87 (s, 3 H) |
| 1-10 | Me | Et | $SO_2Me$ | 8.08 (d, 1 H), 7.61 (d, 1 H), 7.27 (s, 1 H), 3.72 (s, 3 H), 3.52 (m, 1 H), 3.38 (s, 3 H), 3.28 (m, 1 H), 2.82 (s, 3 H), 1.52 (t, 3 H) |
| 1-11 | Me | n-Pr | $SO_2Me$ | |
| 1-12 | Me | i-Pr | $SO_2Me$ | |
| 1-13 | Et | Me | $SO_2Me$ | |
| 1-14 | Et | Et | $SO_2Me$ | |
| 1-15 | Et | n-Pr | $SO_2Me$ | |
| 1-16 | Et | i-Pr | $SO_2Me$ | |
| 1-17 | $CF_3$ | Me | $SO_2Me$ | |
| 1-18 | $CF_3$ | Et | $SO_2Me$ | |
| 1-19 | $CF_3$ | n-Pr | $SO_2Me$ | |
| 1-20 | $CF_3$ | i-Pr | $SO_2Me$ | |
| 1-21 | OMe | Me | $SO_2Me$ | |
| 1-22 | OMe | Et | $SO_2Me$ | |
| 1-23 | OMe | n-Pr | $SO_2Me$ | |
| 1-24 | OMe | i-Pr | $SO_2Me$ | |
| 1-25 | OEt | Me | $SO_2Me$ | |
| 1-26 | OEt | Et | $SO_2Me$ | |
| 1-27 | OEt | n-Pr | $SO_2Me$ | |
| 1-28 | OEt | i-Pr | $SO_2Me$ | |
| 1-29 | $NO_2$ | Me | $SO_2Me$ | |
| 1-30 | $NO_2$ | Et | $SO_2Me$ | |
| 1-31 | $NO_2$ | n-Pr | $SO_2Me$ | |
| 1-32 | $NO_2$ | i-Pr | $SO_2Me$ | |
| 1-33 | $SO_2Me$ | Me | $SO_2Me$ | |
| 1-34 | $SO_2Me$ | Et | $SO_2Me$ | |
| 1-35 | $SO_2Me$ | n-Pr | $SO_2Me$ | |
| 1-36 | $SO_2Me$ | i-Pr | $SO_2Me$ | |
| 1-37 | $CH_2OMe$ | Me | $SO_2Me$ | |
| 1-38 | $CH_2OMe$ | Et | $SO_2Me$ | |
| 1-39 | $CH_2OMe$ | n-Pr | $SO_2Me$ | |
| 1-40 | $CH_2OMe$ | i-Pr | $SO_2Me$ | |
| 1-41 | $CH_2SO_2Me$ | Me | $SO_2Me$ | |

TABLE 1-continued

Compounds of the formula (I) according to the invention in which $R^1$ is methyl, $R^2$ and $R^4$ are each hydrogen.

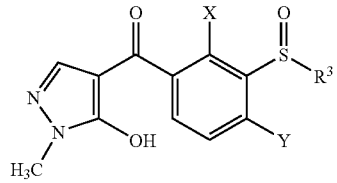

| No. | X | $R^3$ | Y | Physical data: $^1H$—NMR: δ [CDCl$_3$] |
|---|---|---|---|---|
| 1-42 | CH$_2$SO$_2$Me | Et | SO$_2$Me | |
| 1-43 | CH$_2$SO$_2$Me | n-Pr | SO$_2$Me | |
| 1-44 | CH$_2$SO$_2$Me | i-Pr | SO$_2$Me | |
| 1-45 | CH$_2$OCH$_2$CH$_2$OMe | Me | SO$_2$Me | 8.21 (d, 1 H), 7.67 (d, 1 H), 7.37 (s, 1 H), 5.57-5.32 (br. signal, 1 H), 5.00 (d, 1 H), 3.72 (s, 3 H), 3.63-3.58 (m, 1 H), 3.56-3.50 (m, 1 H), 3.42-3.25 (m, 2 H), 3.37 (s, 3 H), 3.32 (s, 3 H), 3.23 (s, 3 H) |
| 1-46 | CH$_2$OCH$_2$CH$_2$OMe | Et | SO$_2$Me | |
| 1-47 | CH$_2$OCH$_2$CH$_2$OMe | n-Pr | SO$_2$Me | |
| 1-48 | CH$_2$OCH$_2$CH$_2$OMe | i-Pr | SO$_2$Me | |
| 1-49 | CH$_2$OCH$_2$CH$_2$OEt | Me | SO$_2$Me | |
| 1-50 | CH$_2$OCH$_2$CH$_2$OEt | Et | SO$_2$Me | |
| 1-51 | CH$_2$OCH$_2$CH$_2$OEt | n-Pr | SO$_2$Me | |
| 1-52 | CH$_2$OCH$_2$CH$_2$OEt | i-Pr | SO$_2$Me | |
| 1-53 | CH$_2$OCH$_2$CH$_2$CH$_2$OMe | Me | SO$_2$Me | |
| 1-54 | CH$_2$OCH$_2$CH$_2$CH$_2$OMe | Et | SO$_2$Me | |
| 1-55 | CH$_2$OCH$_2$CH$_2$CH$_2$OMe | n-Pr | SO$_2$Me | |
| 1-56 | CH$_2$OCH$_2$CH$_2$CH$_2$OMe | i-Pr | SO$_2$Me | |
| 1-57 | CH$_2$OCH$_2$OMe | Me | SO$_2$Me | |
| 1-58 | CH$_2$OCH$_2$OMe | Et | SO$_2$Me | |
| 1-59 | CH$_2$OCH$_2$OMe | n-Pr | SO$_2$Me | |
| 1-60 | CH$_2$OCH$_2$OMe | i-Pr | SO$_2$Me | |
| 1-61 | CH$_2$OCH$_2$OEt | Me | SO$_2$Me | |
| 1-62 | CH$_2$OCH$_2$OEt | Et | SO$_2$Me | |
| 1-63 | CH$_2$OCH$_2$OEt | n-Pr | SO$_2$Me | |
| 1-64 | CH$_2$OCH$_2$OEt | i-Pr | SO$_2$Me | |
| 1-65 | CH$_2$OCH$_2$CH$_2$SO$_2$Me | Me | SO$_2$Me | |
| 1-66 | CH$_2$OCH$_2$CH$_2$SO$_2$Me | Et | SO$_2$Me | |
| 1-67 | CH$_2$OCH$_2$CH$_2$SO$_2$Me | n-Pr | SO$_2$Me | |
| 1-68 | CH$_2$OCH$_2$CH$_2$SO$_2$Me | i-Pr | SO$_2$Me | |
| 1-69 | CH$_2$SO$_2$CH$_2$CH$_2$OMe | Me | SO$_2$Me | |
| 1-70 | CH$_2$SO$_2$CH$_2$CH$_2$OMe | Et | SO$_2$Me | |
| 1-71 | CH$_2$SO$_2$CH$_2$CH$_2$OMe | n-Pr | SO$_2$Me | |
| 1-72 | CH$_2$SO$_2$CH$_2$CH$_2$OMe | i-Pr | SO$_2$Me | |
| 1-73 | CH$_2$SO$_2$CH$_2$CH$_2$SO$_2$Me | Me | SO$_2$Me | |
| 1-74 | CH$_2$SO$_2$CH$_2$CH$_2$SO$_2$Me | Et | SO$_2$Me | |
| 1-75 | CH$_2$SO$_2$CH$_2$CH$_2$SO$_2$Me | n-Pr | SO$_2$Me | |
| 1-76 | CH$_2$SO$_2$CH$_2$CH$_2$SO$_2$Me | i-Pr | SO$_2$Me | |
| 1-77 | Cl | Me | SO$_2$Et | |
| 1-78 | Cl | Et | SO$_2$Et | |
| 1-79 | Cl | n-Pr | SO$_2$Et | |
| 1-80 | Cl | i-Pr | SO$_2$Et | |
| 1-81 | Br | Me | SO$_2$Et | |
| 1-82 | Br | Et | SO$_2$Et | |
| 1-83 | Br | n-Pr | SO$_2$Et | |
| 1-84 | Br | i-Pr | SO$_2$Et | |
| 1-85 | Me | Me | SO$_2$Et | |
| 1-86 | Me | Et | SO$_2$Et | |
| 1-87 | Me | n-Pr | SO$_2$Et | |
| 1-88 | Me | i-Pr | SO$_2$Et | |
| 1-89 | Et | Me | SO$_2$Et | |
| 1-90 | Et | Et | SO$_2$Et | |
| 1-91 | Et | n-Pr | SO$_2$Et | |
| 1-92 | Et | i-Pr | SO$_2$Et | |
| 1-93 | CF$_3$ | Me | SO$_2$Et | |
| 1-94 | CF$_3$ | Et | SO$_2$Et | |
| 1-95 | CF$_3$ | n-Pr | SO$_2$Et | |
| 1-96 | CF$_3$ | i-Pr | SO$_2$Et | |
| 1-97 | OMe | Me | SO$_2$Et | |
| 1-98 | OMe | Et | SO$_2$Et | |
| 1-99 | OMe | n-Pr | SO$_2$Et | |
| 1-100 | OMe | i-Pr | SO$_2$Et | |

TABLE 1-continued

Compounds of the formula (I) according to the invention in which $R^1$ is methyl, $R^2$ and $R^4$ are each hydrogen.

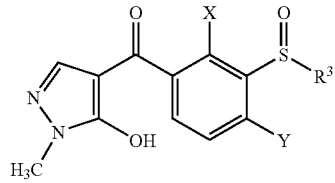

| No. | X | $R^3$ | Y | Physical data: $^1H$—NMR: δ [CDCl$_3$] |
|---|---|---|---|---|
| 1-101 | OEt | Me | SO$_2$Et | |
| 1-102 | OEt | Et | SO$_2$Et | |
| 1-103 | OEt | n-Pr | SO$_2$Et | |
| 1-104 | OEt | i-Pr | SO$_2$Et | |
| 1-105 | NO$_2$ | Me | SO$_2$Et | |
| 1-106 | NO$_2$ | Et | SO$_2$Et | |
| 1-107 | NO$_2$ | n-Pr | SO$_2$Et | |
| 1-108 | NO$_2$ | i-Pr | SO$_2$Et | |
| 1-109 | SO$_2$Me | Me | SO$_2$Et | |
| 1-110 | SO$_2$Me | Et | SO$_2$Et | |
| 1-111 | SO$_2$Me | n-Pr | SO$_2$Et | |
| 1-112 | SO$_2$Me | i-Pr | SO$_2$Et | |
| 1-113 | CH$_2$OMe | Me | SO$_2$Et | |
| 1-114 | CH$_2$OMe | Et | SO$_2$Et | |
| 1-115 | CH$_2$OMe | n-Pr | SO$_2$Et | |
| 1-116 | CH$_2$OMe | i-Pr | SO$_2$Et | |
| 1-117 | CH$_2$SO$_2$Me | Me | SO$_2$Et | |
| 1-118 | CH$_2$SO$_2$Me | Et | SO$_2$Et | |
| 1-119 | CH$_2$SO$_2$Me | n-Pr | SO$_2$Et | |
| 1-120 | CH$_2$SO$_2$Me | i-Pr | SO$_2$Et | |
| 1-121 | CH$_2$OCH$_2$CH$_2$OMe | Me | SO$_2$Et | |
| 1-122 | CH$_2$OCH$_2$CH$_2$OMe | Et | SO$_2$Et | |
| 1-123 | CH$_2$OCH$_2$CH$_2$OMe | n-Pr | SO$_2$Et | |
| 1-124 | CH$_2$OCH$_2$CH$_2$OMe | i-Pr | SO$_2$Et | |
| 1-125 | CH$_2$OCH$_2$CH$_2$OEt | Me | SO$_2$Et | |
| 1-126 | CH$_2$OCH$_2$CH$_2$OEt | Et | SO$_2$Et | |
| 1-127 | CH$_2$OCH$_2$CH$_2$OEt | n-Pr | SO$_2$Et | |
| 1-128 | CH$_2$OCH$_2$CH$_2$OEt | i-Pr | SO$_2$Et | |
| 1-129 | CH$_2$OCH$_2$CH$_2$CH$_2$OMe | Me | SO$_2$Et | |
| 1-130 | CH$_2$OCH$_2$CH$_2$CH$_2$OMe | Et | SO$_2$Et | |
| 1-131 | CH$_2$OCH$_2$CH$_2$CH$_2$OMe | n-Pr | SO$_2$Et | |
| 1-132 | CH$_2$OCH$_2$CH$_2$CH$_2$OMe | i-Pr | SO$_2$Et | |
| 1-133 | CH$_2$OCH$_2$OMe | Me | SO$_2$Et | |
| 1-134 | CH$_2$OCH$_2$OMe | Et | SO$_2$Et | |
| 1-135 | CH$_2$OCH$_2$OMe | n-Pr | SO$_2$Et | |
| 1-136 | CH$_2$OCH$_2$OMe | i-Pr | SO$_2$Et | |
| 1-137 | CH$_2$OCH$_2$OEt | Me | SO$_2$Et | |
| 1-138 | CH$_2$OCH$_2$OEt | Et | SO$_2$Et | |
| 1-139 | CH$_2$OCH$_2$OEt | n-Pr | SO$_2$Et | |
| 1-140 | CH$_2$OCH$_2$OEt | i-Pr | SO$_2$Et | |
| 1-141 | CH$_2$OCH$_2$CH$_2$SO$_2$Me | Me | SO$_2$Et | |
| 1-142 | CH$_2$OCH$_2$CH$_2$SO$_2$Me | Et | SO$_2$Et | |
| 1-143 | CH$_2$OCH$_2$CH$_2$SO$_2$Me | n-Pr | SO$_2$Et | |
| 1-144 | CH$_2$OCH$_2$CH$_2$SO$_2$Me | i-Pr | SO$_2$Et | |
| 1-145 | CH$_2$SO$_2$CH$_2$CH$_2$OMe | Me | SO$_2$Et | |
| 1-146 | CH$_2$SO$_2$CH$_2$CH$_2$OMe | Et | SO$_2$Et | |
| 1-147 | CH$_2$SO$_2$CH$_2$CH$_2$OMe | n-Pr | SO$_2$Et | |
| 1-148 | CH$_2$SO$_2$CH$_2$CH$_2$OMe | i-Pr | SO$_2$Et | |
| 1-149 | CH$_2$SO$_2$CH$_2$CH$_2$SO$_2$Me | Me | SO$_2$Et | |
| 1-150 | CH$_2$SO$_2$CH$_2$CH$_2$SO$_2$Me | Et | SO$_2$Et | |
| 1-151 | CH$_2$SO$_2$CH$_2$CH$_2$SO$_2$Me | n-Pr | SO$_2$Et | |
| 1-152 | CH$_2$SO$_2$CH$_2$CH$_2$SO$_2$Me | i-Pr | SO$_2$Et | |
| 1-153 | Cl | Me | F | |
| 1-154 | Cl | Et | F | |
| 1-155 | Cl | n-Pr | F | |
| 1-156 | Cl | i-Pr | F | |
| 1-157 | Br | Me | F | |
| 1-158 | Br | Et | F | |
| 1-159 | Br | n-Pr | F | |
| 1-160 | Br | i-Pr | F | |
| 1-161 | Me | Me | F | |
| 1-162 | Me | Et | F | |
| 1-163 | Me | n-Pr | F | |
| 1-164 | Me | i-Pr | F | |

TABLE 1-continued

Compounds of the formula (I) according to the invention in which R¹ is methyl, R² and R⁴ are each hydrogen.

| No. | X | R³ | Y | Physical data: $^1$H—NMR: δ [CDCl$_3$] |
|---|---|---|---|---|
| 1-165 | Et | Me | F | |
| 1-166 | Et | Et | F | |
| 1-167 | Et | n-Pr | F | |
| 1-168 | Et | i-Pr | F | |
| 1-169 | CF$_3$ | Me | F | |
| 1-170 | CF$_3$ | Et | F | |
| 1-171 | CF$_3$ | n-Pr | F | |
| 1-172 | CF$_3$ | i-Pr | F | |
| 1-173 | OMe | Me | F | |
| 1-174 | OMe | Et | F | |
| 1-175 | OMe | n-Pr | F | |
| 1-176 | OMe | i-Pr | F | |
| 1-177 | OEt | Me | F | |
| 1-178 | OEt | Et | F | |
| 1-179 | OEt | n-Pr | F | |
| 1-180 | OEt | i-Pr | F | |
| 1-181 | NO$_2$ | Me | F | |
| 1-182 | NO$_2$ | Et | F | |
| 1-183 | NO$_2$ | n-Pr | F | |
| 1-184 | NO$_2$ | i-Pr | F | |
| 1-185 | SO$_2$Me | Me | F | |
| 1-186 | SO$_2$Me | Et | F | |
| 1-187 | SO$_2$Me | n-Pr | F | |
| 1-188 | SO$_2$Me | i-Pr | F | |
| 1-189 | CH$_2$OMe | Me | F | |
| 1-190 | CH$_2$OMe | Et | F | |
| 1-191 | CH$_2$OMe | n-Pr | F | |
| 1-192 | CH$_2$OMe | i-Pr | F | |
| 1-193 | CH$_2$SO$_2$Me | Me | F | |
| 1-194 | CH$_2$SO$_2$Me | Et | F | |
| 1-195 | CH$_2$SO$_2$Me | n-Pr | F | |
| 1-196 | CH$_2$SO$_2$Me | i-Pr | F | |
| 1-197 | CH$_2$OCH$_2$CH$_2$OMe | Me | F | |
| 1-198 | CH$_2$OCH$_2$CH$_2$OMe | Et | F | |
| 1-199 | CH$_2$OCH$_2$CH$_2$OMe | n-Pr | F | |
| 1-200 | CH$_2$OCH$_2$CH$_2$OMe | i-Pr | F | |
| 1-201 | CH$_2$OCH$_2$CH$_2$OEt | Me | F | |
| 1-202 | CH$_2$OCH$_2$CH$_2$OEt | Et | F | |
| 1-203 | CH$_2$OCH$_2$CH$_2$OEt | n-Pr | F | |
| 1-204 | CH$_2$OCH$_2$CH$_2$OEt | i-Pr | F | |
| 1-205 | CH$_2$OCH$_2$CH$_2$CH$_2$OMe | Me | F | |
| 1-206 | CH$_2$OCH$_2$CH$_2$CH$_2$OMe | Et | F | |
| 1-207 | CH$_2$OCH$_2$CH$_2$CH$_2$OMe | n-Pr | F | |
| 1-208 | CH$_2$OCH$_2$CH$_2$CH$_2$OMe | i-Pr | F | |
| 1-209 | CH$_2$OCH$_2$OMe | Me | F | |
| 1-210 | CH$_2$OCH$_2$OMe | Et | F | |
| 1-211 | CH$_2$OCH$_2$OMe | n-Pr | F | |
| 1-212 | CH$_2$OCH$_2$OMe | i-Pr | F | |
| 1-213 | CH$_2$OCH$_2$OEt | Me | F | |
| 1-214 | CH$_2$OCH$_2$OEt | Et | F | |
| 1-215 | CH$_2$OCH$_2$OEt | n-Pr | F | |
| 1-216 | CH$_2$OCH$_2$OEt | i-Pr | F | |
| 1-217 | CH$_2$OCH$_2$CH$_2$SO$_2$Me | Me | F | |
| 1-218 | CH$_2$OCH$_2$CH$_2$SO$_2$Me | Et | F | |
| 1-219 | CH$_2$OCH$_2$CH$_2$SO$_2$Me | n-Pr | F | |
| 1-220 | CH$_2$OCH$_2$CH$_2$SO$_2$Me | i-Pr | F | |
| 1-221 | CH$_2$SO$_2$CH$_2$CH$_2$OMe | Me | F | |
| 1-222 | CH$_2$SO$_2$CH$_2$CH$_2$OMe | Et | F | |
| 1-223 | CH$_2$SO$_2$CH$_2$CH$_2$OMe | n-Pr | F | |
| 1-224 | CH$_2$SO$_2$CH$_2$CH$_2$OMe | i-Pr | F | |
| 1-225 | CH$_2$SO$_2$CH$_2$CH$_2$SO$_2$Me | Me | F | |
| 1-226 | CH$_2$SO$_2$CH$_2$CH$_2$SO$_2$Me | Et | F | |
| 1-227 | CH$_2$SO$_2$CH$_2$CH$_2$SO$_2$Me | n-Pr | F | |
| 1-228 | CH$_2$SO$_2$CH$_2$CH$_2$SO$_2$Me | i-Pr | F | |

TABLE 1-continued

Compounds of the formula (I) according to the invention in which $R^1$ is methyl, $R^2$ and $R^4$ are each hydrogen.

| No. | X | $R^3$ | Y | Physical data: $^1$H—NMR: δ [CDCl$_3$] |
|---|---|---|---|---|
| 1-229 | Cl | Me | Cl | |
| 1-230 | Cl | Et | Cl | |
| 1-231 | Cl | n-Pr | Cl | |
| 1-232 | Cl | i-Pr | Cl | |
| 1-233 | Br | Me | Cl | |
| 1-234 | Br | Et | Cl | |
| 1-235 | Br | n-Pr | Cl | |
| 1-236 | Br | i-Pr | Cl | |
| 1-237 | Me | Me | Cl | 7.41 (d, 1 H), 7.36 (d, 1 H), 7.32 (s, 1 H), 3.71 (s, 3 H), 3.02 (s, 3 H), 2.74 (s, 3 H) |
| 1-238 | Me | Et | Cl | 7.41 (d, 1 H), 7.36 (d, 1 H), 7.31 (s, 1 H), 3.71 (s, 3 H), 3.38 (m, 1 H), 3.16 (m, 1 H), 2.72 (s, 3 H), 1.41 (t, 3 H) |
| 1-239 | Me | n-Pr | Cl | |
| 1-240 | Me | i-Pr | Cl | |
| 1-241 | Et | Me | Cl | |
| 1-242 | Et | Et | Cl | |
| 1-243 | Et | n-Pr | Cl | |
| 1-244 | Et | i-Pr | Cl | |
| 1-245 | CF$_3$ | Me | Cl | |
| 1-246 | CF$_3$ | Et | Cl | |
| 1-247 | CF$_3$ | n-Pr | Cl | |
| 1-248 | CF$_3$ | i-Pr | Cl | |
| 1-249 | OMe | Me | Cl | |
| 1-250 | OMe | Et | Cl | |
| 1-251 | OMe | n-Pr | Cl | |
| 1-252 | OMe | i-Pr | Cl | |
| 1-253 | OEt | Me | Cl | |
| 1-254 | OEt | Et | Cl | |
| 1-255 | OEt | n-Pr | Cl | |
| 1-256 | OEt | i-Pr | Cl | |
| 1-257 | NO$_2$ | Me | Cl | |
| 1-258 | NO$_2$ | Et | Cl | |
| 1-259 | NO$_2$ | n-Pr | Cl | |
| 1-260 | NO$_2$ | i-Pr | Cl | |
| 1-261 | SO$_2$Me | Me | Cl | |
| 1-262 | SO$_2$Me | Et | Cl | |
| 1-263 | SO$_2$Me | n-Pr | Cl | |
| 1-264 | SO$_2$Me | i-Pr | Cl | |
| 1-265 | CH$_2$OMe | Me | Cl | |
| 1-266 | CH$_2$OMe | Et | Cl | |
| 1-267 | CH$_2$OMe | n-Pr | Cl | |
| 1-268 | CH$_2$OMe | i-Pr | Cl | |
| 1-269 | CH$_2$SO$_2$Me | Me | Cl | |
| 1-270 | CH$_2$SO$_2$Me | Et | Cl | |
| 1-271 | CH$_2$SO$_2$Me | n-Pr | Cl | |
| 1-272 | CH$_2$SO$_2$Me | i-Pr | Cl | |
| 1-273 | CH$_2$OCH$_2$CH$_2$OMe | Me | Cl | |
| 1-274 | CH$_2$OCH$_2$CH$_2$OMe | Et | Cl | |
| 1-275 | CH$_2$OCH$_2$CH$_2$OMe | n-Pr | Cl | |
| 1-276 | CH$_2$OCH$_2$CH$_2$OMe | i-Pr | Cl | |
| 1-277 | CH$_2$OCH$_2$CH$_2$OEt | Me | Cl | |
| 1-278 | CH$_2$OCH$_2$CH$_2$OEt | Et | Cl | |
| 1-279 | CH$_2$OCH$_2$CH$_2$OEt | n-Pr | Cl | |
| 1-280 | CH$_2$OCH$_2$CH$_2$OEt | i-Pr | Cl | |
| 1-281 | CH$_2$OCH$_2$CH$_2$CH$_2$OMe | Me | Cl | |
| 1-282 | CH$_2$OCH$_2$CH$_2$CH$_2$OMe | Et | Cl | |
| 1-283 | CH$_2$OCH$_2$CH$_2$CH$_2$OMe | n-Pr | Cl | |
| 1-284 | CH$_2$OCH$_2$CH$_2$CH$_2$OMe | i-Pr | Cl | |
| 1-285 | CH$_2$OCH$_2$OMe | Me | Cl | |
| 1-286 | CH$_2$OCH$_2$OMe | Et | Cl | |
| 1-287 | CH$_2$OCH$_2$OMe | n-Pr | Cl | |

TABLE 1-continued

Compounds of the formula (I) according to the invention in which $R^1$ is methyl, $R^2$ and $R^4$ are each hydrogen.

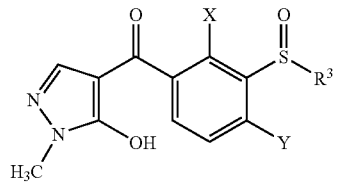

| No. | X | $R^3$ | Y | Physical data: $^1$H—NMR: δ [CDCl$_3$] |
|---|---|---|---|---|
| 1-288 | CH$_2$OCH$_2$OMe | i-Pr | Cl | |
| 1-289 | CH$_2$OCH$_2$OEt | Me | Cl | |
| 1-290 | CH$_2$OCH$_2$OEt | Et | Cl | |
| 1-291 | CH$_2$OCH$_2$OEt | n-Pr | Cl | |
| 1-292 | CH$_2$OCH$_2$OEt | i-Pr | Cl | |
| 1-293 | CH$_2$OCH$_2$CH$_2$SO$_2$Me | Me | Cl | |
| 1-294 | CH$_2$OCH$_2$CH$_2$SO$_2$Me | Et | Cl | |
| 1-295 | CH$_2$OCH$_2$CH$_2$SO$_2$Me | n-Pr | Cl | |
| 1-296 | CH$_2$OCH$_2$CH$_2$SO$_2$Me | i-Pr | Cl | |
| 1-297 | CH$_2$SO$_2$CH$_2$CH$_2$OMe | Me | Cl | |
| 1-298 | CH$_2$SO$_2$CH$_2$CH$_2$OMe | Et | Cl | |
| 1-299 | CH$_2$SO$_2$CH$_2$CH$_2$OMe | n-Pr | Cl | |
| 1-300 | CH$_2$SO$_2$CH$_2$CH$_2$OMe | i-Pr | Cl | |
| 1-301 | CH$_2$SO$_2$CH$_2$CH$_2$SO$_2$Me | Me | Cl | |
| 1-302 | CH$_2$SO$_2$CH$_2$CH$_2$SO$_2$Me | Et | Cl | |
| 1-303 | CH$_2$SO$_2$CH$_2$CH$_2$SO$_2$Me | n-Pr | Cl | |
| 1-304 | CH$_2$SO$_2$CH$_2$CH$_2$SO$_2$Me | i-Pr | Cl | |
| 1-305 | Cl | Me | Br | |
| 1-306 | Cl | Et | Br | |
| 1-307 | Cl | n-Pr | Br | |
| 1-308 | Cl | i-Pr | Br | |
| 1-309 | Br | Me | Br | |
| 1-310 | Br | Et | Br | |
| 1-311 | Br | n-Pr | Br | |
| 1-312 | Br | i-Pr | Br | |
| 1-313 | Me | Me | Br | 7.55 (d, 1 H), 7.32 (s, 1 H), 7.30 (d, 1 H), 3.72 (s, 3 H), 3.01 (s, 3 H), 2.77 (s, 3 H) |
| 1-314 | Me | Et | Br | |
| 1-315 | Me | n-Pr | Br | |
| 1-316 | Me | i-Pr | Br | |
| 1-317 | Et | Me | Br | |
| 1-318 | Et | Et | Br | |
| 1-319 | Et | n-Pr | Br | |
| 1-320 | Et | i-Pr | Br | |
| 1-321 | CF$_3$ | Me | Br | |
| 1-322 | CF$_3$ | Et | Br | |
| 1-323 | CF$_3$ | n-Pr | Br | |
| 1-324 | CF$_3$ | i-Pr | Br | |
| 1-325 | OMe | Me | Br | |
| 1-326 | OMe | Et | Br | |
| 1-327 | OMe | n-Pr | Br | |
| 1-328 | OMe | i-Pr | Br | |
| 1-329 | OEt | Me | Br | |
| 1-330 | OEt | Et | Br | |
| 1-331 | OEt | n-Pr | Br | |
| 1-332 | OEt | i-Pr | Br | |
| 1-333 | NO$_2$ | Me | Br | |
| 1-334 | NO$_2$ | Et | Br | |
| 1-335 | NO$_2$ | n-Pr | Br | |
| 1-336 | NO$_2$ | i-Pr | Br | |
| 1-337 | SO$_2$Me | Me | Br | |
| 1-338 | SO$_2$Me | Et | Br | |
| 1-339 | SO$_2$Me | n-Pr | Br | |
| 1-340 | SO$_2$Me | i-Pr | Br | |
| 1-341 | CH$_2$OMe | Me | Br | |
| 1-342 | CH$_2$OMe | Et | Br | |
| 1-343 | CH$_2$OMe | n-Pr | Br | |
| 1-344 | CH$_2$OMe | i-Pr | Br | |
| 1-345 | CH$_2$SO$_2$Me | Me | Br | |
| 1-346 | CH$_2$SO$_2$Me | Et | Br | |
| 1-347 | CH$_2$SO$_2$Me | n-Pr | Br | |
| 1-348 | CH$_2$SO$_2$Me | i-Pr | Br | |
| 1-349 | CH$_2$OCH$_2$OMe | Me | Br | |

TABLE 1-continued

Compounds of the formula (I) according to the invention in which R¹ is methyl, R² and R⁴ are each hydrogen.

| No. | X | R³ | Y | Physical data: $^1$H—NMR: δ [CDCl$_3$] |
|---|---|---|---|---|
| 1-350 | CH$_2$OCH$_2$CH$_2$OMe | Et | Br | |
| 1-351 | CH$_2$OCH$_2$CH$_2$OMe | n-Pr | Br | |
| 1-352 | CH$_2$OCH$_2$CH$_2$OMe | i-Pr | Br | |
| 1-353 | CH$_2$OCH$_2$CH$_2$OEt | Me | Br | |
| 1-354 | CH$_2$OCH$_2$CH$_2$OEt | Et | Br | |
| 1-355 | CH$_2$OCH$_2$CH$_2$OEt | n-Pr | Br | |
| 1-356 | CH$_2$OCH$_2$CH$_2$OEt | i-Pr | Br | |
| 1-357 | CH$_2$OCH$_2$CH$_2$CH$_2$OMe | Me | Br | |
| 1-358 | CH$_2$OCH$_2$CH$_2$CH$_2$OMe | Et | Br | |
| 1-359 | CH$_2$OCH$_2$CH$_2$CH$_2$OMe | n-Pr | Br | |
| 1-360 | CH$_2$OCH$_2$CH$_2$CH$_2$OMe | i-Pr | Br | |
| 1-361 | CH$_2$OCH$_2$OMe | Me | Br | |
| 1-362 | CH$_2$OCH$_2$OMe | Et | Br | |
| 1-363 | CH$_2$OCH$_2$OMe | n-Pr | Br | |
| 1-364 | CH$_2$OCH$_2$OMe | i-Pr | Br | |
| 1-365 | CH$_2$OCH$_2$OEt | Me | Br | |
| 1-366 | CH$_2$OCH$_2$OEt | Et | Br | |
| 1-367 | CH$_2$OCH$_2$OEt | n-Pr | Br | |
| 1-368 | CH$_2$OCH$_2$OEt | i-Pr | Br | |
| 1-369 | CH$_2$OCH$_2$CH$_2$SO$_2$Me | Me | Br | |
| 1-370 | CH$_2$OCH$_2$CH$_2$SO$_2$Me | Et | Br | |
| 1-371 | CH$_2$OCH$_2$CH$_2$SO$_2$Me | n-Pr | Br | |
| 1-372 | CH$_2$OCH$_2$CH$_2$SO$_2$Me | i-Pr | Br | |
| 1-373 | CH$_2$SO$_2$CH$_2$CH$_2$OMe | Me | Br | |
| 1-374 | CH$_2$SO$_2$CH$_2$CH$_2$OMe | Et | Br | |
| 1-375 | CH$_2$SO$_2$CH$_2$CH$_2$OMe | n-Pr | Br | |
| 1-376 | CH$_2$SO$_2$CH$_2$CH$_2$OMe | i-Pr | Br | |
| 1-377 | CH$_2$SO$_2$CH$_2$CH$_2$SO$_2$Me | Me | Br | |
| 1-378 | CH$_2$SO$_2$CH$_2$CH$_2$SO$_2$Me | Et | Br | |
| 1-379 | CH$_2$SO$_2$CH$_2$CH$_2$SO$_2$Me | n-Pr | Br | |
| 1-380 | CH$_2$SO$_2$CH$_2$CH$_2$SO$_2$Me | i-Pr | Br | |
| 1-381 | Cl | Me | I | |
| 1-382 | Cl | Et | I | |
| 1-383 | Cl | n-Pr | I | |
| 1-384 | Cl | i-Pr | I | |
| 1-385 | Br | Me | I | |
| 1-386 | Br | Et | I | |
| 1-387 | Br | n-Pr | I | |
| 1-388 | Br | i-Pr | I | |
| 1-389 | Me | Me | I | 7.86 (d, 1 H), 7.31 (s, 1 H), 7.11 (d, 1 H), 3.71 (s, 3 H), 2.98 (s, 3 H), 2.76 (s, 3 H) |
| 1-390 | Me | Et | I | |
| 1-391 | Me | n-Pr | I | |
| 1-392 | Me | i-Pr | I | |
| 1-393 | Et | Me | I | |
| 1-394 | Et | Et | I | |
| 1-395 | Et | n-Pr | I | |
| 1-396 | Et | i-Pr | I | |
| 1-397 | CF$_3$ | Me | I | |
| 1-398 | CF$_3$ | Et | I | |
| 1-399 | CF$_3$ | n-Pr | I | |
| 1-400 | CF$_3$ | i-Pr | I | |
| 1-401 | OMe | Me | I | |
| 1-402 | OMe | Et | I | |
| 1-403 | OMe | n-Pr | I | |
| 1-404 | OMe | i-Pr | I | |
| 1-405 | OEt | Me | I | |
| 1-406 | OEt | Et | I | |
| 1-407 | OEt | n-Pr | I | |
| 1-408 | OEt | i-Pr | I | |
| 1-409 | NO$_2$ | Me | I | |
| 1-410 | NO$_2$ | Et | I | |
| 1-411 | NO$_2$ | n-Pr | I | |

TABLE 1-continued

Compounds of the formula (I) according to the invention in which R¹ is methyl, R² and R⁴ are each hydrogen.

| No. | X | R³ | Y | Physical data: ¹H—NMR: δ [CDCl₃] |
|---|---|---|---|---|
| 1-412 | NO₂ | i-Pr | I | |
| 1-413 | SO₂Me | Me | I | |
| 1-414 | SO₂Me | Et | I | |
| 1-415 | SO₂Me | n-Pr | I | |
| 1-416 | SO₂Me | i-Pr | I | |
| 1-417 | CH₂OMe | Me | I | |
| 1-418 | CH₂OMe | Et | I | |
| 1-419 | CH₂OMe | n-Pr | I | |
| 1-420 | CH₂OMe | i-Pr | I | |
| 1-421 | CH₂SO₂Me | Me | I | |
| 1-422 | CH₂SO₂Me | Et | I | |
| 1-423 | CH₂SO₂Me | n-Pr | I | |
| 1-424 | CH₂SO₂Me | i-Pr | I | |
| 1-425 | CH₂OCH₂CH₂OMe | Me | I | |
| 1-426 | CH₂OCH₂CH₂OMe | Et | I | |
| 1-427 | CH₂OCH₂CH₂OMe | n-Pr | I | |
| 1-428 | CH₂OCH₂CH₂OMe | i-Pr | I | |
| 1-429 | CH₂OCH₂CH₂OEt | Me | I | |
| 1-430 | CH₂OCH₂CH₂OEt | Et | I | |
| 1-431 | CH₂OCH₂CH₂OEt | n-Pr | I | |
| 1-432 | CH₂OCH₂CH₂OEt | i-Pr | I | |
| 1-433 | CH₂OCH₂CH₂CH₂OMe | Me | I | |
| 1-434 | CH₂OCH₂CH₂CH₂OMe | Et | I | |
| 1-435 | CH₂OCH₂CH₂CH₂OMe | n-Pr | I | |
| 1-436 | CH₂OCH₂CH₂CH₂OMe | i-Pr | I | |
| 1-437 | CH₂OCH₂OMe | Me | I | |
| 1-438 | CH₂OCH₂OMe | Et | I | |
| 1-439 | CH₂OCH₂OMe | n-Pr | I | |
| 1-440 | CH₂OCH₂OMe | i-Pr | I | |
| 1-441 | CH₂OCH₂OEt | Me | I | |
| 1-442 | CH₂OCH₂OEt | Et | I | |
| 1-443 | CH₂OCH₂OEt | n-Pr | I | |
| 1-444 | CH₂OCH₂OEt | i-Pr | I | |
| 1-445 | CH₂OCH₂CH₂SO₂Me | Me | I | |
| 1-446 | CH₂OCH₂CH₂SO₂Me | Et | I | |
| 1-447 | CH₂OCH₂CH₂SO₂Me | n-Pr | I | |
| 1-448 | CH₂OCH₂CH₂SO₂Me | i-Pr | I | |
| 1-449 | CH₂SO₂CH₂CH₂OMe | Me | I | |
| 1-450 | CH₂SO₂CH₂CH₂OMe | Et | I | |
| 1-451 | CH₂SO₂CH₂CH₂OMe | n-Pr | I | |
| 1-452 | CH₂SO₂CH₂CH₂OMe | i-Pr | I | |
| 1-453 | CH₂SO₂CH₂CH₂SO₂Me | Me | I | |
| 1-454 | CH₂SO₂CH₂CH₂SO₂Me | Et | I | |
| 1-455 | CH₂SO₂CH₂CH₂SO₂Me | n-Pr | I | |
| 1-456 | CH₂SO₂CH₂CH₂SO₂Me | i-Pr | I | |
| 1-457 | Cl | Me | NO₂ | |
| 1-458 | Cl | Et | NO₂ | |
| 1-459 | Cl | n-Pr | NO₂ | |
| 1-460 | Cl | i-Pr | NO₂ | |
| 1-461 | Br | Me | NO₂ | |
| 1-462 | Br | Et | NO₂ | |
| 1-463 | Br | n-Pr | NO₂ | |
| 1-464 | Br | i-Pr | NO₂ | |
| 1-465 | Me | Me | NO₂ | |
| 1-466 | Me | Et | NO₂ | |
| 1-467 | Me | n-Pr | NO₂ | |
| 1-468 | Me | i-Pr | NO₂ | |
| 1-469 | Et | Me | NO₂ | |
| 1-470 | Et | Et | NO₂ | |
| 1-471 | Et | n-Pr | NO₂ | |
| 1-472 | Et | i-Pr | NO₂ | |
| 1-473 | CF₃ | Me | NO₂ | |
| 1-474 | CF₃ | Et | NO₂ | |
| 1-475 | CF₃ | n-Pr | NO₂ | |

TABLE 1-continued

Compounds of the formula (I) according to the invention in which $R^1$ is methyl, $R^2$ and $R^4$ are each hydrogen.

| No. | X | $R^3$ | Y | Physical data: $^1H$—NMR: δ [CDCl$_3$] |
|---|---|---|---|---|
| 1-476 | CF$_3$ | i-Pr | NO$_2$ | |
| 1-477 | OMe | Me | NO$_2$ | |
| 1-478 | OMe | Et | NO$_2$ | |
| 1-479 | OMe | n-Pr | NO$_2$ | |
| 1-480 | OMe | i-Pr | NO$_2$ | |
| 1-481 | OEt | Me | NO$_2$ | |
| 1-482 | OEt | Et | NO$_2$ | |
| 1-483 | OEt | n-Pr | NO$_2$ | |
| 1-484 | OEt | i-Pr | NO$_2$ | |
| 1-485 | NO$_2$ | Me | NO$_2$ | |
| 1-486 | NO$_2$ | Et | NO$_2$ | |
| 1-487 | NO$_2$ | n-Pr | NO$_2$ | |
| 1-488 | NO$_2$ | i-Pr | NO$_2$ | |
| 1-489 | SO$_2$Me | Me | NO$_2$ | |
| 1-490 | SO$_2$Me | Et | NO$_2$ | |
| 1-491 | SO$_2$Me | n-Pr | NO$_2$ | |
| 1-492 | SO$_2$Me | i-Pr | NO$_2$ | |
| 1-493 | CH$_2$OMe | Me | NO$_2$ | |
| 1-494 | CH$_2$OMe | Et | NO$_2$ | |
| 1-495 | CH$_2$OMe | n-Pr | NO$_2$ | |
| 1-496 | CH$_2$OMe | i-Pr | NO$_2$ | |
| 1-497 | CH$_2$SO$_2$Me | Me | NO$_2$ | |
| 1-498 | CH$_2$SO$_2$Me | Et | NO$_2$ | |
| 1-499 | CH$_2$SO$_2$Me | n-Pr | NO$_2$ | |
| 1-500 | CH$_2$SO$_2$Me | i-Pr | NO$_2$ | |
| 1-501 | CH$_2$OCH$_2$CH$_2$OMe | Me | NO$_2$ | |
| 1-502 | CH$_2$OCH$_2$CH$_2$OMe | Et | NO$_2$ | |
| 1-503 | CH$_2$OCH$_2$CH$_2$OMe | n-Pr | NO$_2$ | |
| 1-504 | CH$_2$OCH$_2$CH$_2$OMe | i-Pr | NO$_2$ | |
| 1-505 | CH$_2$OCH$_2$CH$_2$OEt | Me | NO$_2$ | |
| 1-506 | CH$_2$OCH$_2$CH$_2$OEt | Et | NO$_2$ | |
| 1-507 | CH$_2$OCH$_2$CH$_2$OEt | n-Pr | NO$_2$ | |
| 1-508 | CH$_2$OCH$_2$CH$_2$OEt | i-Pr | NO$_2$ | |
| 1-509 | CH$_2$OCH$_2$CH$_2$CH$_2$OMe | Me | NO$_2$ | |
| 1-510 | CH$_2$OCH$_2$CH$_2$CH$_2$OMe | Et | NO$_2$ | |
| 1-511 | CH$_2$OCH$_2$CH$_2$CH$_2$OMe | n-Pr | NO$_2$ | |
| 1-512 | CH$_2$OCH$_2$CH$_2$CH$_2$OMe | i-Pr | NO$_2$ | |
| 1-513 | CH$_2$OCH$_2$OMe | Me | NO$_2$ | |
| 1-514 | CH$_2$OCH$_2$OMe | Et | NO$_2$ | |
| 1-515 | CH$_2$OCH$_2$OMe | n-Pr | NO$_2$ | |
| 1-516 | CH$_2$OCH$_2$OMe | i-Pr | NO$_2$ | |
| 1-517 | CH$_2$OCH$_2$OEt | Me | NO$_2$ | |
| 1-518 | CH$_2$OCH$_2$OEt | Et | NO$_2$ | |
| 1-519 | CH$_2$OCH$_2$OEt | n-Pr | NO$_2$ | |
| 1-520 | CH$_2$OCH$_2$OEt | i-Pr | NO$_2$ | |
| 1-521 | CH$_2$OCH$_2$CH$_2$SO$_2$Me | Me | NO$_2$ | |
| 1-522 | CH$_2$OCH$_2$CH$_2$SO$_2$Me | Et | NO$_2$ | |
| 1-523 | CH$_2$OCH$_2$CH$_2$SO$_2$Me | n-Pr | NO$_2$ | |
| 1-524 | CH$_2$OCH$_2$CH$_2$SO$_2$Me | i-Pr | NO$_2$ | |
| 1-525 | CH$_2$SO$_2$CH$_2$CH$_2$OMe | Me | NO$_2$ | |
| 1-526 | CH$_2$SO$_2$CH$_2$CH$_2$OMe | Et | NO$_2$ | |
| 1-527 | CH$_2$SO$_2$CH$_2$CH$_2$OMe | n-Pr | NO$_2$ | |
| 1-528 | CH$_2$SO$_2$CH$_2$CH$_2$OMe | i-Pr | NO$_2$ | |
| 1-529 | CH$_2$SO$_2$CH$_2$CH$_2$SO$_2$Me | Me | NO$_2$ | |
| 1-530 | CH$_2$SO$_2$CH$_2$CH$_2$SO$_2$Me | Et | NO$_2$ | |
| 1-531 | CH$_2$SO$_2$CH$_2$CH$_2$SO$_2$Me | n-Pr | NO$_2$ | |
| 1-532 | CH$_2$SO$_2$CH$_2$CH$_2$SO$_2$Me | i-Pr | NO$_2$ | |

The abbreviations used are:
Et = ethyl
Me = methyl
Pr = propyl
Ph = phenyl

TABLE 2

Compounds of the formula (I) according to the invention in which $R^1$ is ethyl, $R^2$ and $R^4$ are each hydrogen.

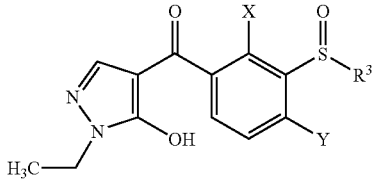

| No. | X | $R^3$ | Y | Physical data: $^1$H-NMR: δ [CDCl$_3$] |
|---|---|---|---|---|
| 2-1 | Cl | Me | SO$_2$Me | |
| 2-2 | Cl | Et | SO$_2$Me | |
| 2-3 | Cl | n-Pr | SO$_2$Me | |
| 2-4 | Cl | i-Pr | SO$_2$Me | |
| 2-5 | Br | Me | SO$_2$Me | |
| 2-6 | Br | Et | SO$_2$Me | |
| 2-7 | Br | n-Pr | SO$_2$Me | |
| 2-8 | Br | i-Pr | SO$_2$Me | |
| 2-9 | Me | Me | SO$_2$Me | 8.08 (d, 1H), 7.62 (d, 1H), 7.28 (s, 1H), 4.09 (q, 2H), 3.38 (s, 3H), 3.18 (s, 3H), 2.88 (s, 3H), 1.46 (t, 3H) |
| 2-10 | Me | Et | SO$_2$Me | 8.10 (d, 1H), 7.62 (d, 1H), 7.28 (s, 1H), 4.08 (q, 2H), 3.52 (m, 1H), 3.38 (s, 3H), 3.28 (m, 1H), 2.82 (s, 3H), 1.52 (t, 3H), 1.47 (t, 3H) |
| 2-11 | Me | n-Pr | SO$_2$Me | 8.08 (d, 1H), 7.61 (d, 1H), 7.27 (s, 1H), 4.08 (q, 2H), 3.52 (m, 1H), 3.37 (s, 3H), 3.16 (m, 1H), 2.83 (s, 3H), 2.02 (m, 2H), 1.47 (t, 3H), 1.17 (t, 3H) |
| 2-12 | Me | i-Pr | SO$_2$Me | 8.17 (m, 1H), 7.62 (d, 1H), 7.26 (s, 1H), 4.08 (q, 2H), 3.74 (m, 1H), 3.37 (s, 3H), 2.87 (s, 3H), 1.55 (d, 3H), 1.47 (t, 3H), 1.27 (m, 3H) |
| 2-13 | Et | Me | SO$_2$Me | |
| 2-14 | Et | Et | SO$_2$Me | |
| 2-15 | Et | n-Pr | SO$_2$Me | |
| 2-16 | Et | i-Pr | SO$_2$Me | |
| 2-17 | CF$_3$ | Me | SO$_2$Me | |
| 2-18 | CF$_3$ | Et | SO$_2$Me | |
| 2-19 | CF$_3$ | n-Pr | SO$_2$Me | |
| 2-20 | CF$_3$ | i-Pr | SO$_2$Me | |
| 2-21 | OMe | Me | SO$_2$Me | |
| 2-22 | OMe | Et | SO$_2$Me | |
| 2-23 | OMe | n-Pr | SO$_2$Me | |
| 2-24 | OMe | i-Pr | SO$_2$Me | |
| 2-25 | OEt | Me | SO$_2$Me | |
| 2-26 | OEt | Et | SO$_2$Me | |
| 2-27 | OEt | n-Pr | SO$_2$Me | |
| 2-28 | OEt | i-Pr | SO$_2$Me | |
| 2-29 | NO$_2$ | Me | SO$_2$Me | |
| 2-30 | NO$_2$ | Et | SO$_2$Me | |
| 2-31 | NO$_2$ | n-Pr | SO$_2$Me | |
| 2-32 | NO$_2$ | i-Pr | SO$_2$Me | |
| 2-33 | SO$_2$Me | Me | SO$_2$Me | |
| 2-34 | SO$_2$Me | Et | SO$_2$Me | |
| 2-35 | SO$_2$Me | n-Pr | SO$_2$Me | |
| 2-36 | SO$_2$Me | i-Pr | SO$_2$Me | |
| 2-37 | CH$_2$OMe | Me | SO$_2$Me | |
| 2-38 | CH$_2$OMe | Et | SO$_2$Me | |
| 2-39 | CH$_2$OMe | n-Pr | SO$_2$Me | |
| 2-40 | CH$_2$OMe | i-Pr | SO$_2$Me | |
| 2-41 | CH$_2$SO$_2$Me | Me | SO$_2$Me | |
| 2-42 | CH$_2$SO$_2$Me | Et | SO$_2$Me | |
| 2-43 | CH$_2$SO$_2$Me | n-Pr | SO$_2$Me | |
| 2-44 | CH$_2$SO$_2$Me | i-Pr | SO$_2$Me | |
| 2-45 | CH$_2$OCH$_2$CH$_2$OMe | Me | SO$_2$Me | |
| 2-46 | CH$_2$OCH$_2$CH$_2$OMe | Et | SO$_2$Me | |
| 2-47 | CH$_2$OCH$_2$CH$_2$OMe | n-Pr | SO$_2$Me | |
| 2-48 | CH$_2$OCH$_2$CH$_2$OMe | i-Pr | SO$_2$Me | |
| 2-49 | CH$_2$OCH$_2$CH$_2$OEt | Me | SO$_2$Me | 8.22 (d, 1H), 7.67 (d, 1H), 7.38 (s, 1H), 5.60-5.10 (br. signal, 1H), 4.97 (d, 1H), 4.09 (q, 2H), 3.62-3.56 (m, 1H), 3.56-3.49 (m, 1H), 3.47-3.32 (m, 4H), 3.37 (s, 3H), 3.33 (s, 3H), 1.46 (t, 3H), 1.12 (t, 3H) |
| 2-50 | CH$_2$OCH$_2$CH$_2$OEt | Et | SO$_2$Me | |
| 2-51 | CH$_2$OCH$_2$CH$_2$OEt | n-Pr | SO$_2$Me | |
| 2-52 | CH$_2$OCH$_2$CH$_2$OEt | i-Pr | SO$_2$Me | |
| 2-53 | CH$_2$OCH$_2$CH$_2$CH$_2$OMe | Me | SO$_2$Me | |
| 2-54 | CH$_2$OCH$_2$CH$_2$CH$_2$OMe | Et | SO$_2$Me | |
| 2-55 | CH$_2$OCH$_2$CH$_2$CH$_2$OMe | n-Pr | SO$_2$Me | |
| 2-56 | CH$_2$OCH$_2$CH$_2$CH$_2$OMe | i-Pr | SO$_2$Me | |
| 2-57 | CH$_2$OCH$_2$OMe | Me | SO$_2$Me | |
| 2-58 | CH$_2$OCH$_2$OMe | Et | SO$_2$Me | |
| 2-59 | CH$_2$OCH$_2$OMe | n-Pr | SO$_2$Me | |
| 2-60 | CH$_2$OCH$_2$OMe | i-Pr | SO$_2$Me | |
| 2-61 | CH$_2$OCH$_2$OEt | Me | SO$_2$Me | |
| 2-62 | CH$_2$OCH$_2$OEt | Et | SO$_2$Me | |
| 2-63 | CH$_2$OCH$_2$OEt | n-Pr | SO$_2$Me | |
| 2-64 | CH$_2$OCH$_2$OEt | i-Pr | SO$_2$Me | |
| 2-65 | CH$_2$OCH$_2$CH$_2$SO$_2$Me | Me | SO$_2$Me | |
| 2-66 | CH$_2$OCH$_2$CH$_2$SO$_2$Me | Et | SO$_2$Me | |
| 2-67 | CH$_2$OCH$_2$CH$_2$SO$_2$Me | n-Pr | SO$_2$Me | |
| 2-68 | CH$_2$OCH$_2$CH$_2$SO$_2$Me | i-Pr | SO$_2$Me | |
| 2-69 | CH$_2$SO$_2$CH$_2$CH$_2$OMe | Me | SO$_2$Me | |
| 2-70 | CH$_2$SO$_2$CH$_2$CH$_2$OMe | Et | SO$_2$Me | |
| 2-71 | CH$_2$SO$_2$CH$_2$CH$_2$OMe | n-Pr | SO$_2$Me | |
| 2-72 | CH$_2$SO$_2$CH$_2$CH$_2$OMe | i-Pr | SO$_2$Me | |
| 2-73 | CH$_2$SO$_2$CH$_2$CH$_2$SO$_2$Me | Me | SO$_2$Me | |
| 2-74 | CH$_2$SO$_2$CH$_2$CH$_2$SO$_2$Me | Et | SO$_2$Me | |
| 2-75 | CH$_2$SO$_2$CH$_2$CH$_2$SO$_2$Me | n-Pr | SO$_2$Me | |
| 2-76 | CH$_2$SO$_2$CH$_2$CH$_2$SO$_2$Me | i-Pr | SO$_2$Me | |
| 2-77 | Cl | Me | SO$_2$Et | |
| 2-78 | Cl | Et | SO$_2$Et | |
| 2-79 | Cl | n-Pr | SO$_2$Et | |
| 2-80 | Cl | i-Pr | SO$_2$Et | |
| 2-81 | Br | Me | SO$_2$Et | |
| 2-82 | Br | Et | SO$_2$Et | |
| 2-83 | Br | n-Pr | SO$_2$Et | |
| 2-84 | Br | i-Pr | SO$_2$Et | |
| 2-85 | Me | Me | SO$_2$Et | |
| 2-86 | Me | Et | SO$_2$Et | |
| 2-87 | Me | n-Pr | SO$_2$Et | |
| 2-88 | Me | i-Pr | SO$_2$Et | |
| 2-89 | Et | Me | SO$_2$Et | |
| 2-90 | Et | Et | SO$_2$Et | |
| 2-91 | Et | n-Pr | SO$_2$Et | |
| 2-92 | Et | i-Pr | SO$_2$Et | |
| 2-93 | CF$_3$ | Me | SO$_2$Et | |
| 2-94 | CF$_3$ | Et | SO$_2$Et | |
| 2-95 | CF$_3$ | n-Pr | SO$_2$Et | |
| 2-96 | CF$_3$ | i-Pr | SO$_2$Et | |
| 2-97 | OMe | Me | SO$_2$Et | |
| 2-98 | OMe | Et | SO$_2$Et | |

TABLE 2-continued

Compounds of the formula (I) according to the invention in which $R^1$ is ethyl, $R^2$ and $R^4$ are each hydrogen.

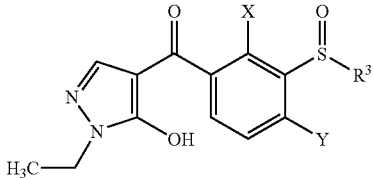

| No. | X | $R^3$ | Y | Physical data: $^1$H-NMR: δ [CDCl$_3$] |
|---|---|---|---|---|
| 2-99 | OMe | n-Pr | SO$_2$Et | |
| 2-100 | OMe | i-Pr | SO$_2$Et | |
| 2-101 | OEt | Me | SO$_2$Et | |
| 2-102 | OEt | Et | SO$_2$Et | |
| 2-103 | OEt | n-Pr | SO$_2$Et | |
| 2-104 | OEt | i-Pr | SO$_2$Et | |
| 2-105 | NO$_2$ | Me | SO$_2$Et | |
| 2-106 | NO$_2$ | Et | SO$_2$Et | |
| 2-107 | NO$_2$ | n-Pr | SO$_2$Et | |
| 2-108 | NO$_2$ | i-Pr | SO$_2$Et | |
| 2-109 | SO$_2$Me | Me | SO$_2$Et | |
| 2-110 | SO$_2$Me | Et | SO$_2$Et | |
| 2-111 | SO$_2$Me | n-Pr | SO$_2$Et | |
| 2-112 | SO$_2$Me | i-Pr | SO$_2$Et | |
| 2-113 | CH$_2$OMe | Me | SO$_2$Et | |
| 2-114 | CH$_2$OMe | Et | SO$_2$Et | |
| 2-115 | CH$_2$OMe | n-Pr | SO$_2$Et | |
| 2-116 | CH$_2$OMe | i-Pr | SO$_2$Et | |
| 2-117 | CH$_2$SO$_2$Me | Me | SO$_2$Et | |
| 2-118 | CH$_2$SO$_2$Me | Et | SO$_2$Et | |
| 2-119 | CH$_2$SO$_2$Me | n-Pr | SO$_2$Et | |
| 2-120 | CH$_2$SO$_2$Me | i-Pr | SO$_2$Et | |
| 2-121 | CH$_2$OCH$_2$CH$_2$OMe | Me | SO$_2$Et | |
| 2-122 | CH$_2$OCH$_2$CH$_2$OMe | Et | SO$_2$Et | |
| 2-123 | CH$_2$OCH$_2$CH$_2$OMe | n-Pr | SO$_2$Et | |
| 2-124 | CH$_2$OCH$_2$CH$_2$OMe | i-Pr | SO$_2$Et | |
| 2-125 | CH$_2$OCH$_2$CH$_2$OEt | Me | SO$_2$Et | |
| 2-126 | CH$_2$OCH$_2$CH$_2$OEt | Et | SO$_2$Et | |
| 2-127 | CH$_2$OCH$_2$CH$_2$OEt | n-Pr | SO$_2$Et | |
| 2-128 | CH$_2$OCH$_2$CH$_2$OEt | i-Pr | SO$_2$Et | |
| 2-129 | CH$_2$OCH$_2$CH$_2$CH$_2$OMe | Me | SO$_2$Et | |
| 2-130 | CH$_2$OCH$_2$CH$_2$CH$_2$OMe | Et | SO$_2$Et | |
| 2-131 | CH$_2$OCH$_2$CH$_2$CH$_2$OMe | n-Pr | SO$_2$Et | |
| 2-132 | CH$_2$OCH$_2$CH$_2$CH$_2$OMe | i-Pr | SO$_2$Et | |
| 2-133 | CH$_2$OCH$_2$OMe | Me | SO$_2$Et | |
| 2-134 | CH$_2$OCH$_2$OMe | Et | SO$_2$Et | |
| 2-135 | CH$_2$OCH$_2$OMe | n-Pr | SO$_2$Et | |
| 2-136 | CH$_2$OCH$_2$OMe | i-Pr | SO$_2$Et | |
| 2-137 | CH$_2$OCH$_2$OEt | Me | SO$_2$Et | |
| 2-138 | CH$_2$OCH$_2$OEt | Et | SO$_2$Et | |
| 2-139 | CH$_2$OCH$_2$OEt | n-Pr | SO$_2$Et | |
| 2-140 | CH$_2$OCH$_2$OEt | i-Pr | SO$_2$Et | |
| 2-141 | CH$_2$OCH$_2$CH$_2$SO$_2$Me | Me | SO$_2$Et | |
| 2-142 | CH$_2$OCH$_2$CH$_2$SO$_2$Me | Et | SO$_2$Et | |
| 2-143 | CH$_2$OCH$_2$CH$_2$SO$_2$Me | n-Pr | SO$_2$Et | |
| 2-144 | CH$_2$OCH$_2$CH$_2$SO$_2$Me | i-Pr | SO$_2$Et | |
| 2-145 | CH$_2$SO$_2$CH$_2$CH$_2$OMe | Me | SO$_2$Et | |
| 2-146 | CH$_2$SO$_2$CH$_2$CH$_2$OMe | Et | SO$_2$Et | |
| 2-147 | CH$_2$SO$_2$CH$_2$CH$_2$OMe | n-Pr | SO$_2$Et | |
| 2-148 | CH$_2$SO$_2$CH$_2$CH$_2$OMe | i-Pr | SO$_2$Et | |
| 2-149 | CH$_2$SO$_2$CH$_2$CH$_2$SO$_2$Me | Me | SO$_2$Et | |
| 2-150 | CH$_2$SO$_2$CH$_2$CH$_2$SO$_2$Me | Et | SO$_2$Et | |
| 2-151 | CH$_2$SO$_2$CH$_2$CH$_2$SO$_2$Me | n-Pr | SO$_2$Et | |
| 2-152 | CH$_2$SO$_2$CH$_2$CH$_2$SO$_2$Me | i-Pr | SO$_2$Et | |
| 2-153 | Cl | Me | F | |
| 2-154 | Cl | Et | F | |
| 2-155 | Cl | n-Pr | F | |
| 2-156 | Cl | i-Pr | F | |
| 2-157 | Br | Me | F | |
| 2-158 | Br | Et | F | |
| 2-159 | Br | n-Pr | F | |
| 2-160 | Br | i-Pr | F | |
| 2-161 | Me | Me | F | |
| 2-162 | Me | Et | F | |

TABLE 2-continued

Compounds of the formula (I) according to the invention in which $R^1$ is ethyl, $R^2$ and $R^4$ are each hydrogen.

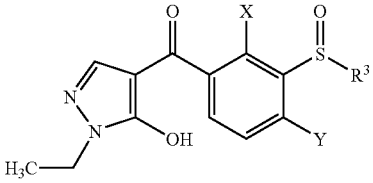

| No. | X | $R^3$ | Y | Physical data: $^1$H-NMR: δ [CDCl$_3$] |
|---|---|---|---|---|
| 2-163 | Me | n-Pr | F | |
| 2-164 | Me | i-Pr | F | |
| 2-165 | Et | Me | F | |
| 2-166 | Et | Et | F | |
| 2-167 | Et | n-Pr | F | |
| 2-168 | Et | i-Pr | F | |
| 2-169 | CF$_3$ | Me | F | |
| 2-170 | CF$_3$ | Et | F | |
| 2-171 | CF$_3$ | n-Pr | F | |
| 2-172 | CF$_3$ | i-Pr | F | |
| 2-173 | OMe | Me | F | |
| 2-174 | OMe | Et | F | |
| 2-175 | OMe | n-Pr | F | |
| 2-176 | OMe | i-Pr | F | |
| 2-177 | OEt | Me | F | |
| 2-178 | OEt | Et | F | |
| 2-179 | OEt | n-Pr | F | |
| 2-180 | OEt | i-Pr | F | |
| 2-181 | NO$_2$ | Me | F | |
| 2-182 | NO$_2$ | Et | F | |
| 2-183 | NO$_2$ | n-Pr | F | |
| 2-184 | NO$_2$ | i-Pr | F | |
| 2-185 | SO$_2$Me | Me | F | |
| 2-186 | SO$_2$Me | Et | F | |
| 2-187 | SO$_2$Me | n-Pr | F | |
| 2-188 | SO$_2$Me | i-Pr | F | |
| 2-189 | CH$_2$OMe | Me | F | |
| 2-190 | CH$_2$OMe | Et | F | |
| 2-191 | CH$_2$OMe | n-Pr | F | |
| 2-192 | CH$_2$OMe | i-Pr | F | |
| 2-193 | CH$_2$SO$_2$Me | Me | F | |
| 2-194 | CH$_2$SO$_2$Me | Et | F | |
| 2-195 | CH$_2$SO$_2$Me | n-Pr | F | |
| 2-196 | CH$_2$SO$_2$Me | i-Pr | F | |
| 2-197 | CH$_2$OCH$_2$CH$_2$OMe | Me | F | |
| 2-198 | CH$_2$OCH$_2$CH$_2$OMe | Et | F | |
| 2-199 | CH$_2$OCH$_2$CH$_2$OMe | n-Pr | F | |
| 2-200 | CH$_2$OCH$_2$CH$_2$OMe | i-Pr | F | |
| 2-201 | CH$_2$OCH$_2$CH$_2$OEt | Me | F | |
| 2-202 | CH$_2$OCH$_2$CH$_2$OEt | Et | F | |
| 2-203 | CH$_2$OCH$_2$CH$_2$OEt | n-Pr | F | |
| 2-204 | CH$_2$OCH$_2$CH$_2$OEt | i-Pr | F | |
| 2-205 | CH$_2$OCH$_2$CH$_2$CH$_2$OMe | Me | F | |
| 2-206 | CH$_2$OCH$_2$CH$_2$CH$_2$OMe | Et | F | |
| 2-207 | CH$_2$OCH$_2$CH$_2$CH$_2$OMe | n-Pr | F | |
| 2-208 | CH$_2$OCH$_2$CH$_2$CH$_2$OMe | i-Pr | F | |
| 2-209 | CH$_2$OCH$_2$OMe | Me | F | |
| 2-210 | CH$_2$OCH$_2$OMe | Et | F | |
| 2-211 | CH$_2$OCH$_2$OMe | n-Pr | F | |
| 2-212 | CH$_2$OCH$_2$OMe | i-Pr | F | |
| 2-213 | CH$_2$OCH$_2$OEt | Me | F | |
| 2-214 | CH$_2$OCH$_2$OEt | Et | F | |
| 2-215 | CH$_2$OCH$_2$OEt | n-Pr | F | |
| 2-216 | CH$_2$OCH$_2$OEt | i-Pr | F | |
| 2-217 | CH$_2$OCH$_2$CH$_2$SO$_2$Me | Me | F | |
| 2-218 | CH$_2$OCH$_2$CH$_2$SO$_2$Me | Et | F | |
| 2-219 | CH$_2$OCH$_2$CH$_2$SO$_2$Me | n-Pr | F | |
| 2-220 | CH$_2$OCH$_2$CH$_2$SO$_2$Me | i-Pr | F | |
| 2-221 | CH$_2$SO$_2$CH$_2$CH$_2$OMe | Me | F | |
| 2-222 | CH$_2$SO$_2$CH$_2$CH$_2$OMe | Et | F | |
| 2-223 | CH$_2$SO$_2$CH$_2$CH$_2$OMe | n-Pr | F | |
| 2-224 | CH$_2$SO$_2$CH$_2$CH$_2$OMe | i-Pr | F | |
| 2-225 | CH$_2$SO$_2$CH$_2$CH$_2$SO$_2$Me | Me | F | |
| 2-226 | CH$_2$SO$_2$CH$_2$CH$_2$SO$_2$Me | Et | F | |

TABLE 2-continued

Compounds of the formula (I) according to the invention in which $R^1$ is ethyl, $R^2$ and $R^4$ are each hydrogen.

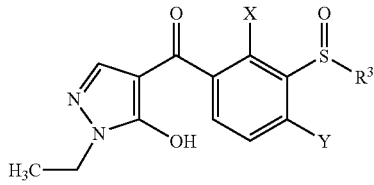

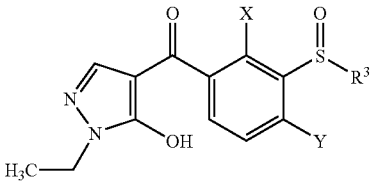

| No. | X | $R^3$ | Y | Physical data: $^1$H-NMR: δ [CDCl$_3$] |
|---|---|---|---|---|
| 2-227 | CH$_2$SO$_2$CH$_2$CH$_2$SO$_2$Me | n-Pr | F | |
| 2-228 | CH$_2$SO$_2$CH$_2$CH$_2$SO$_2$Me | i-Pr | F | |
| 2-229 | Cl | Me | Cl | |
| 2-230 | Cl | Et | Cl | |
| 2-231 | Cl | n-Pr | Cl | |
| 2-232 | Cl | i-Pr | Cl | |
| 2-233 | Br | Me | Cl | |
| 2-234 | Br | Et | Cl | |
| 2-235 | Br | n-Pr | Cl | |
| 2-236 | Br | i-Pr | Cl | |
| 2-237 | Me | Me | Cl | 7.43 (d, 1H), 7.37 (d, 1H), 7.33 (s, 1H), 4.08 (q, 2H), 3.03 (s, 3H), 2.73 (s, 3H), 1.45 (t, 3H) |
| 2-238 | Me | Et | Cl | 7.41 (d, 1H), 7.36 (d, 1H), 7.32 (s, 1H), 4.07 (q, 2H), 3.38 (m, 1H), 3.17 (m, 1H), 2.72 (s, 3H), 1.46 (t, 3H), 1.41 (t, 3H) |
| 2-239 | Me | n-Pr | Cl | |
| 2-240 | Me | i-Pr | Cl | |
| 2-241 | Et | Me | Cl | |
| 2-242 | Et | Et | Cl | |
| 2-243 | Et | n-Pr | Cl | |
| 2-244 | Et | i-Pr | Cl | |
| 2-245 | CF$_3$ | Me | Cl | |
| 2-246 | CF$_3$ | Et | Cl | |
| 2-247 | CF$_3$ | n-Pr | Cl | |
| 2-248 | CF$_3$ | i-Pr | Cl | |
| 2-249 | OMe | Me | Cl | |
| 2-250 | OMe | Et | Cl | |
| 2-251 | OMe | n-Pr | Cl | |
| 2-252 | OMe | i-Pr | Cl | |
| 2-253 | OEt | Me | Cl | |
| 2-254 | OEt | Et | Cl | |
| 2-255 | OEt | n-Pr | Cl | |
| 2-256 | OEt | i-Pr | Cl | |
| 2-257 | NO$_2$ | Me | Cl | |
| 2-258 | NO$_2$ | Et | Cl | |
| 2-259 | NO$_2$ | n-Pr | Cl | |
| 2-260 | NO$_2$ | i-Pr | Cl | |
| 2-261 | SO$_2$Me | Me | Cl | |
| 2-262 | SO$_2$Me | Et | Cl | |
| 2-263 | SO$_2$Me | n-Pr | Cl | |
| 2-264 | SO$_2$Me | i-Pr | Cl | |
| 2-265 | CH$_2$OMe | Me | Cl | |
| 2-266 | CH$_2$OMe | Et | Cl | |
| 2-267 | CH$_2$OMe | n-Pr | Cl | |
| 2-268 | CH$_2$OMe | i-Pr | Cl | |
| 2-269 | CH$_2$SO$_2$Me | Me | Cl | |
| 2-270 | CH$_2$SO$_2$Me | Et | Cl | |
| 2-271 | CH$_2$SO$_2$Me | n-Pr | Cl | |
| 2-272 | CH$_2$SO$_2$Me | i-Pr | Cl | |
| 2-273 | CH$_2$OCH$_2$CH$_2$OMe | Me | Cl | |
| 2-274 | CH$_2$OCH$_2$CH$_2$OMe | Et | Cl | |
| 2-275 | CH$_2$OCH$_2$CH$_2$OMe | n-Pr | Cl | |
| 2-276 | CH$_2$OCH$_2$CH$_2$OMe | i-Pr | Cl | |
| 2-277 | CH$_2$OCH$_2$CH$_2$OEt | Me | Cl | |
| 2-278 | CH$_2$OCH$_2$CH$_2$OEt | Et | Cl | |
| 2-279 | CH$_2$OCH$_2$CH$_2$OEt | n-Pr | Cl | |
| 2-280 | CH$_2$OCH$_2$CH$_2$OEt | i-Pr | Cl | |
| 2-281 | CH$_2$OCH$_2$CH$_2$CH$_2$OMe | Me | Cl | |
| 2-282 | CH$_2$OCH$_2$CH$_2$CH$_2$OMe | Et | Cl | |
| 2-283 | CH$_2$OCH$_2$CH$_2$CH$_2$OMe | n-Pr | Cl | |
| 2-284 | CH$_2$OCH$_2$CH$_2$CH$_2$OMe | i-Pr | Cl | |
| 2-285 | CH$_2$OCH$_2$OMe | Me | Cl | |
| 2-286 | CH$_2$OCH$_2$OMe | Et | Cl | |
| 2-287 | CH$_2$OCH$_2$OMe | n-Pr | Cl | |
| 2-288 | CH$_2$OCH$_2$OMe | i-Pr | Cl | |
| 2-289 | CH$_2$OCH$_2$OEt | Me | Cl | |
| 2-290 | CH$_2$OCH$_2$OEt | Et | Cl | |
| 2-291 | CH$_2$OCH$_2$OEt | n-Pr | Cl | |
| 2-292 | CH$_2$OCH$_2$OEt | i-Pr | Cl | |
| 2-293 | CH$_2$OCH$_2$CH$_2$SO$_2$Me | Me | Cl | |
| 2-294 | CH$_2$OCH$_2$CH$_2$SO$_2$Me | Et | Cl | |
| 2-295 | CH$_2$OCH$_2$CH$_2$SO$_2$Me | n-Pr | Cl | |
| 2-296 | CH$_2$OCH$_2$CH$_2$SO$_2$Me | i-Pr | Cl | |
| 2-297 | CH$_2$SO$_2$CH$_2$CH$_2$OMe | Me | Cl | |
| 2-298 | CH$_2$SO$_2$CH$_2$CH$_2$OMe | Et | Cl | |
| 2-299 | CH$_2$SO$_2$CH$_2$CH$_2$OMe | n-Pr | Cl | |
| 2-300 | CH$_2$SO$_2$CH$_2$CH$_2$OMe | i-Pr | Cl | |
| 2-301 | CH$_2$SO$_2$CH$_2$CH$_2$SO$_2$Me | Me | Cl | |
| 2-302 | CH$_2$SO$_2$CH$_2$CH$_2$SO$_2$Me | Et | Cl | |
| 2-303 | CH$_2$SO$_2$CH$_2$CH$_2$SO$_2$Me | n-Pr | Cl | |
| 2-304 | CH$_2$SO$_2$CH$_2$CH$_2$SO$_2$Me | i-Pr | Cl | |
| 2-305 | Cl | Me | Br | |
| 2-306 | Cl | Et | Br | |
| 2-307 | Cl | n-Pr | Br | |
| 2-308 | Cl | i-Pr | Br | |
| 2-309 | Br | Me | Br | |
| 2-310 | Br | Et | Br | |
| 2-311 | Br | n-Pr | Br | |
| 2-312 | Br | i-Pr | Br | |
| 2-313 | Me | Me | Br | 7.56 (d, 1H), 7.35 (s, 1H), 7.33 (d, 1H), 4.09 (q, 2H), 3.03 (s, 3H), 2.77 (s, 3H), 1.46 (t, 3H) |
| 2-314 | Me | Et | Br | |
| 2-315 | Me | n-Pr | Br | |
| 2-316 | Me | i-Pr | Br | |
| 2-317 | Et | Me | Br | |
| 2-318 | Et | Et | Br | |
| 2-319 | Et | n-Pr | Br | |
| 2-320 | Et | i-Pr | Br | |
| 2-321 | CF$_3$ | Me | Br | |
| 2-322 | CF$_3$ | Et | Br | |
| 2-323 | CF$_3$ | n-Pr | Br | |
| 2-324 | CF$_3$ | i-Pr | Br | |
| 2-325 | OMe | Me | Br | |
| 2-326 | OMe | Et | Br | |
| 2-327 | OMe | n-Pr | Br | |
| 2-328 | OMe | i-Pr | Br | |
| 2-329 | OEt | Me | Br | |
| 2-330 | OEt | Et | Br | |
| 2-331 | OEt | n-Pr | Br | |
| 2-332 | OEt | i-Pr | Br | |
| 2-333 | NO$_2$ | Me | Br | |
| 2-334 | NO$_2$ | Et | Br | |
| 2-335 | NO$_2$ | n-Pr | Br | |
| 2-336 | NO$_2$ | i-Pr | Br | |
| 2-337 | SO$_2$Me | Me | Br | |
| 2-338 | SO$_2$Me | Et | Br | |
| 2-339 | SO$_2$Me | n-Pr | Br | |
| 2-340 | SO$_2$Me | i-Pr | Br | |
| 2-341 | CH$_2$OMe | Me | Br | |

TABLE 2-continued

Compounds of the formula (I) according to the invention in which $R^1$ is ethyl, $R^2$ and $R^4$ are each hydrogen.

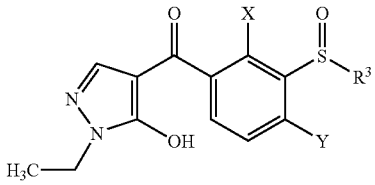

| No. | X | $R^3$ | Y | Physical data: $^1$H-NMR: δ [CDCl$_3$] |
|---|---|---|---|---|
| 2-342 | CH$_2$OMe | Et | Br | |
| 2-343 | CH$_2$OMe | n-Pr | Br | |
| 2-344 | CH$_2$OMe | i-Pr | Br | |
| 2-345 | CH$_2$SO$_2$Me | Me | Br | |
| 2-346 | CH$_2$SO$_2$Me | Et | Br | |
| 2-347 | CH$_2$SO$_2$Me | n-Pr | Br | |
| 2-348 | CH$_2$SO$_2$Me | i-Pr | Br | |
| 2-349 | CH$_2$OCH$_2$CH$_2$OMe | Me | Br | |
| 2-350 | CH$_2$OCH$_2$CH$_2$OMe | Et | Br | |
| 2-351 | CH$_2$OCH$_2$CH$_2$OMe | n-Pr | Br | |
| 2-352 | CH$_2$OCH$_2$CH$_2$OMe | i-Pr | Br | |
| 2-353 | CH$_2$OCH$_2$CH$_2$OEt | Me | Br | |
| 2-354 | CH$_2$OCH$_2$CH$_2$OEt | Et | Br | |
| 2-355 | CH$_2$OCH$_2$CH$_2$OEt | n-Pr | Br | |
| 2-356 | CH$_2$OCH$_2$CH$_2$OEt | i-Pr | Br | |
| 2-357 | CH$_2$OCH$_2$CH$_2$CH$_2$OMe | Me | Br | |
| 2-358 | CH$_2$OCH$_2$CH$_2$CH$_2$OMe | Et | Br | |
| 2-359 | CH$_2$OCH$_2$CH$_2$CH$_2$OMe | n-Pr | Br | |
| 2-360 | CH$_2$OCH$_2$CH$_2$CH$_2$OMe | i-Pr | Br | |
| 2-361 | CH$_2$OCH$_2$OMe | Me | Br | |
| 2-362 | CH$_2$OCH$_2$OMe | Et | Br | |
| 2-363 | CH$_2$OCH$_2$OMe | n-Pr | Br | |
| 2-364 | CH$_2$OCH$_2$OMe | i-Pr | Br | |
| 2-365 | CH$_2$OCH$_2$OEt | Me | Br | |
| 2-366 | CH$_2$OCH$_2$OEt | Et | Br | |
| 2-367 | CH$_2$OCH$_2$OEt | n-Pr | Br | |
| 2-368 | CH$_2$OCH$_2$OEt | i-Pr | Br | |
| 2-369 | CH$_2$OCH$_2$CH$_2$SO$_2$Me | Me | Br | |
| 2-370 | CH$_2$OCH$_2$CH$_2$SO$_2$Me | Et | Br | |
| 2-371 | CH$_2$OCH$_2$CH$_2$SO$_2$Me | n-Pr | Br | |
| 2-372 | CH$_2$OCH$_2$CH$_2$SO$_2$Me | i-Pr | Br | |
| 2-373 | CH$_2$SO$_2$CH$_2$CH$_2$OMe | Me | Br | |
| 2-374 | CH$_2$SO$_2$CH$_2$CH$_2$OMe | Et | Br | |
| 2-375 | CH$_2$SO$_2$CH$_2$CH$_2$OMe | n-Pr | Br | |
| 2-376 | CH$_2$SO$_2$CH$_2$CH$_2$OMe | i-Pr | Br | |
| 2-377 | CH$_2$SO$_2$CH$_2$CH$_2$SO$_2$Me | Me | Br | |
| 2-378 | CH$_2$SO$_2$CH$_2$CH$_2$SO$_2$Me | Et | Br | |
| 2-379 | CH$_2$SO$_2$CH$_2$CH$_2$SO$_2$Me | n-Pr | Br | |
| 2-380 | CH$_2$SO$_2$CH$_2$CH$_2$SO$_2$Me | i-Pr | Br | |
| 2-381 | Cl | Me | I | |
| 2-382 | Cl | Et | I | |
| 2-383 | Cl | n-Pr | I | |
| 2-384 | Cl | i-Pr | I | |
| 2-385 | Br | Me | I | |
| 2-386 | Br | Et | I | |
| 2-387 | Br | n-Pr | I | |
| 2-388 | Br | i-Pr | I | |
| 2-389 | Me | Me | I | 7.87 (d, 1H), 7.31 (s, 1H), 7.12 (d, 1H), 4.08 (q, 2H), 2.97 (s, 3H), 2.77 (s, 3H), 1.45 (t, 3H) |
| 2-390 | Me | Et | I | |
| 2-391 | Me | n-Pr | I | |
| 2-392 | Me | i-Pr | I | |
| 2-393 | Et | Me | I | |
| 2-394 | Et | Et | I | |
| 2-395 | Et | n-Pr | I | |
| 2-396 | Et | i-Pr | I | |
| 2-397 | CF$_3$ | Me | I | |
| 2-398 | CF$_3$ | Et | I | |
| 2-399 | CF$_3$ | n-Pr | I | |
| 2-400 | CF$_3$ | i-Pr | I | |
| 2-401 | OMe | Me | I | |

TABLE 2-continued

Compounds of the formula (I) according to the invention in which $R^1$ is ethyl, $R^2$ and $R^4$ are each hydrogen.

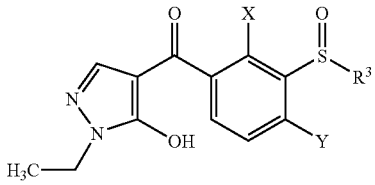

| No. | X | $R^3$ | Y | Physical data: $^1$H-NMR: δ [CDCl$_3$] |
|---|---|---|---|---|
| 2-402 | OMe | Et | I | |
| 2-403 | OMe | n-Pr | I | |
| 2-404 | OMe | i-Pr | I | |
| 2-405 | OEt | Me | I | |
| 2-406 | OEt | Et | I | |
| 2-407 | OEt | n-Pr | I | |
| 2-408 | OEt | i-Pr | I | |
| 2-409 | NO$_2$ | Me | I | |
| 2-410 | NO$_2$ | Et | I | |
| 2-411 | NO$_2$ | n-Pr | I | |
| 2-412 | NO$_2$ | i-Pr | I | |
| 2-413 | SO$_2$Me | Me | I | |
| 2-414 | SO$_2$Me | Et | I | |
| 2-415 | SO$_2$Me | n-Pr | I | |
| 2-416 | SO$_2$Me | i-Pr | I | |
| 2-417 | CH$_2$OMe | Me | I | |
| 2-418 | CH$_2$OMe | Et | I | |
| 2-419 | CH$_2$OMe | n-Pr | I | |
| 2-420 | CH$_2$OMe | i-Pr | I | |
| 2-421 | CH$_2$SO$_2$Me | Me | I | |
| 2-422 | CH$_2$SO$_2$Me | Et | I | |
| 2-423 | CH$_2$SO$_2$Me | n-Pr | I | |
| 2-424 | CH$_2$SO$_2$Me | i-Pr | I | |
| 2-425 | CH$_2$OCH$_2$CH$_2$OMe | Me | I | |
| 2-426 | CH$_2$OCH$_2$CH$_2$OMe | Et | I | |
| 2-427 | CH$_2$OCH$_2$CH$_2$OMe | n-Pr | I | |
| 2-428 | CH$_2$OCH$_2$CH$_2$OMe | i-Pr | I | |
| 2-429 | CH$_2$OCH$_2$CH$_2$OEt | Me | I | |
| 2-430 | CH$_2$OCH$_2$CH$_2$OEt | Et | I | |
| 2-431 | CH$_2$OCH$_2$CH$_2$OEt | n-Pr | I | |
| 2-432 | CH$_2$OCH$_2$CH$_2$OEt | i-Pr | I | |
| 2-433 | CH$_2$OCH$_2$CH$_2$CH$_2$OMe | Me | I | |
| 2-434 | CH$_2$OCH$_2$CH$_2$CH$_2$OMe | Et | I | |
| 2-435 | CH$_2$OCH$_2$CH$_2$CH$_2$OMe | n-Pr | I | |
| 2-436 | CH$_2$OCH$_2$CH$_2$CH$_2$OMe | i-Pr | I | |
| 2-437 | CH$_2$OCH$_2$OMe | Me | I | |
| 2-438 | CH$_2$OCH$_2$OMe | Et | I | |
| 2-439 | CH$_2$OCH$_2$OMe | n-Pr | I | |
| 2-440 | CH$_2$OCH$_2$OMe | i-Pr | I | |
| 2-441 | CH$_2$OCH$_2$OEt | Me | I | |
| 2-442 | CH$_2$OCH$_2$OEt | Et | I | |
| 2-443 | CH$_2$OCH$_2$OEt | n-Pr | I | |
| 2-444 | CH$_2$OCH$_2$OEt | i-Pr | I | |
| 2-445 | CH$_2$OCH$_2$CH$_2$SO$_2$Me | Me | I | |
| 2-446 | CH$_2$OCH$_2$CH$_2$SO$_2$Me | Et | I | |
| 2-447 | CH$_2$OCH$_2$CH$_2$SO$_2$Me | n-Pr | I | |
| 2-448 | CH$_2$OCH$_2$CH$_2$SO$_2$Me | i-Pr | I | |
| 2-449 | CH$_2$SO$_2$CH$_2$CH$_2$OMe | Me | I | |
| 2-450 | CH$_2$SO$_2$CH$_2$CH$_2$OMe | Et | I | |
| 2-451 | CH$_2$SO$_2$CH$_2$CH$_2$OMe | n-Pr | I | |
| 2-452 | CH$_2$SO$_2$CH$_2$CH$_2$OMe | i-Pr | I | |
| 2-453 | CH$_2$SO$_2$CH$_2$CH$_2$SO$_2$Me | Me | I | |
| 2-454 | CH$_2$SO$_2$CH$_2$CH$_2$SO$_2$Me | Et | I | |
| 2-455 | CH$_2$SO$_2$CH$_2$CH$_2$SO$_2$Me | n-Pr | I | |
| 2-456 | CH$_2$SO$_2$CH$_2$CH$_2$SO$_2$Me | i-Pr | I | |
| 2-457 | Cl | Me | NO$_2$ | |
| 2-458 | Cl | Et | NO$_2$ | |
| 2-459 | Cl | n-Pr | NO$_2$ | |
| 2-460 | Cl | i-Pr | NO$_2$ | |
| 2-461 | Br | Me | NO$_2$ | |
| 2-462 | Br | Et | NO$_2$ | |
| 2-463 | Br | n-Pr | NO$_2$ | |
| 2-464 | Br | i-Pr | NO$_2$ | |
| 2-465 | Me | Me | NO$_2$ | |

TABLE 2-continued

Compounds of the formula (I) according to the invention in which $R^1$ is ethyl, $R^2$ and $R^4$ are each hydrogen.

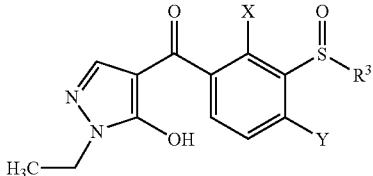

| No. | X | $R^3$ | Y | Physical data: $^1$H-NMR: δ [CDCl$_3$] |
|---|---|---|---|---|
| 2-466 | Me | Et | NO$_2$ | |
| 2-467 | Me | n-Pr | NO$_2$ | |
| 2-468 | Me | i-Pr | NO$_2$ | |
| 2-469 | Et | Me | NO$_2$ | |
| 2-470 | Et | Et | NO$_2$ | |
| 2-471 | Et | n-Pr | NO$_2$ | |
| 2-472 | Et | i-Pr | NO$_2$ | |
| 2-473 | CF$_3$ | Me | NO$_2$ | |
| 2-474 | CF$_3$ | Et | NO$_2$ | |
| 2-475 | CF$_3$ | n-Pr | NO$_2$ | |
| 2-476 | CF$_3$ | i-Pr | NO$_2$ | |
| 2-477 | OMe | Me | NO$_2$ | |
| 2-478 | OMe | Et | NO$_2$ | |
| 2-479 | OMe | n-Pr | NO$_2$ | |
| 2-480 | OMe | i-Pr | NO$_2$ | |
| 2-481 | OEt | Me | NO$_2$ | |
| 2-482 | OEt | Et | NO$_2$ | |
| 2-483 | OEt | n-Pr | NO$_2$ | |
| 2-484 | OEt | i-Pr | NO$_2$ | |
| 2-485 | NO$_2$ | Me | NO$_2$ | |
| 2-486 | NO$_2$ | Et | NO$_2$ | |
| 2-487 | NO$_2$ | n-Pr | NO$_2$ | |
| 2-488 | NO$_2$ | i-Pr | NO$_2$ | |
| 2-489 | SO$_2$Me | Me | NO$_2$ | |
| 2-490 | SO$_2$Me | Et | NO$_2$ | |
| 2-491 | SO$_2$Me | n-Pr | NO$_2$ | |
| 2-492 | SO$_2$Me | i-Pr | NO$_2$ | |
| 2-493 | CH$_2$OMe | Me | NO$_2$ | |
| 2-494 | CH$_2$OMe | Et | NO$_2$ | |
| 2-495 | CH$_2$OMe | n-Pr | NO$_2$ | |
| 2-496 | CH$_2$OMe | i-Pr | NO$_2$ | |
| 2-497 | CH$_2$SO$_2$Me | Me | NO$_2$ | |
| 2-498 | CH$_2$SO$_2$Me | Et | NO$_2$ | |
| 2-499 | CH$_2$SO$_2$Me | n-Pr | NO$_2$ | |
| 2-500 | CH$_2$SO$_2$Me | i-Pr | NO$_2$ | |
| 2-501 | CH$_2$OCH$_2$CH$_2$OMe | Me | NO$_2$ | |
| 2-502 | CH$_2$OCH$_2$CH$_2$OMe | Et | NO$_2$ | |
| 2-503 | CH$_2$OCH$_2$CH$_2$OMe | n-Pr | NO$_2$ | |
| 2-504 | CH$_2$OCH$_2$CH$_2$OMe | i-Pr | NO$_2$ | |
| 2-505 | CH$_2$OCH$_2$CH$_2$OEt | Me | NO$_2$ | |
| 2-506 | CH$_2$OCH$_2$CH$_2$OEt | Et | NO$_2$ | |
| 2-507 | CH$_2$OCH$_2$CH$_2$OEt | n-Pr | NO$_2$ | |
| 2-508 | CH$_2$OCH$_2$CH$_2$OEt | i-Pr | NO$_2$ | |
| 2-509 | CH$_2$OCH$_2$CH$_2$CH$_2$OMe | Me | NO$_2$ | |
| 2-510 | CH$_2$OCH$_2$CH$_2$CH$_2$OMe | Et | NO$_2$ | |
| 2-511 | CH$_2$OCH$_2$CH$_2$CH$_2$OMe | n-Pr | NO$_2$ | |
| 2-512 | CH$_2$OCH$_2$CH$_2$CH$_2$OMe | i-Pr | NO$_2$ | |
| 2-513 | CH$_2$OCH$_2$OMe | Me | NO$_2$ | |
| 2-514 | CH$_2$OCH$_2$OMe | Et | NO$_2$ | |
| 2-515 | CH$_2$OCH$_2$OMe | n-Pr | NO$_2$ | |
| 2-516 | CH$_2$OCH$_2$OMe | i-Pr | NO$_2$ | |
| 2-517 | CH$_2$OCH$_2$OEt | Me | NO$_2$ | |
| 2-518 | CH$_2$OCH$_2$OEt | Et | NO$_2$ | |
| 2-519 | CH$_2$OCH$_2$OEt | n-Pr | NO$_2$ | |
| 2-520 | CH$_2$OCH$_2$OEt | i-Pr | NO$_2$ | |
| 2-521 | CH$_2$OCH$_2$CH$_2$SO$_2$Me | Me | NO$_2$ | |
| 2-522 | CH$_2$OCH$_2$CH$_2$SO$_2$Me | Et | NO$_2$ | |
| 2-523 | CH$_2$OCH$_2$CH$_2$SO$_2$Me | n-Pr | NO$_2$ | |
| 2-524 | CH$_2$OCH$_2$CH$_2$SO$_2$Me | i-Pr | NO$_2$ | |
| 2-525 | CH$_2$SO$_2$CH$_2$CH$_2$OMe | Me | NO$_2$ | |
| 2-526 | CH$_2$SO$_2$CH$_2$CH$_2$OMe | Et | NO$_2$ | |
| 2-527 | CH$_2$SO$_2$CH$_2$CH$_2$OMe | n-Pr | NO$_2$ | |
| 2-528 | CH$_2$SO$_2$CH$_2$CH$_2$OMe | i-Pr | NO$_2$ | |
| 2-529 | CH$_2$SO$_2$CH$_2$CH$_2$SO$_2$Me | Me | NO$_2$ | |
| 2-530 | CH$_2$SO$_2$CH$_2$CH$_2$SO$_2$Me | Et | NO$_2$ | |
| 2-531 | CH$_2$SO$_2$CH$_2$CH$_2$SO$_2$Me | n-Pr | NO$_2$ | |
| 2-532 | CH$_2$SO$_2$CH$_2$CH$_2$SO$_2$Me | i-Pr | NO$_2$ | |

TABLE 3

Compounds of the formula (I) according to the invention in which $R^4$ is hydrogen and $R^1$ and $R^2$ are each methyl.

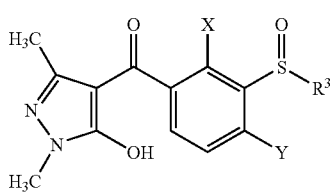

| No. | X | $R^3$ | Y | Physical data: $^1$H-NMR: δ [CDCl$_3$] |
|---|---|---|---|---|
| 3-1 | Cl | Me | SO$_2$Me | |
| 3-2 | Cl | Et | SO$_2$Me | |
| 3-3 | Cl | n-Pr | SO$_2$Me | |
| 3-4 | Cl | i-Pr | SO$_2$Me | |
| 3-5 | Br | Me | SO$_2$Me | |
| 3-6 | Br | Et | SO$_2$Me | |
| 3-7 | Br | n-Pr | SO$_2$Me | |
| 3-8 | Br | i-Pr | SO$_2$Me | |
| 3-9 | Me | Me | SO$_2$Me | 8.09 (d, 1H), 7.49 (d, 1H), 3.64 (s, 3H), 3.38 (s, 3H), 3.18 (s, 3H), 2.81 (s, 3H), 1.69 (s, 3H) |
| 3-10 | Me | Et | SO$_2$Me | |
| 3-11 | Me | n-Pr | SO$_2$Me | |
| 3-12 | Me | i-Pr | SO$_2$Me | |
| 3-13 | Et | Me | SO$_2$Me | |
| 3-14 | Et | Et | SO$_2$Me | |
| 3-15 | Et | n-Pr | SO$_2$Me | |
| 3-16 | Et | i-Pr | SO$_2$Me | |
| 3-17 | CF$_3$ | Me | SO$_2$Me | |
| 3-18 | CF$_3$ | Et | SO$_2$Me | |
| 3-19 | CF$_3$ | n-Pr | SO$_2$Me | |
| 3-20 | CF$_3$ | i-Pr | SO$_2$Me | |
| 3-21 | OMe | Me | SO$_2$Me | |
| 3-22 | OMe | Et | SO$_2$Me | |
| 3-23 | OMe | n-Pr | SO$_2$Me | |
| 3-24 | OMe | i-Pr | SO$_2$Me | |
| 3-25 | OEt | Me | SO$_2$Me | |
| 3-26 | OEt | Et | SO$_2$Me | |
| 3-27 | OEt | n-Pr | SO$_2$Me | |
| 3-28 | OEt | i-Pr | SO$_2$Me | |
| 3-29 | NO$_2$ | Me | SO$_2$Me | |
| 3-30 | NO$_2$ | Et | SO$_2$Me | |
| 3-31 | NO$_2$ | n-Pr | SO$_2$Me | |
| 3-32 | NO$_2$ | i-Pr | SO$_2$Me | |
| 3-33 | SO$_2$Me | Me | SO$_2$Me | |
| 3-34 | SO$_2$Me | Et | SO$_2$Me | |
| 3-35 | SO$_2$Me | n-Pr | SO$_2$Me | |
| 3-36 | SO$_2$Me | i-Pr | SO$_2$Me | |

TABLE 3-continued

Compounds of the formula (I) according to the invention in which $R^4$ is hydrogen and $R^1$ and $R^2$ are each methyl.

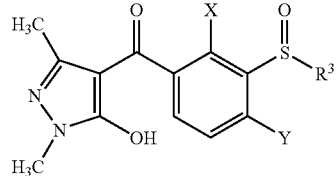

| No. | X | $R^3$ | Y | Physical data: $^1$H-NMR: δ [CDCl$_3$] |
|---|---|---|---|---|
| 3-37 | CH$_2$OMe | Me | SO$_2$Me | |
| 3-38 | CH$_2$OMe | Et | SO$_2$Me | |
| 3-39 | CH$_2$OMe | n-Pr | SO$_2$Me | |
| 3-40 | CH$_2$OMe | i-Pr | SO$_2$Me | |
| 3-41 | CH$_2$SO$_2$Me | Me | SO$_2$Me | |
| 3-42 | CH$_2$SO$_2$Me | Et | SO$_2$Me | |
| 3-43 | CH$_2$SO$_2$Me | n-Pr | SO$_2$Me | |
| 3-44 | CH$_2$SO$_2$Me | i-Pr | SO$_2$Me | |
| 3-45 | CH$_2$OCH$_2$CH$_2$OMe | Me | SO$_2$Me | |
| 3-46 | CH$_2$OCH$_2$CH$_2$OMe | Et | SO$_2$Me | |
| 3-47 | CH$_2$OCH$_2$CH$_2$OMe | n-Pr | SO$_2$Me | |
| 3-48 | CH$_2$OCH$_2$CH$_2$OMe | i-Pr | SO$_2$Me | |
| 3-49 | CH$_2$OCH$_2$CH$_2$OEt | Me | SO$_2$Me | |
| 3-50 | CH$_2$OCH$_2$CH$_2$OEt | Et | SO$_2$Me | |
| 3-51 | CH$_2$OCH$_2$CH$_2$OEt | n-Pr | SO$_2$Me | |
| 3-52 | CH$_2$OCH$_2$CH$_2$OEt | i-Pr | SO$_2$Me | |
| 3-53 | CH$_2$OCH$_2$CH$_2$CH$_2$OMe | Me | SO$_2$Me | |
| 3-54 | CH$_2$OCH$_2$CH$_2$CH$_2$OMe | Et | SO$_2$Me | |
| 3-55 | CH$_2$OCH$_2$CH$_2$CH$_2$OMe | n-Pr | SO$_2$Me | |
| 3-56 | CH$_2$OCH$_2$CH$_2$CH$_2$OMe | i-Pr | SO$_2$Me | |
| 3-57 | CH$_2$OCH$_2$OMe | Me | SO$_2$Me | |
| 3-58 | CH$_2$OCH$_2$OMe | Et | SO$_2$Me | |
| 3-59 | CH$_2$OCH$_2$OMe | n-Pr | SO$_2$Me | |
| 3-60 | CH$_2$OCH$_2$OMe | i-Pr | SO$_2$Me | |
| 3-61 | CH$_2$OCH$_2$OEt | Me | SO$_2$Me | |
| 3-62 | CH$_2$OCH$_2$OEt | Et | SO$_2$Me | |
| 3-63 | CH$_2$OCH$_2$OEt | n-Pr | SO$_2$Me | |
| 3-64 | CH$_2$OCH$_2$OEt | i-Pr | SO$_2$Me | |
| 3-65 | CH$_2$OCH$_2$CH$_2$SO$_2$Me | Me | SO$_2$Me | |
| 3-66 | CH$_2$OCH$_2$CH$_2$SO$_2$Me | Et | SO$_2$Me | |
| 3-67 | CH$_2$OCH$_2$CH$_2$SO$_2$Me | n-Pr | SO$_2$Me | |
| 3-68 | CH$_2$OCH$_2$CH$_2$SO$_2$Me | i-Pr | SO$_2$Me | |
| 3-69 | CH$_2$SO$_2$CH$_2$CH$_2$OMe | Me | SO$_2$Me | |
| 3-70 | CH$_2$SO$_2$CH$_2$CH$_2$OMe | Et | SO$_2$Me | |
| 3-71 | CH$_2$SO$_2$CH$_2$CH$_2$OMe | n-Pr | SO$_2$Me | |
| 3-72 | CH$_2$SO$_2$CH$_2$CH$_2$OMe | i-Pr | SO$_2$Me | |
| 3-73 | CH$_2$SO$_2$CH$_2$CH$_2$SO$_2$Me | Me | SO$_2$Me | |
| 3-74 | CH$_2$SO$_2$CH$_2$CH$_2$SO$_2$Me | Et | SO$_2$Me | |
| 3-75 | CH$_2$SO$_2$CH$_2$CH$_2$SO$_2$Me | n-Pr | SO$_2$Me | |
| 3-76 | CH$_2$SO$_2$CH$_2$CH$_2$SO$_2$Me | i-Pr | SO$_2$Me | |
| 3-77 | Cl | Me | SO$_2$Et | |
| 3-78 | Cl | Et | SO$_2$Et | |
| 3-79 | Cl | n-Pr | SO$_2$Et | |
| 3-80 | Cl | i-Pr | SO$_2$Et | |
| 3-81 | Br | Me | SO$_2$Et | |
| 3-82 | Br | Et | SO$_2$Et | |
| 3-83 | Br | n-Pr | SO$_2$Et | |
| 3-84 | Br | i-Pr | SO$_2$Et | |
| 3-85 | Me | Me | SO$_2$Et | |
| 3-86 | Me | Et | SO$_2$Et | |
| 3-87 | Me | n-Pr | SO$_2$Et | |
| 3-88 | Me | i-Pr | SO$_2$Et | |
| 3-89 | Et | Me | SO$_2$Et | |
| 3-90 | Et | Et | SO$_2$Et | |
| 3-91 | Et | n-Pr | SO$_2$Et | |
| 3-92 | Et | i-Pr | SO$_2$Et | |
| 3-93 | CF$_3$ | Me | SO$_2$Et | |
| 3-94 | CF$_3$ | Et | SO$_2$Et | |
| 3-95 | CF$_3$ | n-Pr | SO$_2$Et | |
| 3-96 | CF$_3$ | i-Pr | SO$_2$Et | |
| 3-97 | OMe | Me | SO$_2$Et | |
| 3-98 | OMe | Et | SO$_2$Et | |
| 3-99 | OMe | n-Pr | SO$_2$Et | |
| 3-100 | OMe | i-Pr | SO$_2$Et | |

TABLE 3-continued

Compounds of the formula (I) according to the invention in which $R^4$ is hydrogen and $R^1$ and $R^2$ are each methyl.

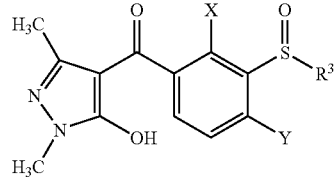

| No. | X | $R^3$ | Y | Physical data: $^1$H-NMR: δ [CDCl$_3$] |
|---|---|---|---|---|
| 3-101 | OEt | Me | SO$_2$Et | |
| 3-102 | OEt | Et | SO$_2$Et | |
| 3-103 | OEt | n-Pr | SO$_2$Et | |
| 3-104 | OEt | i-Pr | SO$_2$Et | |
| 3-105 | NO$_2$ | Me | SO$_2$Et | |
| 3-106 | NO$_2$ | Et | SO$_2$Et | |
| 3-107 | NO$_2$ | n-Pr | SO$_2$Et | |
| 3-108 | NO$_2$ | i-Pr | SO$_2$Et | |
| 3-109 | SO$_2$Me | Me | SO$_2$Et | |
| 3-110 | SO$_2$Me | Et | SO$_2$Et | |
| 3-111 | SO$_2$Me | n-Pr | SO$_2$Et | |
| 3-112 | SO$_2$Me | i-Pr | SO$_2$Et | |
| 3-113 | CH$_2$OMe | Me | SO$_2$Et | |
| 3-114 | CH$_2$OMe | Et | SO$_2$Et | |
| 3-115 | CH$_2$OMe | n-Pr | SO$_2$Et | |
| 3-116 | CH$_2$OMe | i-Pr | SO$_2$Et | |
| 3-117 | CH$_2$SO$_2$Me | Me | SO$_2$Et | |
| 3-118 | CH$_2$SO$_2$Me | Et | SO$_2$Et | |
| 3-119 | CH$_2$SO$_2$Me | n-Pr | SO$_2$Et | |
| 3-120 | CH$_2$SO$_2$Me | i-Pr | SO$_2$Et | |
| 3-121 | CH$_2$OCH$_2$CH$_2$OMe | Me | SO$_2$Et | |
| 3-122 | CH$_2$OCH$_2$CH$_2$OMe | Et | SO$_2$Et | |
| 3-123 | CH$_2$OCH$_2$CH$_2$OMe | n-Pr | SO$_2$Et | |
| 3-124 | CH$_2$OCH$_2$CH$_2$OMe | i-Pr | SO$_2$Et | |
| 3-125 | CH$_2$OCH$_2$CH$_2$OEt | Me | SO$_2$Et | |
| 3-126 | CH$_2$OCH$_2$CH$_2$OEt | Et | SO$_2$Et | |
| 3-127 | CH$_2$OCH$_2$CH$_2$OEt | n-Pr | SO$_2$Et | |
| 3-128 | CH$_2$OCH$_2$CH$_2$OEt | i-Pr | SO$_2$Et | |
| 3-129 | CH$_2$OCH$_2$CH$_2$CH$_2$OMe | Me | SO$_2$Et | |
| 3-130 | CH$_2$OCH$_2$CH$_2$CH$_2$OMe | Et | SO$_2$Et | |
| 3-131 | CH$_2$OCH$_2$CH$_2$CH$_2$OMe | n-Pr | SO$_2$Et | |
| 3-132 | CH$_2$OCH$_2$CH$_2$CH$_2$OMe | i-Pr | SO$_2$Et | |
| 3-133 | CH$_2$OCH$_2$OMe | Me | SO$_2$Et | |
| 3-134 | CH$_2$OCH$_2$OMe | Et | SO$_2$Et | |
| 3-135 | CH$_2$OCH$_2$OMe | n-Pr | SO$_2$Et | |
| 3-136 | CH$_2$OCH$_2$OMe | i-Pr | SO$_2$Et | |
| 3-137 | CH$_2$OCH$_2$OEt | Me | SO$_2$Et | |
| 3-138 | CH$_2$OCH$_2$OEt | Et | SO$_2$Et | |
| 3-139 | CH$_2$OCH$_2$OEt | n-Pr | SO$_2$Et | |
| 3-140 | CH$_2$OCH$_2$OEt | i-Pr | SO$_2$Et | |
| 3-141 | CH$_2$OCH$_2$CH$_2$SO$_2$Me | Me | SO$_2$Et | |
| 3-142 | CH$_2$OCH$_2$CH$_2$SO$_2$Me | Et | SO$_2$Et | |
| 3-143 | CH$_2$OCH$_2$CH$_2$SO$_2$Me | n-Pr | SO$_2$Et | |
| 3-144 | CH$_2$OCH$_2$CH$_2$SO$_2$Me | i-Pr | SO$_2$Et | |
| 3-145 | CH$_2$SO$_2$CH$_2$CH$_2$OMe | Me | SO$_2$Et | |
| 3-146 | CH$_2$SO$_2$CH$_2$CH$_2$OMe | Et | SO$_2$Et | |
| 3-147 | CH$_2$SO$_2$CH$_2$CH$_2$OMe | n-Pr | SO$_2$Et | |
| 3-148 | CH$_2$SO$_2$CH$_2$CH$_2$OMe | i-Pr | SO$_2$Et | |
| 3-149 | CH$_2$SO$_2$CH$_2$CH$_2$SO$_2$Me | Me | SO$_2$Et | |
| 3-150 | CH$_2$SO$_2$CH$_2$CH$_2$SO$_2$Me | Et | SO$_2$Et | |
| 3-151 | CH$_2$SO$_2$CH$_2$CH$_2$SO$_2$Me | n-Pr | SO$_2$Et | |
| 3-152 | CH$_2$SO$_2$CH$_2$CH$_2$SO$_2$Me | i-Pr | SO$_2$Et | |
| 3-153 | Cl | Me | F | |
| 3-154 | Cl | Et | F | |
| 3-155 | Cl | n-Pr | F | |
| 3-156 | Cl | i-Pr | F | |
| 3-157 | Br | Me | F | |
| 3-158 | Br | Et | F | |
| 3-159 | Br | n-Pr | F | |
| 3-160 | Br | i-Pr | F | |
| 3-161 | Me | Me | F | |
| 3-162 | Me | Et | F | |
| 3-163 | Me | n-Pr | F | |
| 3-164 | Me | i-Pr | F | |

TABLE 3-continued

Compounds of the formula (I) according to the invention in which $R^4$ is hydrogen and $R^1$ and $R^2$ are each methyl.

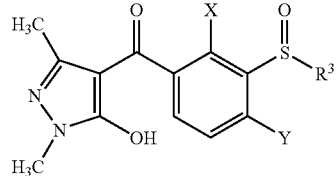

| No. | X | $R^3$ | Y | Physical data: $^1$H-NMR: δ [CDCl$_3$] |
|---|---|---|---|---|
| 3-165 | Et | Me | F | |
| 3-166 | Et | Et | F | |
| 3-167 | Et | n-Pr | F | |
| 3-168 | Et | i-Pr | F | |
| 3-169 | CF$_3$ | Me | F | |
| 3-170 | CF$_3$ | Et | F | |
| 3-171 | CF$_3$ | n-Pr | F | |
| 3-172 | CF$_3$ | i-Pr | F | |
| 3-173 | OMe | Me | F | |
| 3-174 | OMe | Et | F | |
| 3-175 | OMe | n-Pr | F | |
| 3-176 | OMe | i-Pr | F | |
| 3-177 | OEt | Me | F | |
| 3-178 | OEt | Et | F | |
| 3-179 | OEt | n-Pr | F | |
| 3-180 | OEt | i-Pr | F | |
| 3-181 | NO$_2$ | Me | F | |
| 3-182 | NO$_2$ | Et | F | |
| 3-183 | NO$_2$ | n-Pr | F | |
| 3-184 | NO$_2$ | i-Pr | F | |
| 3-185 | SO$_2$Me | Me | F | |
| 3-186 | SO$_2$Me | Et | F | |
| 3-187 | SO$_2$Me | n-Pr | F | |
| 3-188 | SO$_2$Me | i-Pr | F | |
| 3-189 | CH$_2$OMe | Me | F | |
| 3-190 | CH$_2$OMe | Et | F | |
| 3-191 | CH$_2$OMe | n-Pr | F | |
| 3-192 | CH$_2$OMe | i-Pr | F | |
| 3-193 | CH$_2$SO$_2$Me | Me | F | |
| 3-194 | CH$_2$SO$_2$Me | Et | F | |
| 3-195 | CH$_2$SO$_2$Me | n-Pr | F | |
| 3-196 | CH$_2$SO$_2$Me | i-Pr | F | |
| 3-197 | CH$_2$OCH$_2$CH$_2$OMe | Me | F | |
| 3-198 | CH$_2$OCH$_2$CH$_2$OMe | Et | F | |
| 3-199 | CH$_2$OCH$_2$CH$_2$OMe | n-Pr | F | |
| 3-200 | CH$_2$OCH$_2$CH$_2$OMe | i-Pr | F | |
| 3-201 | CH$_2$OCH$_2$CH$_2$OEt | Me | F | |
| 3-202 | CH$_2$OCH$_2$CH$_2$OEt | Et | F | |
| 3-203 | CH$_2$OCH$_2$CH$_2$OEt | n-Pr | F | |
| 3-204 | CH$_2$OCH$_2$CH$_2$OEt | i-Pr | F | |
| 3-205 | CH$_2$OCH$_2$CH$_2$CH$_2$OMe | Me | F | |
| 3-206 | CH$_2$OCH$_2$CH$_2$CH$_2$OMe | Et | F | |
| 3-207 | CH$_2$OCH$_2$CH$_2$CH$_2$OMe | n-Pr | F | |
| 3-208 | CH$_2$OCH$_2$CH$_2$CH$_2$OMe | i-Pr | F | |
| 3-209 | CH$_2$OCH$_2$OMe | Me | F | |
| 3-210 | CH$_2$OCH$_2$OMe | Et | F | |
| 3-211 | CH$_2$OCH$_2$OMe | n-Pr | F | |
| 3-212 | CH$_2$OCH$_2$OMe | i-Pr | F | |
| 3-213 | CH$_2$OCH$_2$OEt | Me | F | |
| 3-214 | CH$_2$OCH$_2$OEt | Et | F | |
| 3-215 | CH$_2$OCH$_2$OEt | n-Pr | F | |
| 3-216 | CH$_2$OCH$_2$OEt | i-Pr | F | |
| 3-217 | CH$_2$OCH$_2$CH$_2$SO$_2$Me | Me | F | |
| 3-218 | CH$_2$OCH$_2$CH$_2$SO$_2$Me | Et | F | |
| 3-219 | CH$_2$OCH$_2$CH$_2$SO$_2$Me | n-Pr | F | |
| 3-220 | CH$_2$OCH$_2$CH$_2$SO$_2$Me | i-Pr | F | |
| 3-221 | CH$_2$SO$_2$CH$_2$CH$_2$OMe | Me | F | |
| 3-222 | CH$_2$SO$_2$CH$_2$CH$_2$OMe | Et | F | |
| 3-223 | CH$_2$SO$_2$CH$_2$CH$_2$OMe | n-Pr | F | |
| 3-224 | CH$_2$SO$_2$CH$_2$CH$_2$OMe | i-Pr | F | |
| 3-225 | CH$_2$SO$_2$CH$_2$CH$_2$SO$_2$Me | Me | F | |
| 3-226 | CH$_2$SO$_2$CH$_2$CH$_2$SO$_2$Me | Et | F | |
| 3-227 | CH$_2$SO$_2$CH$_2$CH$_2$SO$_2$Me | n-Pr | F | |
| 3-228 | CH$_2$SO$_2$CH$_2$CH$_2$SO$_2$Me | i-Pr | F | |

TABLE 3-continued

Compounds of the formula (I) according to the invention in which $R^4$ is hydrogen and $R^1$ and $R^2$ are each methyl.

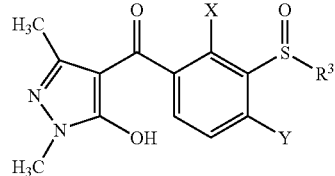

| No. | X | $R^3$ | Y | Physical data: $^1$H-NMR: δ [CDCl$_3$] |
|---|---|---|---|---|
| 3-229 | Cl | Me | Cl | |
| 3-230 | Cl | Et | Cl | |
| 3-231 | Cl | n-Pr | Cl | |
| 3-232 | Cl | i-Pr | Cl | |
| 3-233 | Br | Me | Cl | |
| 3-234 | Br | Et | Cl | |
| 3-235 | Br | n-Pr | Cl | |
| 3-236 | Br | i-Pr | Cl | |
| 3-237 | Me | Me | Cl | 7.37 (d, 1H), 7.23 (d, 1H), 3.63 (s, 3H), 3.01 (s, 3H), 2.68 (s, 3H), 1.72 (s, 3H) |
| 3-238 | Me | Et | Cl | 7.37 (d, 1H), 7.23 (d, 1H), 3.63 (s, 3H), 3.36 (m, 1H), 3.16 (m, 1H), 2.63 (s, 3H), 1.72 (s, 3H), 1.40 (t, 3H) |
| 3-239 | Me | n-Pr | Cl | |
| 3-240 | Me | i-Pr | Cl | |
| 3-241 | Et | Me | Cl | |
| 3-242 | Et | Et | Cl | |
| 3-243 | Et | n-Pr | Cl | |
| 3-244 | Et | i-Pr | Cl | |
| 3-245 | CF$_3$ | Me | Cl | |
| 3-246 | CF$_3$ | Et | Cl | |
| 3-247 | CF$_3$ | n-Pr | Cl | |
| 3-248 | CF$_3$ | i-Pr | Cl | |
| 3-249 | OMe | Me | Cl | |
| 3-250 | OMe | Et | Cl | |
| 3-251 | OMe | n-Pr | Cl | |
| 3-252 | OMe | i-Pr | Cl | |
| 3-253 | OEt | Me | Cl | |
| 3-254 | OEt | Et | Cl | |
| 3-255 | OEt | n-Pr | Cl | |
| 3-256 | OEt | i-Pr | Cl | |
| 3-257 | NO$_2$ | Me | Cl | |
| 3-258 | NO$_2$ | Et | Cl | |
| 3-259 | NO$_2$ | n-Pr | Cl | |
| 3-260 | NO$_2$ | i-Pr | Cl | |
| 3-261 | SO$_2$Me | Me | Cl | |
| 3-262 | SO$_2$Me | Et | Cl | |
| 3-263 | SO$_2$Me | n-Pr | Cl | |
| 3-264 | SO$_2$Me | i-Pr | Cl | |
| 3-265 | CH$_2$OMe | Me | Cl | |
| 3-266 | CH$_2$OMe | Et | Cl | |
| 3-267 | CH$_2$OMe | n-Pr | Cl | |
| 3-268 | CH$_2$OMe | i-Pr | Cl | |
| 3-269 | CH$_2$SO$_2$Me | Me | Cl | |
| 3-270 | CH$_2$SO$_2$Me | Et | Cl | |
| 3-271 | CH$_2$SO$_2$Me | n-Pr | Cl | |
| 3-272 | CH$_2$SO$_2$Me | i-Pr | Cl | |
| 3-273 | CH$_2$OCH$_2$CH$_2$OMe | Me | Cl | |
| 3-274 | CH$_2$OCH$_2$CH$_2$OMe | Et | Cl | |
| 3-275 | CH$_2$OCH$_2$CH$_2$OMe | n-Pr | Cl | |
| 3-276 | CH$_2$OCH$_2$CH$_2$OMe | i-Pr | Cl | |
| 3-277 | CH$_2$OCH$_2$CH$_2$OEt | Me | Cl | |
| 3-278 | CH$_2$OCH$_2$CH$_2$OEt | Et | Cl | |
| 3-279 | CH$_2$OCH$_2$CH$_2$OEt | n-Pr | Cl | |
| 3-280 | CH$_2$OCH$_2$CH$_2$OEt | i-Pr | Cl | |
| 3-281 | CH$_2$OCH$_2$CH$_2$CH$_2$OMe | Me | Cl | |
| 3-282 | CH$_2$OCH$_2$CH$_2$CH$_2$OMe | Et | Cl | |
| 3-283 | CH$_2$OCH$_2$CH$_2$CH$_2$OMe | n-Pr | Cl | |
| 3-284 | CH$_2$OCH$_2$CH$_2$CH$_2$OMe | i-Pr | Cl | |
| 3-285 | CH$_2$OCH$_2$OMe | Me | Cl | |

TABLE 3-continued

Compounds of the formula (I) according to the invention in which $R^4$ is hydrogen and $R^1$ and $R^2$ are each methyl.

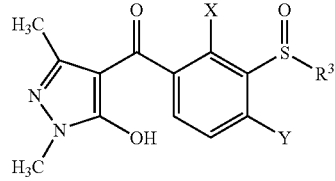

| No. | X | $R^3$ | Y | Physical data: $^1$H-NMR: δ [CDCl$_3$] |
|---|---|---|---|---|
| 3-286 | CH$_2$OCH$_2$OMe | Et | Cl | |
| 3-287 | CH$_2$OCH$_2$OMe | n-Pr | Cl | |
| 3-288 | CH$_2$OCH$_2$OMe | i-Pr | Cl | |
| 3-289 | CH$_2$OCH$_2$OEt | Me | Cl | |
| 3-290 | CH$_2$OCH$_2$OEt | Et | Cl | |
| 3-291 | CH$_2$OCH$_2$OEt | n-Pr | Cl | |
| 3-292 | CH$_2$OCH$_2$OEt | i-Pr | Cl | |
| 3-293 | CH$_2$OCH$_2$CH$_2$SO$_2$Me | Me | Cl | |
| 3-294 | CH$_2$OCH$_2$CH$_2$SO$_2$Me | Et | Cl | |
| 3-295 | CH$_2$OCH$_2$CH$_2$SO$_2$Me | n-Pr | Cl | |
| 3-296 | CH$_2$OCH$_2$CH$_2$SO$_2$Me | i-Pr | Cl | |
| 3-297 | CH$_2$SO$_2$CH$_2$CH$_2$OMe | Me | Cl | |
| 3-298 | CH$_2$SO$_2$CH$_2$CH$_2$OMe | Et | Cl | |
| 3-299 | CH$_2$SO$_2$CH$_2$CH$_2$OMe | n-Pr | Cl | |
| 3-300 | CH$_2$SO$_2$CH$_2$CH$_2$OMe | i-Pr | Cl | |
| 3-301 | CH$_2$SO$_2$CH$_2$CH$_2$SO$_2$Me | Me | Cl | |
| 3-302 | CH$_2$SO$_2$CH$_2$CH$_2$SO$_2$Me | Et | Cl | |
| 3-303 | CH$_2$SO$_2$CH$_2$CH$_2$SO$_2$Me | n-Pr | Cl | |
| 3-304 | CH$_2$SO$_2$CH$_2$CH$_2$SO$_2$Me | i-Pr | Cl | |
| 3-305 | Cl | Me | Br | |
| 3-306 | Cl | Et | Br | |
| 3-307 | Cl | n-Pr | Br | |
| 3-308 | Cl | i-Pr | Br | |
| 3-309 | Br | Me | Br | |
| 3-310 | Br | Et | Br | |
| 3-311 | Br | n-Pr | Br | |
| 3-312 | Br | i-Pr | Br | |
| 3-313 | Me | Me | Br | 7.57 (d, 1H), 7.16 (d, 1H), 3.67 (s, 3H), 3.02 (s, 3H), 2.69 (s, 3H), 1.75 (s, 3H) |
| 3-314 | Me | Et | Br | |
| 3-315 | Me | n-Pr | Br | |
| 3-316 | Me | i-Pr | Br | |
| 3-317 | Et | Me | Br | |
| 3-318 | Et | Et | Br | |
| 3-319 | Et | n-Pr | Br | |
| 3-320 | Et | i-Pr | Br | |
| 3-321 | CF$_3$ | Me | Br | |
| 3-322 | CF$_3$ | Et | Br | |
| 3-323 | CF$_3$ | n-Pr | Br | |
| 3-324 | CF$_3$ | i-Pr | Br | |
| 3-325 | OMe | Me | Br | |
| 3-326 | OMe | Et | Br | |
| 3-327 | OMe | n-Pr | Br | |
| 3-328 | OMe | i-Pr | Br | |
| 3-329 | OEt | Me | Br | |
| 3-330 | OEt | Et | Br | |
| 3-331 | OEt | n-Pr | Br | |
| 3-332 | OEt | i-Pr | Br | |
| 3-333 | NO$_2$ | Me | Br | |
| 3-334 | NO$_2$ | Et | Br | |
| 3-335 | NO$_2$ | n-Pr | Br | |
| 3-336 | NO$_2$ | i-Pr | Br | |
| 3-337 | SO$_2$Me | Me | Br | |
| 3-338 | SO$_2$Me | Et | Br | |
| 3-339 | SO$_2$Me | n-Pr | Br | |
| 3-340 | SO$_2$Me | i-Pr | Br | |
| 3-341 | CH$_2$OMe | Me | Br | |
| 3-342 | CH$_2$OMe | Et | Br | |
| 3-343 | CH$_2$OMe | n-Pr | Br | |
| 3-344 | CH$_2$OMe | i-Pr | Br | |
| 3-345 | CH$_2$SO$_2$Me | Me | Br | |
| 3-346 | CH$_2$SO$_2$Me | Et | Br | |

TABLE 3-continued

Compounds of the formula (I) according to the invention in which $R^4$ is hydrogen and $R^1$ and $R^2$ are each methyl.

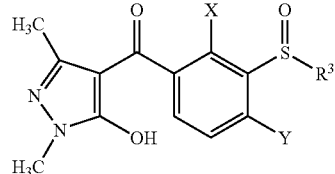

| No. | X | $R^3$ | Y | Physical data: $^1$H-NMR: δ [CDCl$_3$] |
|---|---|---|---|---|
| 3-347 | CH$_2$SO$_2$Me | n-Pr | Br | |
| 3-348 | CH$_2$SO$_2$Me | i-Pr | Br | |
| 3-349 | CH$_2$OCH$_2$CH$_2$OMe | Me | Br | |
| 3-350 | CH$_2$OCH$_2$CH$_2$OMe | Et | Br | |
| 3-351 | CH$_2$OCH$_2$CH$_2$OMe | n-Pr | Br | |
| 3-352 | CH$_2$OCH$_2$CH$_2$OMe | i-Pr | Br | |
| 3-353 | CH$_2$OCH$_2$CH$_2$OEt | Me | Br | |
| 3-354 | CH$_2$OCH$_2$CH$_2$OEt | Et | Br | |
| 3-355 | CH$_2$OCH$_2$CH$_2$OEt | n-Pr | Br | |
| 3-356 | CH$_2$OCH$_2$CH$_2$OEt | i-Pr | Br | |
| 3-357 | CH$_2$OCH$_2$CH$_2$CH$_2$OMe | Me | Br | |
| 3-358 | CH$_2$OCH$_2$CH$_2$CH$_2$OMe | Et | Br | |
| 3-359 | CH$_2$OCH$_2$CH$_2$CH$_2$OMe | n-Pr | Br | |
| 3-360 | CH$_2$OCH$_2$CH$_2$CH$_2$OMe | i-Pr | Br | |
| 3-361 | CH$_2$OCH$_2$OMe | Me | Br | |
| 3-362 | CH$_2$OCH$_2$OMe | Et | Br | |
| 3-363 | CH$_2$OCH$_2$OMe | n-Pr | Br | |
| 3-364 | CH$_2$OCH$_2$OMe | i-Pr | Br | |
| 3-365 | CH$_2$OCH$_2$OEt | Me | Br | |
| 3-366 | CH$_2$OCH$_2$OEt | Et | Br | |
| 3-367 | CH$_2$OCH$_2$OEt | n-Pr | Br | |
| 3-368 | CH$_2$OCH$_2$OEt | i-Pr | Br | |
| 3-369 | CH$_2$OCH$_2$CH$_2$SO$_2$Me | Me | Br | |
| 3-370 | CH$_2$OCH$_2$CH$_2$SO$_2$Me | Et | Br | |
| 3-371 | CH$_2$OCH$_2$CH$_2$SO$_2$Me | n-Pr | Br | |
| 3-372 | CH$_2$OCH$_2$CH$_2$SO$_2$Me | i-Pr | Br | |
| 3-373 | CH$_2$SO$_2$CH$_2$CH$_2$OMe | Me | Br | |
| 3-374 | CH$_2$SO$_2$CH$_2$CH$_2$OMe | Et | Br | |
| 3-375 | CH$_2$SO$_2$CH$_2$CH$_2$OMe | n-Pr | Br | |
| 3-376 | CH$_2$SO$_2$CH$_2$CH$_2$OMe | i-Pr | Br | |
| 3-377 | CH$_2$SO$_2$CH$_2$CH$_2$SO$_2$Me | Me | Br | |
| 3-378 | CH$_2$SO$_2$CH$_2$CH$_2$SO$_2$Me | Et | Br | |
| 3-379 | CH$_2$SO$_2$CH$_2$CH$_2$SO$_2$Me | n-Pr | Br | |
| 3-380 | CH$_2$SO$_2$CH$_2$CH$_2$SO$_2$Me | i-Pr | Br | |
| 3-381 | Cl | Me | I | |
| 3-382 | Cl | Et | I | |
| 3-383 | Cl | n-Pr | I | |
| 3-384 | Cl | i-Pr | I | |
| 3-385 | Br | Me | I | |
| 3-386 | Br | Et | I | |
| 3-387 | Br | n-Pr | I | |
| 3-388 | Br | i-Pr | I | |
| 3-389 | Me | Me | I | 7.68 (d, 1H), 6.96 (d, 1H), 3.65 (s, 3H), 2.96 (s, 3H), 2.68 (s, 3H), 1.74 (s, 3H) |
| 3-390 | Me | Et | I | |
| 3-391 | Me | n-Pr | I | |
| 3-392 | Me | i-Pr | I | |
| 3-393 | Et | Me | I | |
| 3-394 | Et | Et | I | |
| 3-395 | Et | n-Pr | I | |
| 3-396 | Et | i-Pr | I | |
| 3-397 | CF$_3$ | Me | I | |
| 3-398 | CF$_3$ | Et | I | |
| 3-399 | CF$_3$ | n-Pr | I | |
| 3-400 | CF$_3$ | i-Pr | I | |
| 3-401 | OMe | Me | I | |
| 3-402 | OMe | Et | I | |
| 3-403 | OMe | n-Pr | I | |
| 3-404 | OMe | i-Pr | I | |
| 3-405 | OEt | Me | I | |
| 3-406 | OEt | Et | I | |
| 3-407 | OEt | n-Pr | I | |

TABLE 3-continued

Compounds of the formula (I) according to the invention in which $R^4$ is hydrogen and $R^1$ and $R^2$ are each methyl.

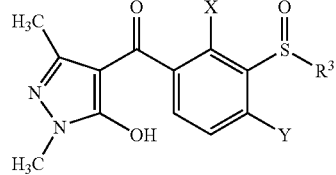

| No. | X | $R^3$ | Y | Physical data: $^1$H-NMR: δ [CDCl$_3$] |
|---|---|---|---|---|
| 3-408 | OEt | i-Pr | I | |
| 3-409 | NO$_2$ | Me | I | |
| 3-410 | NO$_2$ | Et | I | |
| 3-411 | NO$_2$ | n-Pr | I | |
| 3-412 | NO$_2$ | i-Pr | I | |
| 3-413 | SO$_2$Me | Me | I | |
| 3-414 | SO$_2$Me | Et | I | |
| 3-415 | SO$_2$Me | n-Pr | I | |
| 3-416 | SO$_2$Me | i-Pr | I | |
| 3-417 | CH$_2$OMe | Me | I | |
| 3-418 | CH$_2$OMe | Et | I | |
| 3-419 | CH$_2$OMe | n-Pr | I | |
| 3-420 | CH$_2$OMe | i-Pr | I | |
| 3-421 | CH$_2$SO$_2$Me | Me | I | |
| 3-422 | CH$_2$SO$_2$Me | Et | I | |
| 3-423 | CH$_2$SO$_2$Me | n-Pr | I | |
| 3-424 | CH$_2$SO$_2$Me | i-Pr | I | |
| 3-425 | CH$_2$OCH$_2$CH$_2$OMe | Me | I | |
| 3-426 | CH$_2$OCH$_2$CH$_2$OMe | Et | I | |
| 3-427 | CH$_2$OCH$_2$CH$_2$OMe | n-Pr | I | |
| 3-428 | CH$_2$OCH$_2$CH$_2$OMe | i-Pr | I | |
| 3-429 | CH$_2$OCH$_2$CH$_2$OEt | Me | I | |
| 3-430 | CH$_2$OCH$_2$CH$_2$OEt | Et | I | |
| 3-431 | CH$_2$OCH$_2$CH$_2$OEt | n-Pr | I | |
| 3-432 | CH$_2$OCH$_2$CH$_2$OEt | i-Pr | I | |
| 3-433 | CH$_2$OCH$_2$CH$_2$CH$_2$OMe | Me | I | |
| 3-434 | CH$_2$OCH$_2$CH$_2$CH$_2$OMe | Et | I | |
| 3-435 | CH$_2$OCH$_2$CH$_2$CH$_2$OMe | n-Pr | I | |
| 3-436 | CH$_2$OCH$_2$CH$_2$CH$_2$OMe | i-Pr | I | |
| 3-437 | CH$_2$OCH$_2$OMe | Me | I | |
| 3-438 | CH$_2$OCH$_2$OMe | Et | I | |
| 3-439 | CH$_2$OCH$_2$OMe | n-Pr | I | |
| 3-440 | CH$_2$OCH$_2$OMe | i-Pr | I | |
| 3-441 | CH$_2$OCH$_2$OEt | Me | I | |
| 3-442 | CH$_2$OCH$_2$OEt | Et | I | |
| 3-443 | CH$_2$OCH$_2$OEt | n-Pr | I | |
| 3-444 | CH$_2$OCH$_2$OEt | i-Pr | I | |
| 3-445 | CH$_2$OCH$_2$CH$_2$SO$_2$Me | Me | I | |
| 3-446 | CH$_2$OCH$_2$CH$_2$SO$_2$Me | Et | I | |
| 3-447 | CH$_2$OCH$_2$CH$_2$SO$_2$Me | n-Pr | I | |
| 3-448 | CH$_2$OCH$_2$CH$_2$SO$_2$Me | i-Pr | I | |
| 3-449 | CH$_2$SO$_2$CH$_2$CH$_2$OMe | Me | I | |
| 3-450 | CH$_2$SO$_2$CH$_2$CH$_2$OMe | Et | I | |
| 3-451 | CH$_2$SO$_2$CH$_2$CH$_2$OMe | n-Pr | I | |
| 3-452 | CH$_2$SO$_2$CH$_2$CH$_2$OMe | i-Pr | I | |
| 3-453 | CH$_2$SO$_2$CH$_2$CH$_2$SO$_2$Me | Me | I | |
| 3-454 | CH$_2$SO$_2$CH$_2$CH$_2$SO$_2$Me | Et | I | |
| 3-455 | CH$_2$SO$_2$CH$_2$CH$_2$SO$_2$Me | n-Pr | I | |
| 3-456 | CH$_2$SO$_2$CH$_2$CH$_2$SO$_2$Me | i-Pr | I | |
| 3-457 | Cl | Me | NO$_2$ | |
| 3-458 | Cl | Et | NO$_2$ | |
| 3-459 | Cl | n-Pr | NO$_2$ | |
| 3-460 | Cl | i-Pr | NO$_2$ | |
| 3-461 | Br | Me | NO$_2$ | |
| 3-462 | Br | Et | NO$_2$ | |
| 3-463 | Br | n-Pr | NO$_2$ | |
| 3-464 | Br | i-Pr | NO$_2$ | |
| 3-465 | Me | Me | NO$_2$ | |
| 3-466 | Me | Et | NO$_2$ | |
| 3-467 | Me | n-Pr | NO$_2$ | |
| 3-468 | Me | i-Pr | NO$_2$ | |
| 3-469 | Et | Me | NO$_2$ | |
| 3-470 | Et | Et | NO$_2$ | |
| 3-471 | Et | n-Pr | NO$_2$ | |

TABLE 3-continued

Compounds of the formula (I) according to the invention in which $R^4$ is hydrogen and $R^1$ and $R^2$ are each methyl.

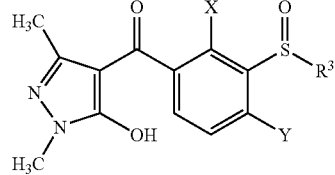

| No. | X | $R^3$ | Y | Physical data: $^1$H-NMR: δ [CDCl$_3$] |
|---|---|---|---|---|
| 3-472 | Et | i-Pr | NO$_2$ | |
| 3-473 | CF$_3$ | Me | NO$_2$ | |
| 3-474 | CF$_3$ | Et | NO$_2$ | |
| 3-475 | CF$_3$ | n-Pr | NO$_2$ | |
| 3-476 | CF$_3$ | i-Pr | NO$_2$ | |
| 3-477 | OMe | Me | NO$_2$ | |
| 3-478 | OMe | Et | NO$_2$ | |
| 3-479 | OMe | n-Pr | NO$_2$ | |
| 3-480 | OMe | i-Pr | NO$_2$ | |
| 3-481 | OEt | Me | NO$_2$ | |
| 3-482 | OEt | Et | NO$_2$ | |
| 3-483 | OEt | n-Pr | NO$_2$ | |
| 3-484 | OEt | i-Pr | NO$_2$ | |
| 3-485 | NO$_2$ | Me | NO$_2$ | |
| 3-486 | NO$_2$ | Et | NO$_2$ | |
| 3-487 | NO$_2$ | n-Pr | NO$_2$ | |
| 3-488 | NO$_2$ | i-Pr | NO$_2$ | |
| 3-489 | SO$_2$Me | Me | NO$_2$ | |
| 3-490 | SO$_2$Me | Et | NO$_2$ | |
| 3-491 | SO$_2$Me | n-Pr | NO$_2$ | |
| 3-492 | SO$_2$Me | i-Pr | NO$_2$ | |
| 3-493 | CH$_2$OMe | Me | NO$_2$ | |
| 3-494 | CH$_2$OMe | Et | NO$_2$ | |
| 3-495 | CH$_2$OMe | n-Pr | NO$_2$ | |
| 3-496 | CH$_2$OMe | i-Pr | NO$_2$ | |
| 3-497 | CH$_2$SO$_2$Me | Me | NO$_2$ | |
| 3-498 | CH$_2$SO$_2$Me | Et | NO$_2$ | |
| 3-499 | CH$_2$SO$_2$Me | n-Pr | NO$_2$ | |
| 3-500 | CH$_2$SO$_2$Me | i-Pr | NO$_2$ | |
| 3-501 | CH$_2$OCH$_2$CH$_2$OMe | Me | NO$_2$ | |
| 3-502 | CH$_2$OCH$_2$CH$_2$OMe | Et | NO$_2$ | |
| 3-503 | CH$_2$OCH$_2$CH$_2$OMe | n-Pr | NO$_2$ | |
| 3-504 | CH$_2$OCH$_2$CH$_2$OMe | i-Pr | NO$_2$ | |
| 3-505 | CH$_2$OCH$_2$CH$_2$OEt | Me | NO$_2$ | |
| 3-506 | CH$_2$OCH$_2$CH$_2$OEt | Et | NO$_2$ | |
| 3-507 | CH$_2$OCH$_2$CH$_2$OEt | n-Pr | NO$_2$ | |
| 3-508 | CH$_2$OCH$_2$CH$_2$OEt | i-Pr | NO$_2$ | |
| 3-509 | CH$_2$OCH$_2$CH$_2$CH$_2$OMe | Me | NO$_2$ | |
| 3-510 | CH$_2$OCH$_2$CH$_2$CH$_2$OMe | Et | NO$_2$ | |
| 3-511 | CH$_2$OCH$_2$CH$_2$CH$_2$OMe | n-Pr | NO$_2$ | |
| 3-512 | CH$_2$OCH$_2$CH$_2$CH$_2$OMe | i-Pr | NO$_2$ | |
| 3-513 | CH$_2$OCH$_2$OMe | Me | NO$_2$ | |
| 3-514 | CH$_2$OCH$_2$OMe | Et | NO$_2$ | |
| 3-515 | CH$_2$OCH$_2$OMe | n-Pr | NO$_2$ | |
| 3-516 | CH$_2$OCH$_2$OMe | i-Pr | NO$_2$ | |
| 3-517 | CH$_2$OCH$_2$OEt | Me | NO$_2$ | |
| 3-518 | CH$_2$OCH$_2$OEt | Et | NO$_2$ | |
| 3-519 | CH$_2$OCH$_2$OEt | n-Pr | NO$_2$ | |
| 3-520 | CH$_2$OCH$_2$OEt | i-Pr | NO$_2$ | |
| 3-521 | CH$_2$OCH$_2$CH$_2$SO$_2$Me | Me | NO$_2$ | |
| 3-522 | CH$_2$OCH$_2$CH$_2$SO$_2$Me | Et | NO$_2$ | |
| 3-523 | CH$_2$OCH$_2$CH$_2$SO$_2$Me | n-Pr | NO$_2$ | |
| 3-524 | CH$_2$OCH$_2$CH$_2$SO$_2$Me | i-Pr | NO$_2$ | |
| 3-525 | CH$_2$SO$_2$CH$_2$CH$_2$OMe | Me | NO$_2$ | |
| 3-526 | CH$_2$SO$_2$CH$_2$CH$_2$OMe | Et | NO$_2$ | |
| 3-527 | CH$_2$SO$_2$CH$_2$CH$_2$OMe | n-Pr | NO$_2$ | |
| 3-528 | CH$_2$SO$_2$CH$_2$CH$_2$OMe | i-Pr | NO$_2$ | |
| 3-529 | CH$_2$SO$_2$CH$_2$CH$_2$SO$_2$Me | Me | NO$_2$ | |
| 3-530 | CH$_2$SO$_2$CH$_2$CH$_2$SO$_2$Me | Et | NO$_2$ | |
| 3-531 | CH$_2$SO$_2$CH$_2$CH$_2$SO$_2$Me | n-Pr | NO$_2$ | |
| 3-532 | CH$_2$SO$_2$CH$_2$CH$_2$SO$_2$Me | i-Pr | NO$_2$ | |

TABLE 4

Compounds of the formula (II) according to the invention

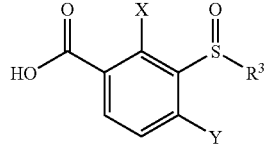
(II)

| No. | X | R³ | Y | Physical data: ¹H-NMR: δ [CDCl₃] |
|---|---|---|---|---|
| 4-1 | Cl | Me | SO₂Me | |
| 4-2 | Cl | Et | SO₂Me | |
| 4-3 | Cl | n-Pr | SO₂Me | |
| 4-4 | Cl | i-Pr | SO₂Me | |
| 4-5 | Br | Me | SO₂Me | |
| 4-6 | Br | Et | SO₂Me | |
| 4-7 | Br | n-Pr | SO₂Me | |
| 4-8 | Br | i-Pr | SO₂Me | |
| 4-9 | Me | Me | SO₂Me | (DMSO-d₆): 7.93 (s, 2H), 3.46 (s, 3H), 3.08 (s, 3H), 2.87 (s, 3H) |
| 4-10 | Me | Et | SO₂Me | (DMSO-d₆): 7.93 (s, 2H), 3.47 (m, 1H), 3.46 (s, 3H), 3.08 (m, 1H), 2.82 (s, 3H), 1.33 (t, 3H) |
| 4-11 | Me | n-Pr | SO₂Me | |
| 4-12 | Me | i-Pr | SO₂Me | |
| 4-13 | Et | Me | SO₂Me | |
| 4-14 | Et | Et | SO₂Me | |
| 4-15 | Et | n-Pr | SO₂Me | |
| 4-16 | Et | i-Pr | SO₂Me | |
| 4-17 | CF₃ | Me | SO₂Me | |
| 4-18 | CF₃ | Et | SO₂Me | |
| 4-19 | CF₃ | n-Pr | SO₂Me | |
| 4-20 | CF₃ | i-Pr | SO₂Me | |
| 4-21 | OMe | Me | SO₂Me | |
| 4-22 | OMe | Et | SO₂Me | |
| 4-23 | OMe | n-Pr | SO₂Me | |
| 4-24 | OMe | i-Pr | SO₂Me | |
| 4-25 | OEt | Me | SO₂Me | |
| 4-26 | OEt | Et | SO₂Me | |
| 4-27 | OEt | n-Pr | SO₂Me | |
| 4-28 | OEt | i-Pr | SO₂Me | |
| 4-29 | NO₂ | Me | SO₂Me | |
| 4-30 | NO₂ | Et | SO₂Me | |
| 4-31 | NO₂ | n-Pr | SO₂Me | |
| 4-32 | NO₂ | i-Pr | SO₂Me | |
| 4-33 | SO₂Me | Me | SO₂Me | |
| 4-34 | SO₂Me | Et | SO₂Me | |
| 4-35 | SO₂Me | n-Pr | SO₂Me | |
| 4-36 | SO₂Me | i-Pr | SO₂Me | |
| 4-37 | CH₂OMe | Me | SO₂Me | |
| 4-38 | CH₂OMe | Et | SO₂Me | |
| 4-39 | CH₂OMe | n-Pr | SO₂Me | |
| 4-40 | CH₂OMe | i-Pr | SO₂Me | |
| 4-41 | CH₂SO₂Me | Me | SO₂Me | |
| 4-42 | CH₂SO₂Me | Et | SO₂Me | |
| 4-43 | CH₂SO₂Me | n-Pr | SO₂Me | |
| 4-44 | CH₂SO₂Me | i-Pr | SO₂Me | |
| 4-45 | CH₂OCH₂CH₂OMe | Me | SO₂Me | |
| 4-46 | CH₂OCH₂CH₂OMe | Et | SO₂Me | |
| 4-47 | CH₂OCH₂CH₂OMe | n-Pr | SO₂Me | |
| 4-48 | CH₂OCH₂CH₂OMe | i-Pr | SO₂Me | |
| 4-49 | CH₂OCH₂CH₂OEt | Me | SO₂Me | |
| 4-50 | CH₂OCH₂CH₂OEt | Et | SO₂Me | |
| 4-51 | CH₂OCH₂CH₂OEt | n-Pr | SO₂Me | |
| 4-52 | CH₂OCH₂CH₂OEt | i-Pr | SO₂Me | |
| 4-53 | CH₂OCH₂CH₂CH₂OMe | Me | SO₂Me | |
| 4-54 | CH₂OCH₂CH₂CH₂OMe | Et | SO₂Me | |
| 4-55 | CH₂OCH₂CH₂CH₂OMe | n-Pr | SO₂Me | |
| 4-56 | CH₂OCH₂CH₂CH₂OMe | i-Pr | SO₂Me | |
| 4-57 | CH₂OCH₂OMe | Me | SO₂Me | |
| 4-58 | CH₂OCH₂OMe | Et | SO₂Me | |
| 4-59 | CH₂OCH₂OMe | n-Pr | SO₂Me | |
| 4-60 | CH₂OCH₂OMe | i-Pr | SO₂Me | |
| 4-61 | CH₂OCH₂OEt | Me | SO₂Me | |
| 4-62 | CH₂OCH₂OEt | Et | SO₂Me | |
| 4-63 | CH₂OCH₂OEt | n-Pr | SO₂Me | |

TABLE 4-continued

Compounds of the formula (II) according to the invention $$\text{(II)}$$

| No. | X | R³ | Y | Physical data: ¹H-NMR: δ [CDCl₃] |
|---|---|---|---|---|
| 4-64 | CH₂OCH₂OEt | i-Pr | SO₂Me | |
| 4-65 | CH₂OCH₂CH₂SO₂Me | Me | SO₂Me | |
| 4-66 | CH₂OCH₂CH₂SO₂Me | Et | SO₂Me | |
| 4-67 | CH₂OCH₂CH₂SO₂Me | n-Pr | SO₂Me | |
| 4-68 | CH₂OCH₂CH₂SO₂Me | i-Pr | SO₂Me | |
| 4-69 | CH₂SO₂CH₂CH₂OMe | Me | SO₂Me | |
| 4-70 | CH₂SO₂CH₂CH₂OMe | Et | SO₂Me | |
| 4-71 | CH₂SO₂CH₂CH₂OMe | n-Pr | SO₂Me | |
| 4-72 | CH₂SO₂CH₂CH₂OMe | i-Pr | SO₂Me | |
| 4-73 | CH₂SO₂CH₂CH₂SO₂Me | Me | SO₂Me | |
| 4-74 | CH₂SO₂CH₂CH₂SO₂Me | Et | SO₂Me | |
| 4-75 | CH₂SO₂CH₂CH₂SO₂Me | n-Pr | SO₂Me | |
| 4-76 | CH₂SO₂CH₂CH₂SO₂Me | i-Pr | SO₂Me | |
| 4-77 | Cl | Me | SO₂Et | |
| 4-78 | Cl | Et | SO₂Et | |
| 4-79 | Cl | n-Pr | SO₂Et | |
| 4-80 | Cl | i-Pr | SO₂Et | |
| 4-81 | Br | Me | SO₂Et | |
| 4-82 | Br | Et | SO₂Et | |
| 4-83 | Br | n-Pr | SO₂Et | |
| 4-84 | Br | i-Pr | SO₂Et | |
| 4-85 | Me | Me | SO₂Et | |
| 4-86 | Me | Et | SO₂Et | |
| 4-87 | Me | n-Pr | SO₂Et | |
| 4-88 | Me | i-Pr | SO₂Et | |
| 4-89 | Et | Me | SO₂Et | |
| 4-90 | Et | Et | SO₂Et | |
| 4-91 | Et | n-Pr | SO₂Et | |
| 4-92 | Et | i-Pr | SO₂Et | |
| 4-93 | CF₃ | Me | SO₂Et | |
| 4-94 | CF₃ | Et | SO₂Et | |
| 4-95 | CF₃ | n-Pr | SO₂Et | |
| 4-96 | CF₃ | i-Pr | SO₂Et | |
| 4-97 | OMe | Me | SO₂Et | |
| 4-98 | OMe | Et | SO₂Et | |
| 4-99 | OMe | n-Pr | SO₂Et | |
| 4-100 | OMe | i-Pr | SO₂Et | |
| 4-101 | OEt | Me | SO₂Et | |
| 4-102 | OEt | Et | SO₂Et | |
| 4-103 | OEt | n-Pr | SO₂Et | |
| 4-104 | OEt | i-Pr | SO₂Et | |
| 4-105 | NO₂ | Me | SO₂Et | |
| 4-106 | NO₂ | Et | SO₂Et | |
| 4-107 | NO₂ | n-Pr | SO₂Et | |
| 4-108 | NO₂ | i-Pr | SO₂Et | |
| 4-109 | SO₂Me | Me | SO₂Et | |
| 4-110 | SO₂Me | Et | SO₂Et | |
| 4-111 | SO₂Me | n-Pr | SO₂Et | |
| 4-112 | SO₂Me | i-Pr | SO₂Et | |
| 4-113 | CH₂OMe | Me | SO₂Et | |
| 4-114 | CH₂OMe | Et | SO₂Et | |
| 4-115 | CH₂OMe | n-Pr | SO₂Et | |
| 4-116 | CH₂OMe | i-Pr | SO₂Et | |
| 4-117 | CH₂SO₂Me | Me | SO₂Et | |
| 4-118 | CH₂SO₂Me | Et | SO₂Et | |
| 4-119 | CH₂SO₂Me | n-Pr | SO₂Et | |
| 4-120 | CH₂SO₂Me | i-Pr | SO₂Et | |
| 4-121 | CH₂OCH₂CH₂OMe | Me | SO₂Et | |
| 4-122 | CH₂OCH₂CH₂OMe | Et | SO₂Et | |
| 4-123 | CH₂OCH₂CH₂OMe | n-Pr | SO₂Et | |
| 4-124 | CH₂OCH₂CH₂OMe | i-Pr | SO₂Et | |
| 4-125 | CH₂OCH₂CH₂OEt | Me | SO₂Et | |
| 4-126 | CH₂OCH₂CH₂OEt | Et | SO₂Et | |
| 4-127 | CH₂OCH₂CH₂OEt | n-Pr | SO₂Et | |
| 4-128 | CH₂OCH₂CH₂OEt | i-Pr | SO₂Et | |
| 4-129 | CH₂OCH₂CH₂CH₂OMe | Me | SO₂Et | |

TABLE 4-continued

Compounds of the formula (II) according to the invention

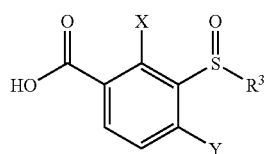

(II)

| No. | X | R³ | Y | Physical data: ¹H-NMR: δ [CDCl₃] |
|---|---|---|---|---|
| 4-130 | CH₂OCH₂CH₂CH₂OMe | Et | SO₂Et | |
| 4-131 | CH₂OCH₂CH₂CH₂OMe | n-Pr | SO₂Et | |
| 4-132 | CH₂OCH₂CH₂CH₂OMe | i-Pr | SO₂Et | |
| 4-133 | CH₂OCH₂OMe | Me | SO₂Et | |
| 4-134 | CH₂OCH₂OMe | Et | SO₂Et | |
| 4-135 | CH₂OCH₂OMe | n-Pr | SO₂Et | |
| 4-136 | CH₂OCH₂OMe | i-Pr | SO₂Et | |
| 4-137 | CH₂OCH₂OEt | Me | SO₂Et | |
| 4-138 | CH₂OCH₂OEt | Et | SO₂Et | |
| 4-139 | CH₂OCH₂OEt | n-Pr | SO₂Et | |
| 4-140 | CH₂OCH₂OEt | i-Pr | SO₂Et | |
| 4-141 | CH₂OCH₂CH₂SO₂Me | Me | SO₂Et | |
| 4-142 | CH₂OCH₂CH₂SO₂Me | Et | SO₂Et | |
| 4-143 | CH₂OCH₂CH₂SO₂Me | n-Pr | SO₂Et | |
| 4-144 | CH₂OCH₂CH₂SO₂Me | i-Pr | SO₂Et | |
| 4-145 | CH₂SO₂CH₂CH₂OMe | Me | SO₂Et | |
| 4-146 | CH₂SO₂CH₂CH₂OMe | Et | SO₂Et | |
| 4-147 | CH₂SO₂CH₂CH₂OMe | n-Pr | SO₂Et | |
| 4-148 | CH₂SO₂CH₂CH₂OMe | i-Pr | SO₂Et | |
| 4-149 | CH₂SO₂CH₂CH₂SO₂Me | Me | SO₂Et | |
| 4-150 | CH₂SO₂CH₂CH₂SO₂Me | Et | SO₂Et | |
| 4-151 | CH₂SO₂CH₂CH₂SO₂Me | n-Pr | SO₂Et | |
| 4-152 | CH₂SO₂CH₂CH₂SO₂Me | i-Pr | SO₂Et | |
| 4-153 | Cl | Me | F | |
| 4-154 | Cl | Et | F | |
| 4-155 | Cl | n-Pr | F | |
| 4-156 | Cl | i-Pr | F | |
| 4-157 | Br | Me | F | |
| 4-158 | Br | Et | F | |
| 4-159 | Br | n-Pr | F | |
| 4-160 | Br | i-Pr | F | |
| 4-161 | Me | Me | F | |
| 4-162 | Me | Et | F | |
| 4-163 | Me | n-Pr | F | |
| 4-164 | Me | i-Pr | F | |
| 4-165 | Et | Me | F | |
| 4-166 | Et | Et | F | |
| 4-167 | Et | n-Pr | F | |
| 4-168 | Et | i-Pr | F | |
| 4-169 | CF₃ | Me | F | |
| 4-170 | CF₃ | Et | F | |
| 4-171 | CF₃ | n-Pr | F | |
| 4-172 | CF₃ | i-Pr | F | |
| 4-173 | OMe | Me | F | |
| 4-174 | OMe | Et | F | |
| 4-175 | OMe | n-Pr | F | |
| 4-176 | OMe | i-Pr | F | |
| 4-177 | OEt | Me | F | |
| 4-178 | OEt | Et | F | |
| 4-179 | OEt | n-Pr | F | |
| 4-180 | OEt | i-Pr | F | |
| 4-181 | NO₂ | Me | F | |
| 4-182 | NO₂ | Et | F | |
| 4-183 | NO₂ | n-Pr | F | |
| 4-184 | NO₂ | i-Pr | F | |
| 4-185 | SO₂Me | Me | F | |
| 4-186 | SO₂Me | Et | F | |
| 4-187 | SO₂Me | n-Pr | F | |
| 4-188 | SO₂Me | i-Pr | F | |
| 4-189 | CH₂OMe | Me | F | |
| 4-190 | CH₂OMe | Et | F | |
| 4-191 | CH₂OMe | n-Pr | F | |
| 4-192 | CH₂OMe | i-Pr | F | |
| 4-193 | CH₂SO₂Me | Me | F | |
| 4-194 | CH₂SO₂Me | Et | F | |
| 4-195 | CH₂SO₂Me | n-Pr | F | |

TABLE 4-continued

Compounds of the formula (II) according to the invention $$\text{(II)}$$

| No. | X | R³ | Y | Physical data: ¹H-NMR: δ [CDCl₃] |
|---|---|---|---|---|
| 4-196 | CH₂SO₂Me | i-Pr | F | |
| 4-197 | CH₂OCH₂CH₂OMe | Me | F | |
| 4-198 | CH₂OCH₂CH₂OMe | Et | F | |
| 4-199 | CH₂OCH₂CH₂OMe | n-Pr | F | |
| 4-200 | CH₂OCH₂CH₂OMe | i-Pr | F | |
| 4-201 | CH₂OCH₂CH₂OEt | Me | F | |
| 4-202 | CH₂OCH₂CH₂OEt | Et | F | |
| 4-203 | CH₂OCH₂CH₂OEt | n-Pr | F | |
| 4-204 | CH₂OCH₂CH₂OEt | i-Pr | F | |
| 4-205 | CH₂OCH₂CH₂CH₂OMe | Me | F | |
| 4-206 | CH₂OCH₂CH₂CH₂OMe | Et | F | |
| 4-207 | CH₂OCH₂CH₂CH₂OMe | n-Pr | F | |
| 4-208 | CH₂OCH₂CH₂CH₂OMe | i-Pr | F | |
| 4-209 | CH₂OCH₂OMe | Me | F | |
| 4-210 | CH₂OCH₂OMe | Et | F | |
| 4-211 | CH₂OCH₂OMe | n-Pr | F | |
| 4-212 | CH₂OCH₂OMe | i-Pr | F | |
| 4-213 | CH₂OCH₂OEt | Me | F | |
| 4-214 | CH₂OCH₂OEt | Et | F | |
| 4-215 | CH₂OCH₂OEt | n-Pr | F | |
| 4-216 | CH₂OCH₂OEt | i-Pr | F | |
| 4-217 | CH₂OCH₂CH₂SO₂Me | Me | F | |
| 4-218 | CH₂OCH₂CH₂SO₂Me | Et | F | |
| 4-219 | CH₂OCH₂CH₂SO₂Me | n-Pr | F | |
| 4-220 | CH₂OCH₂CH₂SO₂Me | i-Pr | F | |
| 4-221 | CH₂SO₂CH₂CH₂OMe | Me | F | |
| 4-222 | CH₂SO₂CH₂CH₂OMe | Et | F | |
| 4-223 | CH₂SO₂CH₂CH₂OMe | n-Pr | F | |
| 4-224 | CH₂SO₂CH₂CH₂OMe | i-Pr | F | |
| 4-225 | CH₂SO₂CH₂CH₂SO₂Me | Me | F | |
| 4-226 | CH₂SO₂CH₂CH₂SO₂Me | Et | F | |
| 4-227 | CH₂SO₂CH₂CH₂SO₂Me | n-Pr | F | |
| 4-228 | CH₂SO₂CH₂CH₂SO₂Me | i-Pr | F | |
| 4-229 | Cl | Me | Cl | |
| 4-230 | Cl | Et | Cl | |
| 4-231 | Cl | n-Pr | Cl | |
| 4-232 | Cl | i-Pr | Cl | |
| 4-233 | Br | Me | Cl | |
| 4-234 | Br | Et | Cl | |
| 4-235 | Br | n-Pr | Cl | |
| 4-236 | Br | i-Pr | Cl | |
| 4-237 | Me | Me | Cl | (DMSO-d₆): 7.77 (d, 1H), 7.47 (d, 1H), 3.01 (s, 3H), 2.78 (s, 3H) |
| 4-238 | Me | Et | Cl | 7.92 (d, 1H), 7.35 (d, 1H), 3.39 (m, 1H), 3.16 (m, 1H), 2.92 (s, 3H), 1.38 (t, 3H) |
| 4-239 | Me | n-Pr | Cl | |
| 4-240 | Me | i-Pr | Cl | |
| 4-241 | Et | Me | Cl | |
| 4-242 | Et | Et | Cl | |
| 4-243 | Et | n-Pr | Cl | |
| 4-244 | Et | i-Pr | Cl | |
| 4-245 | CF₃ | Me | Cl | |
| 4-246 | CF₃ | Et | Cl | |
| 4-247 | CF₃ | n-Pr | Cl | |
| 4-248 | CF₃ | i-Pr | Cl | |
| 4-249 | OMe | Me | Cl | |
| 4-250 | OMe | Et | Cl | |
| 4-251 | OMe | n-Pr | Cl | |
| 4-252 | OMe | i-Pr | Cl | |
| 4-253 | OEt | Me | Cl | |
| 4-254 | OEt | Et | Cl | |
| 4-255 | OEt | n-Pr | Cl | |
| 4-256 | OEt | i-Pr | Cl | |
| 4-257 | NO₂ | Me | Cl | |
| 4-258 | NO₂ | Et | Cl | |

TABLE 4-continued

Compounds of the formula (II) according to the invention $$\text{(II)}$$

| No. | X | R³ | Y | Physical data: ¹H-NMR: δ [CDCl₃] |
|---|---|---|---|---|
| 4-259 | NO₂ | n-Pr | Cl | |
| 4-260 | NO₂ | i-Pr | Cl | |
| 4-261 | SO₂Me | Me | Cl | |
| 4-262 | SO₂Me | Et | Cl | |
| 4-263 | SO₂Me | n-Pr | Cl | |
| 4-264 | SO₂Me | i-Pr | Cl | |
| 4-265 | CH₂OMe | Me | Cl | |
| 4-266 | CH₂OMe | Et | Cl | |
| 4-267 | CH₂OMe | n-Pr | Cl | |
| 4-268 | CH₂OMe | i-Pr | Cl | |
| 4-269 | CH₂SO₂Me | Me | Cl | |
| 4-270 | CH₂SO₂Me | Et | Cl | |
| 4-271 | CH₂SO₂Me | n-Pr | Cl | |
| 4-272 | CH₂SO₂Me | i-Pr | Cl | |
| 4-273 | CH₂OCH₂CH₂OMe | Me | Cl | |
| 4-274 | CH₂OCH₂CH₂OMe | Et | Cl | |
| 4-275 | CH₂OCH₂CH₂OMe | n-Pr | Cl | |
| 4-276 | CH₂OCH₂CH₂OMe | i-Pr | Cl | |
| 4-277 | CH₂OCH₂CH₂OEt | Me | Cl | |
| 4-278 | CH₂OCH₂CH₂OEt | Et | Cl | |
| 4-279 | CH₂OCH₂CH₂OEt | n-Pr | Cl | |
| 4-280 | CH₂OCH₂CH₂OEt | i-Pr | Cl | |
| 4-281 | CH₂OCH₂CH₂CH₂OMe | Me | Cl | |
| 4-282 | CH₂OCH₂CH₂CH₂OMe | Et | Cl | |
| 4-283 | CH₂OCH₂CH₂CH₂OMe | n-Pr | Cl | |
| 4-284 | CH₂OCH₂CH₂CH₂OMe | i-Pr | Cl | |
| 4-285 | CH₂OCH₂OMe | Me | Cl | |
| 4-286 | CH₂OCH₂OMe | Et | Cl | |
| 4-287 | CH₂OCH₂OMe | n-Pr | Cl | |
| 4-288 | CH₂OCH₂OMe | i-Pr | Cl | |
| 4-289 | CH₂OCH₂OEt | Me | Cl | |
| 4-290 | CH₂OCH₂OEt | Et | Cl | |
| 4-291 | CH₂OCH₂OEt | n-Pr | Cl | |
| 4-292 | CH₂OCH₂OEt | i-Pr | Cl | |
| 4-293 | CH₂OCH₂CH₂SO₂Me | Me | Cl | |
| 4-294 | CH₂OCH₂CH₂SO₂Me | Et | Cl | |
| 4-295 | CH₂OCH₂CH₂SO₂Me | n-Pr | Cl | |
| 4-296 | CH₂OCH₂CH₂SO₂Me | i-Pr | Cl | |
| 4-297 | CH₂SO₂CH₂CH₂OMe | Me | Cl | |
| 4-298 | CH₂SO₂CH₂CH₂OMe | Et | Cl | |
| 4-299 | CH₂SO₂CH₂CH₂OMe | n-Pr | Cl | |
| 4-300 | CH₂SO₂CH₂CH₂OMe | i-Pr | Cl | |
| 4-301 | CH₂SO₂CH₂CH₂SO₂Me | Me | Cl | |
| 4-302 | CH₂SO₂CH₂CH₂SO₂Me | Et | Cl | |
| 4-303 | CH₂SO₂CH₂CH₂SO₂Me | n-Pr | Cl | |
| 4-304 | CH₂SO₂CH₂CH₂SO₂Me | i-Pr | Cl | |
| 4-305 | Cl | Me | Br | |
| 4-306 | Cl | Et | Br | |
| 4-307 | Cl | n-Pr | Br | |
| 4-308 | Cl | i-Pr | Br | |
| 4-309 | Br | Me | Br | |
| 4-310 | Br | Et | Br | |
| 4-311 | Br | n-Pr | Br | |
| 4-312 | Br | i-Pr | Br | |
| 4-313 | Me | Me | Br | (DMSO-d₆): 7.66 (d, 1H), 7.64 (d, 1H), 2.99 (s, 3H), 2.80 (s, 3H) |
| 4-314 | Me | Et | Br | |
| 4-315 | Me | n-Pr | Br | |
| 4-316 | Me | i-Pr | Br | |
| 4-317 | Et | Me | Br | |
| 4-318 | Et | Et | Br | |
| 4-319 | Et | n-Pr | Br | |
| 4-320 | Et | i-Pr | Br | |
| 4-321 | CF₃ | Me | Br | |
| 4-322 | CF₃ | Et | Br | |
| 4-323 | CF₃ | n-Pr | Br | |

TABLE 4-continued

Compounds of the formula (II) according to the invention $$\text{(II)}$$

| No. | X | R³ | Y | Physical data: ¹H-NMR: δ [CDCl₃] |
|---|---|---|---|---|
| 4-324 | CF₃ | i-Pr | Br | |
| 4-325 | OMe | Me | Br | |
| 4-326 | OMe | Et | Br | |
| 4-327 | OMe | n-Pr | Br | |
| 4-328 | OMe | i-Pr | Br | |
| 4-329 | OEt | Me | Br | |
| 4-330 | OEt | Et | Br | |
| 4-331 | OEt | n-Pr | Br | |
| 4-332 | OEt | i-Pr | Br | |
| 4-333 | NO₂ | Me | Br | |
| 4-334 | NO₂ | Et | Br | |
| 4-335 | NO₂ | n-Pr | Br | |
| 4-336 | NO₂ | i-Pr | Br | |
| 4-337 | SO₂Me | Me | Br | |
| 4-338 | SO₂Me | Et | Br | |
| 4-339 | SO₂Me | n-Pr | Br | |
| 4-340 | SO₂Me | i-Pr | Br | |
| 4-341 | CH₂OMe | Me | Br | |
| 4-342 | CH₂OMe | Et | Br | |
| 4-343 | CH₂OMe | n-Pr | Br | |
| 4-344 | CH₂OMe | i-Pr | Br | |
| 4-345 | CH₂SO₂Me | Me | Br | |
| 4-346 | CH₂SO₂Me | Et | Br | |
| 4-347 | CH₂SO₂Me | n-Pr | Br | |
| 4-348 | CH₂SO₂Me | i-Pr | Br | |
| 4-349 | CH₂OCH₂CH₂OMe | Me | Br | |
| 4-350 | CH₂OCH₂CH₂OMe | Et | Br | |
| 4-351 | CH₂OCH₂CH₂OMe | n-Pr | Br | |
| 4-352 | CH₂OCH₂CH₂OMe | i-Pr | Br | |
| 4-353 | CH₂OCH₂CH₂OEt | Me | Br | |
| 4-354 | CH₂OCH₂CH₂OEt | Et | Br | |
| 4-355 | CH₂OCH₂CH₂OEt | n-Pr | Br | |
| 4-356 | CH₂OCH₂CH₂OEt | i-Pr | Br | |
| 4-357 | CH₂OCH₂CH₂CH₂OMe | Me | Br | |
| 4-358 | CH₂OCH₂CH₂CH₂OMe | Et | Br | |
| 4-359 | CH₂OCH₂CH₂CH₂OMe | n-Pr | Br | |
| 4-360 | CH₂OCH₂CH₂CH₂OMe | i-Pr | Br | |
| 4-361 | CH₂OCH₂OMe | Me | Br | |
| 4-362 | CH₂OCH₂OMe | Et | Br | |
| 4-363 | CH₂OCH₂OMe | n-Pr | Br | |
| 4-364 | CH₂OCH₂OMe | i-Pr | Br | |
| 4-365 | CH₂OCH₂OEt | Me | Br | |
| 4-366 | CH₂OCH₂OEt | Et | Br | |
| 4-367 | CH₂OCH₂OEt | n-Pr | Br | |
| 4-368 | CH₂OCH₂OEt | i-Pr | Br | |
| 4-369 | CH₂OCH₂CH₂SO₂Me | Me | Br | |
| 4-370 | CH₂OCH₂CH₂SO₂Me | Et | Br | |
| 4-371 | CH₂OCH₂CH₂SO₂Me | n-Pr | Br | |
| 4-372 | CH₂OCH₂CH₂SO₂Me | i-Pr | Br | |
| 4-373 | CH₂SO₂CH₂CH₂OMe | Me | Br | |
| 4-374 | CH₂SO₂CH₂CH₂OMe | Et | Br | |
| 4-375 | CH₂SO₂CH₂CH₂OMe | n-Pr | Br | |
| 4-376 | CH₂SO₂CH₂CH₂OMe | i-Pr | Br | |
| 4-377 | CH₂SO₂CH₂CH₂SO₂Me | Me | Br | |
| 4-378 | CH₂SO₂CH₂CH₂SO₂Me | Et | Br | |
| 4-379 | CH₂SO₂CH₂CH₂SO₂Me | n-Pr | Br | |
| 4-380 | CH₂SO₂CH₂CH₂SO₂Me | i-Pr | Br | |
| 4-381 | Cl | Me | I | |
| 4-382 | Cl | Et | I | |
| 4-383 | Cl | n-Pr | I | |
| 4-384 | Cl | i-Pr | I | |
| 4-385 | Br | Me | I | |
| 4-386 | Br | Et | I | |
| 4-387 | Br | n-Pr | I | |

TABLE 4-continued

Compounds of the formula (II) according to the invention

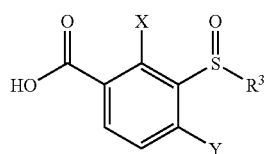

(II)

| No. | X | R³ | Y | Physical data: ¹H-NMR: δ [CDCl₃] |
|---|---|---|---|---|
| 4-388 | Br | i-Pr | I | |
| 4-389 | Me | Me | I | 7.87 (d, 1H), 7.61 (d, 1H), 2.99 (s, 3H), 2.98 (s, 3H) |
| 4-390 | Me | Et | I | |
| 4-391 | Me | n-Pr | I | |
| 4-392 | Me | i-Pr | I | |
| 4-393 | Et | Me | I | |
| 4-394 | Et | Et | I | |
| 4-395 | Et | n-Pr | I | |
| 4-396 | Et | i-Pr | I | |
| 4-397 | CF₃ | Me | I | |
| 4-398 | CF₃ | Et | I | |
| 4-399 | CF₃ | n-Pr | I | |
| 4-400 | CF₃ | i-Pr | I | |
| 4-401 | OMe | Me | I | |
| 4-402 | OMe | Et | I | |
| 4-403 | OMe | n-Pr | I | |
| 4-404 | OMe | i-Pr | I | |
| 4-405 | OEt | Me | I | |
| 4-406 | OEt | Et | I | |
| 4-407 | OEt | n-Pr | I | |
| 4-408 | OEt | i-Pr | I | |
| 4-409 | NO₂ | Me | I | |
| 4-410 | NO₂ | Et | I | |
| 4-411 | NO₂ | n-Pr | I | |
| 4-412 | NO₂ | i-Pr | I | |
| 4-413 | SO₂Me | Me | I | |
| 4-414 | SO₂Me | Et | I | |
| 4-415 | SO₂Me | n-Pr | I | |
| 4-416 | SO₂Me | i-Pr | I | |
| 4-417 | CH₂OMe | Me | I | |
| 4-418 | CH₂OMe | Et | I | |
| 4-419 | CH₂OMe | n-Pr | I | |
| 4-420 | CH₂OMe | i-Pr | I | |
| 4-421 | CH₂SO₂Me | Me | I | |
| 4-422 | CH₂SO₂Me | Et | I | |
| 4-423 | CH₂SO₂Me | n-Pr | I | |
| 4-424 | CH₂SO₂Me | i-Pr | I | |
| 4-425 | CH₂OCH₂CH₂OMe | Me | I | |
| 4-426 | CH₂OCH₂CH₂OMe | Et | I | |
| 4-427 | CH₂OCH₂CH₂OMe | n-Pr | I | |
| 4-428 | CH₂OCH₂CH₂OMe | i-Pr | I | |
| 4-429 | CH₂OCH₂CH₂OEt | Me | I | |
| 4-430 | CH₂OCH₂CH₂OEt | Et | I | |
| 4-431 | CH₂OCH₂CH₂OEt | n-Pr | I | |
| 4-432 | CH₂OCH₂CH₂OEt | i-Pr | I | |
| 4-433 | CH₂OCH₂CH₂CH₂OMe | Me | I | |
| 4-434 | CH₂OCH₂CH₂CH₂OMe | Et | I | |
| 4-435 | CH₂OCH₂CH₂CH₂OMe | n-Pr | I | |
| 4-436 | CH₂OCH₂CH₂CH₂OMe | i-Pr | I | |
| 4-437 | CH₂OCH₂OMe | Me | I | |
| 4-438 | CH₂OCH₂OMe | Et | I | |
| 4-439 | CH₂OCH₂OMe | n-Pr | I | |
| 4-440 | CH₂OCH₂OMe | i-Pr | I | |
| 4-441 | CH₂OCH₂OEt | Me | I | |
| 4-442 | CH₂OCH₂OEt | Et | I | |
| 4-443 | CH₂OCH₂OEt | n-Pr | I | |
| 4-444 | CH₂OCH₂OEt | i-Pr | I | |
| 4-445 | CH₂OCH₂CH₂SO₂Me | Me | I | |
| 4-446 | CH₂OCH₂CH₂SO₂Me | Et | I | |
| 4-447 | CH₂OCH₂CH₂SO₂Me | n-Pr | I | |
| 4-448 | CH₂OCH₂CH₂SO₂Me | i-Pr | I | |
| 4-449 | CH₂SO₂CH₂CH₂OMe | Me | I | |
| 4-450 | CH₂SO₂CH₂CH₂OMe | Et | I | |
| 4-451 | CH₂SO₂CH₂CH₂OMe | n-Pr | I | |
| 4-452 | CH₂SO₂CH₂CH₂OMe | i-Pr | I | |

TABLE 4-continued

Compounds of the formula (II) according to the invention (II)

| No. | X | R³ | Y | Physical data: ¹H-NMR: δ [CDCl₃] |
|---|---|---|---|---|
| 4-453 | CH₂SO₂CH₂CH₂SO₂Me | Me | I | |
| 4-454 | CH₂SO₂CH₂CH₂SO₂Me | Et | I | |
| 4-455 | CH₂SO₂CH₂CH₂SO₂Me | n-Pr | I | |
| 4-456 | CH₂SO₂CH₂CH₂SO₂Me | i-Pr | I | |
| 4-457 | Cl | Me | NO₂ | |
| 4-458 | Cl | Et | NO₂ | |
| 4-459 | Cl | n-Pr | NO₂ | |
| 4-460 | Cl | i-Pr | NO₂ | |
| 4-461 | Br | Me | NO₂ | |
| 4-462 | Br | Et | NO₂ | |
| 4-463 | Br | n-Pr | NO₂ | |
| 4-464 | Br | i-Pr | NO₂ | |
| 4-465 | Me | Me | NO₂ | |
| 4-466 | Me | Et | NO₂ | |
| 4-467 | Me | n-Pr | NO₂ | |
| 4-468 | Me | i-Pr | NO₂ | |
| 4-469 | Et | Me | NO₂ | |
| 4-470 | Et | Et | NO₂ | |
| 4-471 | Et | n-Pr | NO₂ | |
| 4-472 | Et | i-Pr | NO₂ | |
| 4-473 | CF₃ | Me | NO₂ | |
| 4-474 | CF₃ | Et | NO₂ | |
| 4-475 | CF₃ | n-Pr | NO₂ | |
| 4-476 | CF₃ | i-Pr | NO₂ | |
| 4-477 | OMe | Me | NO₂ | |
| 4-478 | OMe | Et | NO₂ | |
| 4-479 | OMe | n-Pr | NO₂ | |
| 4-480 | OMe | i-Pr | NO₂ | |
| 4-481 | OEt | Me | NO₂ | |
| 4-482 | OEt | Et | NO₂ | |
| 4-483 | OEt | n-Pr | NO₂ | |
| 4-484 | OEt | i-Pr | NO₂ | |
| 4-485 | NO₂ | Me | NO₂ | |
| 4-486 | NO₂ | Et | NO₂ | |
| 4-487 | NO₂ | n-Pr | NO₂ | |
| 4-488 | NO₂ | i-Pr | NO₂ | |
| 4-489 | SO₂Me | Me | NO₂ | |
| 4-490 | SO₂Me | Et | NO₂ | |
| 4-491 | SO₂Me | n-Pr | NO₂ | |
| 4-492 | SO₂Me | i-Pr | NO₂ | |
| 4-493 | CH₂OMe | Me | NO₂ | |
| 4-494 | CH₂OMe | Et | NO₂ | |
| 4-495 | CH₂OMe | n-Pr | NO₂ | |
| 4-496 | CH₂OMe | i-Pr | NO₂ | |
| 4-497 | CH₂SO₂Me | Me | NO₂ | |
| 4-498 | CH₂SO₂Me | Et | NO₂ | |
| 4-499 | CH₂SO₂Me | n-Pr | NO₂ | |
| 4-500 | CH₂SO₂Me | i-Pr | NO₂ | |
| 4-501 | CH₂OCH₂CH₂OMe | Me | NO₂ | |
| 4-502 | CH₂OCH₂CH₂OMe | Et | NO₂ | |
| 4-503 | CH₂OCH₂CH₂OMe | n-Pr | NO₂ | |
| 4-504 | CH₂OCH₂CH₂OMe | i-Pr | NO₂ | |
| 4-505 | CH₂OCH₂CH₂OEt | Me | NO₂ | |
| 4-506 | CH₂OCH₂CH₂OEt | Et | NO₂ | |
| 4-507 | CH₂OCH₂CH₂OEt | n-Pr | NO₂ | |
| 4-508 | CH₂OCH₂CH₂OEt | i-Pr | NO₂ | |
| 4-509 | CH₂OCH₂CH₂CH₂OMe | Me | NO₂ | |
| 4-510 | CH₂OCH₂CH₂CH₂OMe | Et | NO₂ | |
| 4-511 | CH₂OCH₂CH₂CH₂OMe | n-Pr | NO₂ | |
| 4-512 | CH₂OCH₂CH₂CH₂OMe | i-Pr | NO₂ | |
| 4-513 | CH₂OCH₂OMe | Me | NO₂ | |
| 4-514 | CH₂OCH₂OMe | Et | NO₂ | |
| 4-515 | CH₂OCH₂OMe | n-Pr | NO₂ | |
| 4-516 | CH₂OCH₂OMe | i-Pr | NO₂ | |
| 4-517 | CH₂OCH₂OEt | Me | NO₂ | |
| 4-518 | CH₂OCH₂OEt | Et | NO₂ | |

TABLE 4-continued

Compounds of the formula (II) according to the invention

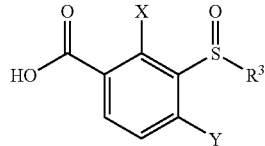

(II)

| No. | X | R³ | Y | Physical data: ¹H-NMR: δ [CDCl₃] |
|---|---|---|---|---|
| 4-519 | CH₂OCH₂OEt | n-Pr | NO₂ | |
| 4-520 | CH₂OCH₂OEt | i-Pr | NO₂ | |
| 4-521 | CH₂OCH₂CH₂SO₂Me | Me | NO₂ | |
| 4-522 | CH₂OCH₂CH₂SO₂Me | Et | NO₂ | |
| 4-523 | CH₂OCH₂CH₂SO₂Me | n-Pr | NO₂ | |
| 4-524 | CH₂OCH₂CH₂SO₂Me | i-Pr | NO₂ | |
| 4-525 | CH₂SO₂CH₂CH₂OMe | Me | NO₂ | |
| 4-526 | CH₂SO₂CH₂CH₂OMe | Et | NO₂ | |
| 4-527 | CH₂SO₂CH₂CH₂OMe | n-Pr | NO₂ | |
| 4-528 | CH₂SO₂CH₂CH₂OMe | i-Pr | NO₂ | |
| 4-529 | CH₂SO₂CH₂CH₂SO₂Me | Me | NO₂ | |
| 4-530 | CH₂SO₂CH₂CH₂SO₂Me | Et | NO₂ | |
| 4-531 | CH₂SO₂CH₂CH₂SO₂Me | n-Pr | NO₂ | |
| 4-532 | CH₂SO₂CH₂CH₂SO₂Me | i-Pr | NO₂ | |

TABLE 5

Compounds of the formula (I) according to the invention in which R¹ is methyl and R² is hydrogen.

| No. | X | R³ | Y | R⁴ | Physical data: ¹H-NMR: δ [CDCl₃] |
|---|---|---|---|---|---|
| 5-1 | Cl | Me | SO₂Me | —SO₂-n-Pr | |
| 5-2 | Cl | Et | SO₂Me | —SO₂-n-Pr | |
| 5-3 | Me | Me | SO₂Me | —SO₂-n-Pr | |
| 5-4 | Me | Et | SO₂Me | —SO₂-n-Pr | |
| 5-5 | CF₃ | Me | SO₂Me | —SO₂-n-Pr | |
| 5-6 | CF₃ | Et | SO₂Me | —SO₂-n-Pr | |
| 5-7 | OMe | Me | SO₂Me | —SO₂-n-Pr | |
| 5-8 | OMe | Et | SO₂Me | —SO₂-n-Pr | |
| 5-9 | NO₂ | Me | SO₂Me | —SO₂-n-Pr | |
| 5-10 | NO₂ | Et | SO₂Me | —SO₂-n-Pr | |
| 5-11 | SO₂Me | Me | SO₂Me | —SO₂-n-Pr | |
| 5-12 | SO₂Me | Et | SO₂Me | —SO₂-n-Pr | |
| 5-13 | CH₂OMe | Me | SO₂Me | —SO₂-n-Pr | |
| 5-14 | CH₂OMe | Et | SO₂Me | —SO₂-n-Pr | |
| 5-15 | CH₂SO₂Me | Me | SO₂Me | —SO₂-n-Pr | |
| 5-16 | CH₂SO₂Me | Et | SO₂Me | —SO₂-n-Pr | |
| 5-17 | CH₂OCH₂OMe | Me | SO₂Me | —SO₂-n-Pr | |
| 5-18 | CH₂OCH₂OMe | Et | SO₂Me | —SO₂-n-Pr | |
| 5-19 | Cl | Me | Cl | —SO₂-n-Pr | |
| 5-20 | Cl | Et | Cl | —SO₂-n-Pr | |
| 5-21 | Me | Me | Cl | —SO₂-n-Pr | |
| 5-22 | Me | Et | Cl | —SO₂-n-Pr | |
| 5-23 | CF₃ | Me | Cl | —SO₂-n-Pr | |
| 5-24 | CF₃ | Et | Cl | —SO₂-n-Pr | |
| 5-25 | OMe | Me | Cl | —SO₂-n-Pr | |
| 5-26 | OMe | Et | Cl | —SO₂-n-Pr | |
| 5-27 | NO₂ | Me | Cl | —SO₂-n-Pr | |
| 5-28 | NO₂ | Et | Cl | —SO₂-n-Pr | |
| 5-29 | SO₂Me | Me | Cl | —SO₂-n-Pr | |
| 5-30 | SO₂Me | Et | Cl | —SO₂-n-Pr | |
| 5-31 | CH₂OMe | Me | Cl | —SO₂-n-Pr | |

TABLE 5-continued

Compounds of the formula (I) according to the invention in which $R^1$ is methyl and $R^2$ is hydrogen.

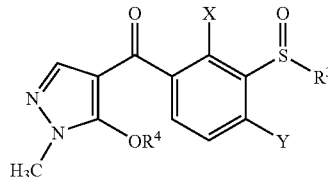

| No. | X | $R^3$ | Y | $R^4$ | Physical data: $^1$H-NMR: δ [CDCl$_3$] |
|---|---|---|---|---|---|
| 5-32 | CH$_2$OMe | Et | Cl | —SO$_2$-n-Pr | |
| 5-33 | CH$_2$SO$_2$Me | Me | Cl | —SO$_2$-n-Pr | |
| 5-34 | CH$_2$SO$_2$Me | Et | Cl | —SO$_2$-n-Pr | |
| 5-35 | CH$_2$OCH$_2$CH$_2$OMe | Me | Cl | —SO$_2$-n-Pr | |
| 5-36 | CH$_2$OCH$_2$CH$_2$OMe | Et | Cl | —SO$_2$-n-Pr | |
| 5-37 | Cl | Me | Br | —SO$_2$-n-Pr | |
| 5-38 | Cl | Et | Br | —SO$_2$-n-Pr | |
| 5-39 | Me | Me | Br | —SO$_2$-n-Pr | |
| 5-40 | Me | Et | Br | —SO$_2$-n-Pr | |
| 5-41 | CF$_3$ | Me | Br | —SO$_2$-n-Pr | |
| 5-42 | CF$_3$ | Et | Br | —SO$_2$-n-Pr | |
| 5-43 | OMe | Me | Br | —SO$_2$-n-Pr | |
| 5-44 | OMe | Et | Br | —SO$_2$-n-Pr | |
| 5-45 | NO$_2$ | Me | Br | —SO$_2$-n-Pr | |
| 5-46 | NO$_2$ | Et | Br | —SO$_2$-n-Pr | |
| 5-47 | SO$_2$Me | Me | Br | —SO$_2$-n-Pr | |
| 5-48 | SO$_2$Me | Et | Br | —SO$_2$-n-Pr | |
| 5-49 | CH$_2$OMe | Me | Br | —SO$_2$-n-Pr | |
| 5-50 | CH$_2$OMe | Et | Br | —SO$_2$-n-Pr | |
| 5-51 | CH$_2$SO$_2$Me | Me | Br | —SO$_2$-n-Pr | |
| 5-52 | CH$_2$SO$_2$Me | Et | Br | —SO$_2$-n-Pr | |
| 5-53 | CH$_2$OCH$_2$CH$_2$OMe | Me | Br | —SO$_2$-n-Pr | |
| 5-54 | CH$_2$OCH$_2$CH$_2$OMe | Et | Br | —SO$_2$-n-Pr | |
| 5-55 | Cl | Me | I | —SO$_2$-n-Pr | |
| 5-56 | Cl | Et | I | —SO$_2$-n-Pr | |
| 5-57 | Me | Me | I | —SO$_2$-n-Pr | |
| 5-58 | Me | Et | I | —SO$_2$-n-Pr | |
| 5-59 | CF$_3$ | Me | I | —SO$_2$-n-Pr | |
| 5-60 | CF$_3$ | Et | I | —SO$_2$-n-Pr | |
| 5-61 | OMe | Me | I | —SO$_2$-n-Pr | |
| 5-62 | OMe | Et | I | —SO$_2$-n-Pr | |
| 5-63 | NO$_2$ | Me | I | —SO$_2$-n-Pr | |
| 5-64 | NO$_2$ | Et | I | —SO$_2$-n-Pr | |
| 5-65 | SO$_2$Me | Me | I | —SO$_2$-n-Pr | |
| 5-66 | SO$_2$Me | Et | I | —SO$_2$-n-Pr | |
| 5-67 | CH$_2$OMe | Me | I | —SO$_2$-n-Pr | |
| 5-68 | CH$_2$OMe | Et | I | —SO$_2$-n-Pr | |
| 5-69 | CH$_2$SO$_2$Me | Me | I | —SO$_2$-n-Pr | |
| 5-70 | CH$_2$SO$_2$Me | Et | I | —SO$_2$-n-Pr | |
| 5-71 | CH$_2$OCH$_2$CH$_2$OMe | Me | I | —SO$_2$-n-Pr | |
| 5-72 | CH$_2$OCH$_2$CH$_2$OMe | Et | I | —SO$_2$-n-Pr | |
| 5-73 | Cl | Me | NO$_2$ | —SO$_2$-n-Pr | |
| 5-74 | Cl | Et | NO$_2$ | —SO$_2$-n-Pr | |
| 5-75 | Me | Me | NO$_2$ | —SO$_2$-n-Pr | |
| 5-76 | Me | Et | NO$_2$ | —SO$_2$-n-Pr | |
| 5-77 | CF$_3$ | Me | NO$_2$ | —SO$_2$-n-Pr | |
| 5-78 | CF$_3$ | Et | NO$_2$ | —SO$_2$-n-Pr | |
| 5-79 | OMe | Me | NO$_2$ | —SO$_2$-n-Pr | |
| 5-80 | OMe | Et | NO$_2$ | —SO$_2$-n-Pr | |
| 5-81 | NO$_2$ | Me | NO$_2$ | —SO$_2$-n-Pr | |
| 5-82 | NO$_2$ | Et | NO$_2$ | —SO$_2$-n-Pr | |
| 5-83 | SO$_2$Me | Me | NO$_2$ | —SO$_2$-n-Pr | |
| 5-84 | SO$_2$Me | Et | NO$_2$ | —SO$_2$-n-Pr | |
| 5-85 | CH$_2$OMe | Me | NO$_2$ | —SO$_2$-n-Pr | |
| 5-86 | CH$_2$OMe | Et | NO$_2$ | —SO$_2$-n-Pr | |
| 5-87 | CH$_2$SO$_2$Me | Me | NO$_2$ | —SO$_2$-n-Pr | |
| 5-88 | CH$_2$SO$_2$Me | Et | NO$_2$ | —SO$_2$-n-Pr | |
| 5-89 | CH$_2$OCH$_2$CH$_2$OMe | Me | NO$_2$ | —SO$_2$-n-Pr | |
| 5-90 | CH$_2$OCH$_2$CH$_2$OMe | Et | NO$_2$ | —SO$_2$-n-Pr | |
| 5-91 | Cl | Me | SO$_2$Me | —CO-Ph | |
| 5-92 | Cl | Et | SO$_2$Me | —CO-Ph | |
| 5-93 | Me | Me | SO$_2$Me | —CO-Ph | |
| 5-94 | Me | Et | SO$_2$Me | —CO-Ph | |
| 5-95 | CF$_3$ | Me | SO$_2$Me | —CO-Ph | |

TABLE 5-continued

Compounds of the formula (I) according to the invention in which $R^1$ is methyl and $R^2$ is hydrogen.

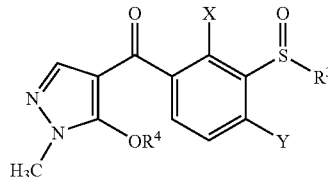

| No. | X | $R^3$ | Y | $R^4$ | Physical data: $^1$H-NMR: δ [CDCl$_3$] |
|---|---|---|---|---|---|
| 5-96 | CF$_3$ | Et | SO$_2$Me | —CO-Ph | |
| 5-97 | OMe | Me | SO$_2$Me | —CO-Ph | |
| 5-98 | OMe | Et | SO$_2$Me | —CO-Ph | |
| 5-99 | NO$_2$ | Me | SO$_2$Me | —CO-Ph | |
| 5-100 | NO$_2$ | Et | SO$_2$Me | —CO-Ph | |
| 5-101 | SO$_2$Me | Me | SO$_2$Me | —CO-Ph | |
| 5-102 | SO$_2$Me | Et | SO$_2$Me | —CO-Ph | |
| 5-103 | CH$_2$OMe | Me | SO$_2$Me | —CO-Ph | |
| 5-104 | CH$_2$OMe | Et | SO$_2$Me | —CO-Ph | |
| 5-105 | CH$_2$SO$_2$Me | Me | SO$_2$Me | —CO-Ph | |
| 5-106 | CH$_2$SO$_2$Me | Et | SO$_2$Me | —CO-Ph | |
| 5-107 | CH$_2$OCH$_2$CH$_2$OMe | Me | SO$_2$Me | —CO-Ph | |
| 5-108 | CH$_2$OCH$_2$CH$_2$OMe | Et | SO$_2$Me | —CO-Ph | |
| 5-109 | Cl | Me | Cl | —CO-Ph | |
| 5-110 | Cl | Et | Cl | —CO-Ph | |
| 5-111 | Me | Me | Cl | —CO-Ph | |
| 5-112 | Me | Et | Cl | —CO-Ph | |
| 5-113 | CF$_3$ | Me | Cl | —CO-Ph | |
| 5-114 | CF$_3$ | Et | Cl | —CO-Ph | |
| 5-115 | OMe | Me | Cl | —CO-Ph | |
| 5-116 | OMe | Et | Cl | —CO-Ph | |
| 5-117 | NO$_2$ | Me | Cl | —CO-Ph | |
| 5-118 | NO$_2$ | Et | Cl | —CO-Ph | |
| 5-119 | SO$_2$Me | Me | Cl | —CO-Ph | |
| 5-120 | SO$_2$Me | Et | Cl | —CO-Ph | |
| 5-121 | CH$_2$OMe | Me | Cl | —CO-Ph | |
| 5-122 | CH$_2$OMe | Et | Cl | —CO-Ph | |
| 5-123 | CH$_2$SO$_2$Me | Me | Cl | —CO-Ph | |
| 5-124 | CH$_2$SO$_2$Me | Et | Cl | —CO-Ph | |
| 5-125 | CH$_2$OCH$_2$CH$_2$OMe | Me | Cl | —CO-Ph | |
| 5-126 | CH$_2$OCH$_2$CH$_2$OMe | Et | Cl | —CO-Ph | |
| 5-127 | Cl | Me | Br | —CO-Ph | |
| 5-128 | Cl | Et | Br | —CO-Ph | |
| 5-129 | Me | Me | Br | —CO-Ph | |
| 5-130 | Me | Et | Br | —CO-Ph | |
| 5-131 | CF$_3$ | Me | Br | —CO-Ph | |
| 5-132 | CF$_3$ | Et | Br | —CO-Ph | |
| 5-133 | OMe | Me | Br | —CO-Ph | |
| 5-134 | OMe | Et | Br | —CO-Ph | |
| 5-135 | NO$_2$ | Me | Br | —CO-Ph | |
| 5-136 | NO$_2$ | Et | Br | —CO-Ph | |
| 5-137 | SO$_2$Me | Me | Br | —CO-Ph | |
| 5-138 | SO$_2$Me | Et | Br | —CO-Ph | |
| 5-139 | CH$_2$OMe | Me | Br | —CO-Ph | |
| 5-140 | CH$_2$OMe | Et | Br | —CO-Ph | |
| 5-141 | CH$_2$SO$_2$Me | Me | Br | —CO-Ph | |
| 5-142 | CH$_2$SO$_2$Me | Et | Br | —CO-Ph | |
| 5-143 | CH$_2$OCH$_2$CH$_2$OMe | Me | Br | —CO-Ph | |
| 5-144 | CH$_2$OCH$_2$CH$_2$OMe | Et | Br | —CO-Ph | |
| 5-145 | Cl | Me | Cl | —CO-Ph | |
| 5-146 | Cl | Et | Cl | —CO-Ph | |
| 5-147 | Me | Me | Cl | —CO-Ph | |
| 5-148 | Me | Et | Cl | —CO-Ph | |
| 5-149 | CF$_3$ | Me | Cl | —CO-Ph | |
| 5-150 | CF$_3$ | Et | Cl | —CO-Ph | |
| 5-151 | OMe | Me | Cl | —CO-Ph | |
| 5-152 | OMe | Et | Cl | —CO-Ph | |
| 5-153 | NO$_2$ | Me | Cl | —CO-Ph | |
| 5-154 | NO$_2$ | Et | Cl | —CO-Ph | |
| 5-155 | SO$_2$Me | Me | Cl | —CO-Ph | |
| 5-156 | SO$_2$Me | Et | Cl | —CO-Ph | |
| 5-157 | CH$_2$OMe | Me | Cl | —CO-Ph | |
| 5-158 | CH$_2$OMe | Et | Cl | —CO-Ph | |
| 5-159 | CH$_2$SO$_2$Me | Me | Cl | —CO-Ph | |

TABLE 5-continued

Compounds of the formula (I) according to the invention in which $R^1$ is methyl and $R^2$ is hydrogen.

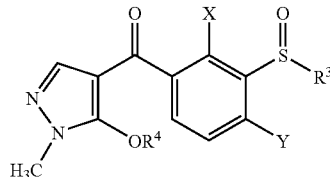

| No. | X | $R^3$ | Y | $R^4$ | Physical data: $^1$H-NMR: δ [CDCl$_3$] |
|---|---|---|---|---|---|
| 5-160 | CH$_2$SO$_2$Me | Et | Cl | —CO-Ph | |
| 5-161 | CH$_2$OCH$_2$CH$_2$OMe | Me | Cl | —CO-Ph | |
| 5-162 | CH$_2$OCH$_2$CH$_2$OMe | Et | Cl | —CO-Ph | |
| 5-163 | Cl | Me | NO$_2$ | —CO-Ph | |
| 5-164 | Cl | Et | NO$_2$ | —CO-Ph | |
| 5-165 | Me | Me | NO$_2$ | —CO-Ph | |
| 5-166 | Me | Et | NO$_2$ | —CO-Ph | |
| 5-167 | CF$_3$ | Me | NO$_2$ | —CO-Ph | |
| 5-168 | CF$_3$ | Et | NO$_2$ | —CO-Ph | |
| 5-169 | OMe | Me | NO$_2$ | —CO-Ph | |
| 5-170 | OMe | Et | NO$_2$ | —CO-Ph | |
| 5-171 | NO$_2$ | Me | NO$_2$ | —CO-Ph | |
| 5-172 | NO$_2$ | Et | NO$_2$ | —CO-Ph | |
| 5-173 | SO$_2$Me | Me | NO$_2$ | —CO-Ph | |
| 5-174 | SO$_2$Me | Et | NO$_2$ | —CO-Ph | |
| 5-175 | CH$_2$OMe | Me | NO$_2$ | —CO-Ph | |
| 5-176 | CH$_2$OMe | Et | NO$_2$ | —CO-Ph | |
| 5-177 | CH$_2$SO$_2$Me | Me | NO$_2$ | —CO-Ph | |
| 5-178 | CH$_2$SO$_2$Me | Et | NO$_2$ | —CO-Ph | |
| 5-179 | CH$_2$OCH$_2$CH$_2$OMe | Me | NO$_2$ | —CO-Ph | |
| 5-180 | CH$_2$OCH$_2$CH$_2$OMe | Et | NO$_2$ | —CO-Ph | |
| 5-181 | Cl | Me | SO$_2$Me | —CH$_2$—CO—(4-Me-Ph) | |
| 5-182 | Cl | Et | SO$_2$Me | —CH$_2$—CO—(4-Me-Ph) | |
| 5-183 | Me | Me | SO$_2$Me | —CH$_2$—CO—(4-Me-Ph) | |
| 5-184 | Me | Et | SO$_2$Me | —CH$_2$—CO—(4-Me-Ph) | |
| 5-185 | CF$_3$ | Me | SO$_2$Me | —CH$_2$—CO—(4-Me-Ph) | |
| 5-186 | CF$_3$ | Et | SO$_2$Me | —CH$_2$—CO—(4-Me-Ph) | |
| 5-187 | OMe | Me | SO$_2$Me | —CH$_2$—CO—(4-Me-Ph) | |
| 5-188 | OMe | Et | SO$_2$Me | —CH$_2$—CO—(4-Me-Ph) | |
| 5-189 | NO$_2$ | Me | SO$_2$Me | —CH$_2$—CO—(4-Me-Ph) | |
| 5-190 | NO$_2$ | Et | SO$_2$Me | —CH$_2$—CO—(4-Me-Ph) | |
| 5-191 | SO$_2$Me | Me | SO$_2$Me | —CH$_2$—CO—(4-Me-Ph) | |
| 5-192 | SO$_2$Me | Et | SO$_2$Me | —CH$_2$—CO—(4-Me-Ph) | |
| 5-193 | CH$_2$OMe | Me | SO$_2$Me | —CH$_2$—CO—(4-Me-Ph) | |
| 5-194 | CH$_2$OMe | Et | SO$_2$Me | —CH$_2$—CO—(4-Me-Ph) | |
| 5-195 | CH$_2$SO$_2$Me | Me | SO$_2$Me | —CH$_2$—CO—(4-Me-Ph) | |
| 5-196 | CH$_2$SO$_2$Me | Et | SO$_2$Me | —CH$_2$—CO—(4-Me-Ph) | |
| 5-197 | CH$_2$OCH$_2$CH$_2$OMe | Me | SO$_2$Me | —CH$_2$—CO—(4-Me-Ph) | |
| 5-198 | CH$_2$OCH$_2$CH$_2$OMe | Et | SO$_2$Me | —CH$_2$—CO—(4-Me-Ph) | |
| 5-199 | Cl | Me | Cl | —CH$_2$—CO—(4-Me-Ph) | |
| 5-200 | Cl | Et | Cl | —CH$_2$—CO—(4-Me-Ph) | |
| 5-201 | Me | Me | Cl | —CH$_2$—CO—(4-Me-Ph) | |

TABLE 5-continued

Compounds of the formula (I) according to the invention in which $R^1$ is methyl and $R^2$ is hydrogen.

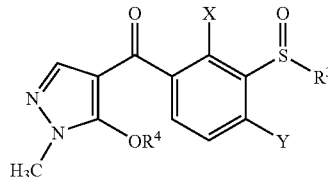

| No. | X | $R^3$ | Y | $R^4$ | Physical data: $^1$H-NMR: δ [CDCl$_3$] |
|---|---|---|---|---|---|
| 5-202 | Me | Et | Cl | —CH$_2$—CO—(4-Me-Ph) | |
| 5-203 | CF$_3$ | Me | Cl | —CH$_2$—CO—(4-Me-Ph) | |
| 5-204 | CF$_3$ | Et | Cl | —CH$_2$—CO—(4-Me-Ph) | |
| 5-205 | OMe | Me | Cl | —CH$_2$—CO—(4-Me-Ph) | |
| 5-206 | OMe | Et | Cl | —CH$_2$—CO—(4-Me-Ph) | |
| 5-207 | NO$_2$ | Me | Cl | —CH$_2$—CO—(4-Me-Ph) | |
| 5-208 | NO$_2$ | Et | Cl | —CH$_2$—CO—(4-Me-Ph) | |
| 5-209 | SO$_2$Me | Me | Cl | —CH$_2$—CO—(4-Me-Ph) | |
| 5-210 | SO$_2$Me | Et | Cl | —CH$_2$—CO—(4-Me-Ph) | |
| 5-211 | CH$_2$OMe | Me | Cl | —CH$_2$—CO—(4-Me-Ph) | |
| 5-212 | CH$_2$OMe | Et | Cl | —CH$_2$—CO—(4-Me-Ph) | |
| 5-213 | CH$_2$SO$_2$Me | Me | Cl | —CH$_2$—CO—(4-Me-Ph) | |
| 5-214 | CH$_2$SO$_2$Me | Et | Cl | —CH$_2$—CO—(4-Me-Ph) | |
| 5-215 | CH$_2$OCH$_2$OMe | Me | Cl | —CH$_2$—CO—(4-Me-Ph) | |
| 5-216 | CH$_2$OCH$_2$OMe | Et | Cl | —CH$_2$—CO—(4-Me-Ph) | |
| 5-217 | Cl | Me | Br | —CH$_2$—CO—(4-Me-Ph) | |
| 5-218 | Cl | Et | Br | —CH$_2$—CO—(4-Me-Ph) | |
| 5-219 | Me | Me | Br | —CH$_2$—CO—(4-Me-Ph) | |
| 5-220 | Me | Et | Br | —CH$_2$—CO—(4-Me-Ph) | |
| 5-221 | CF$_3$ | Me | Br | —CH$_2$—CO—(4-Me-Ph) | |
| 5-222 | CF$_3$ | Et | Br | —CH$_2$—CO—(4-Me-Ph) | |
| 5-223 | OMe | Me | Br | —CH$_2$—CO—(4-Me-Ph) | |
| 5-224 | OMe | Et | Br | —CH$_2$—CO—(4-Me-Ph) | |
| 5-225 | NO$_2$ | Me | Br | —CH$_2$—CO—(4-Me-Ph) | |
| 5-226 | NO$_2$ | Et | Br | —CH$_2$—CO—(4-Me-Ph) | |
| 5-227 | SO$_2$Me | Me | Br | —CH$_2$—CO—(4-Me-Ph) | |
| 5-228 | SO$_2$Me | Et | Br | —CH$_2$—CO—(4-Me-Ph) | |
| 5-229 | CH$_2$OMe | Me | Br | —CH$_2$—CO—(4-Me-Ph) | |
| 5-230 | CH$_2$OMe | Et | Br | —CH$_2$—CO—(4-Me-Ph) | |
| 5-231 | CH$_2$SO$_2$Me | Me | Br | —CH$_2$—CO—(4-Me-Ph) | |
| 5-232 | CH$_2$SO$_2$Me | Et | Br | —CH$_2$—CO—(4-Me-Ph) | |
| 5-233 | CH$_2$OCH$_2$OMe | Me | Br | —CH$_2$—CO—(4-Me-Ph) | |

TABLE 5-continued

Compounds of the formula (I) according to the invention in which $R^1$ is methyl and $R^2$ is hydrogen.

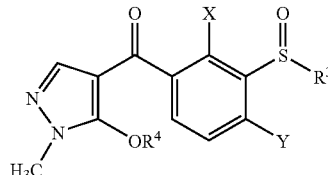

| No. | X | $R^3$ | Y | $R^4$ | Physical data: $^1$H-NMR: δ [CDCl$_3$] |
|---|---|---|---|---|---|
| 5-234 | CH$_2$OCH$_2$OMe | Et | Br | —CH$_2$—CO—(4-Me-Ph) | |
| 5-235 | Cl | Me | I | —CH$_2$—CO—(4-Me-Ph) | |
| 5-236 | Cl | Et | I | —CH$_2$—CO—(4-Me-Ph) | |
| 5-237 | Me | Me | I | —CH$_2$—CO—(4-Me-Ph) | |
| 5-238 | Me | Et | I | —CH$_2$—CO—(4-Me-Ph) | |
| 5-239 | CF$_3$ | Me | I | —CH$_2$—CO—(4-Me-Ph) | |
| 5-240 | CF$_3$ | Et | I | —CH$_2$—CO—(4-Me-Ph) | |
| 5-241 | OMe | Me | I | —CH$_2$—CO—(4-Me-Ph) | |
| 5-242 | OMe | Et | I | —CH$_2$—CO—(4-Me-Ph) | |
| 5-243 | NO$_2$ | Me | I | —CH$_2$—CO—(4-Me-Ph) | |
| 5-244 | NO$_2$ | Et | I | —CH$_2$—CO—(4-Me-Ph) | |
| 5-245 | SO$_2$Me | Me | I | —CH$_2$—CO—(4-Me-Ph) | |
| 5-246 | SO$_2$Me | Et | I | —CH$_2$—CO—(4-Me-Ph) | |
| 5-247 | CH$_2$OMe | Me | I | —CH$_2$—CO—(4-Me-Ph) | |
| 5-248 | CH$_2$OMe | Et | I | —CH$_2$—CO—(4-Me-Ph) | |
| 5-249 | CH$_2$SO$_2$Me | Me | I | —CH$_2$—CO—(4-Me-Ph) | |
| 5-250 | CH$_2$SO$_2$Me | Et | I | —CH$_2$—CO—(4-Me-Ph) | |
| 5-251 | CH$_2$OCH$_2$OMe | Me | I | —CH$_2$—CO—(4-Me-Ph) | |
| 5-252 | CH$_2$OCH$_2$OMe | Et | I | —CH$_2$—CO—(4-Me-Ph) | |
| 5-253 | Cl | Me | NO$_2$ | —CH$_2$—CO—(4-Me-Ph) | |
| 5-254 | Cl | Et | NO$_2$ | —CH$_2$—CO—(4-Me-Ph) | |
| 5-255 | Me | Me | NO$_2$ | —CH$_2$—CO—(4-Me-Ph) | |
| 5-256 | Me | Et | NO$_2$ | —CH$_2$—CO—(4-Me-Ph) | |
| 5-257 | CF$_3$ | Me | NO$_2$ | —CH$_2$—CO—(4-Me-Ph) | |
| 5-258 | CF$_3$ | Et | NO$_2$ | —CH$_2$—CO—(4-Me-Ph) | |
| 5-259 | OMe | Me | NO$_2$ | —CH$_2$—CO—(4-Me-Ph) | |
| 5-260 | OMe | Et | NO$_2$ | —CH$_2$—CO—(4-Me-Ph) | |
| 5-261 | NO$_2$ | Me | NO$_2$ | —CH$_2$—CO—(4-Me-Ph) | |
| 5-262 | NO$_2$ | Et | NO$_2$ | —CH$_2$—CO—(4-Me-Ph) | |
| 5-263 | SO$_2$Me | Me | NO$_2$ | —CH$_2$—CO—(4-Me-Ph) | |
| 5-264 | SO$_2$Me | Et | NO$_2$ | —CH$_2$—CO—(4-Me-Ph) | |
| 5-265 | CH$_2$OMe | Me | NO$_2$ | —CH$_2$—CO—(4-Me-Ph) | |

TABLE 5-continued

Compounds of the formula (I) according to the invention in which $R^1$ is methyl and $R^2$ is hydrogen.

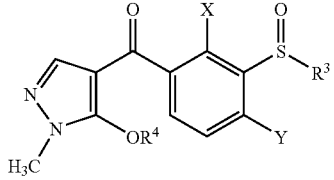

| No. | X | $R^3$ | Y | $R^4$ | Physical data: $^1$H-NMR: δ [CDCl$_3$] |
|---|---|---|---|---|---|
| 5-266 | CH$_2$OMe | Et | NO$_2$ | —CH$_2$—CO—(4-Me-Ph) | |
| 5-267 | CH$_2$SO$_2$Me | Me | NO$_2$ | —CH$_2$—CO—(4-Me-Ph) | |
| 5-268 | CH$_2$SO$_2$Me | Et | NO$_2$ | —CH$_2$—CO—(4-Me-Ph) | |
| 5-269 | CH$_2$OCH$_2$CH$_2$OMe | Me | NO$_2$ | —CH$_2$—CO—(4-Me-Ph) | |
| 5-270 | CH$_2$OCH$_2$CH$_2$OMe | Et | NO$_2$ | —CH$_2$—CO—(4-Me-Ph) | |

TABLE 6

Compounds of the formula (I) according to the invention in which $R^1$ is ethyl and $R^2$ is hydrogen.

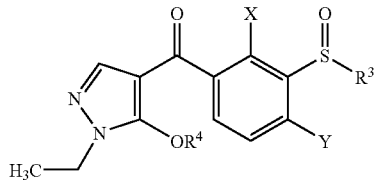
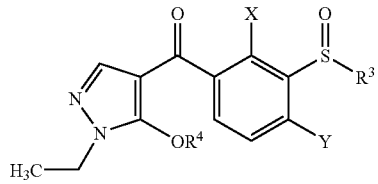

| No. | X | $R^3$ | Y | $R^4$ | Physical data: $^1$H-NMR: δ [CDCl$_3$] |
|---|---|---|---|---|---|
| 6-1 | Cl | Me | SO$_2$Me | —SO$_2$-n-Pr | |
| 6-2 | Cl | Et | SO$_2$Me | —SO$_2$-n-Pr | |
| 6-3 | Me | Me | SO$_2$Me | —SO$_2$-n-Pr | |
| 6-4 | Me | Et | SO$_2$Me | —SO$_2$-n-Pr | |
| 6-5 | CF$_3$ | Me | SO$_2$Me | —SO$_2$-n-Pr | |
| 6-6 | CF$_3$ | Et | SO$_2$Me | —SO$_2$-n-Pr | |
| 6-7 | OMe | Me | SO$_2$Me | —SO$_2$-n-Pr | |
| 6-8 | OMe | Et | SO$_2$Me | —SO$_2$-n-Pr | |
| 6-9 | NO$_2$ | Me | SO$_2$Me | —SO$_2$-n-Pr | |
| 6-10 | NO$_2$ | Et | SO$_2$Me | —SO$_2$-n-Pr | |
| 6-11 | SO$_2$Me | Me | SO$_2$Me | —SO$_2$-n-Pr | |
| 6-12 | SO$_2$Me | Et | SO$_2$Me | —SO$_2$-n-Pr | |
| 6-13 | CH$_2$OMe | Me | SO$_2$Me | —SO$_2$-n-Pr | |
| 6-14 | CH$_2$OMe | Et | SO$_2$Me | —SO$_2$-n-Pr | |
| 6-15 | CH$_2$SO$_2$Me | Me | SO$_2$Me | —SO$_2$-n-Pr | |
| 6-16 | CH$_2$SO$_2$Me | Et | SO$_2$Me | —SO$_2$-n-Pr | |
| 6-17 | CH$_2$OCH$_2$CH$_2$OMe | Me | SO$_2$Me | —SO$_2$-n-Pr | |
| 6-18 | CH$_2$OCH$_2$CH$_2$OMe | Et | SO$_2$Me | —SO$_2$-n-Pr | |
| 6-19 | Cl | Me | Cl | —SO$_2$-n-Pr | |
| 6-20 | Cl | Et | Cl | —SO$_2$-n-Pr | |
| 6-21 | Me | Me | Cl | —SO$_2$-n-Pr | |
| 6-22 | Me | Et | Cl | —SO$_2$-n-Pr | |
| 6-23 | CF$_3$ | Me | Cl | —SO$_2$-n-Pr | |
| 6-24 | CF$_3$ | Et | Cl | —SO$_2$-n-Pr | |
| 6-25 | OMe | Me | Cl | —SO$_2$-n-Pr | |
| 6-26 | OMe | Et | Cl | —SO$_2$-n-Pr | |
| 6-27 | NO$_2$ | Me | Cl | —SO$_2$-n-Pr | |
| 6-28 | NO$_2$ | Et | Cl | —SO$_2$-n-Pr | |
| 6-29 | SO$_2$Me | Me | Cl | —SO$_2$-n-Pr | |
| 6-30 | SO$_2$Me | Et | Cl | —SO$_2$-n-Pr | |
| 6-31 | CH$_2$OMe | Me | Cl | —SO$_2$-n-Pr | |
| 6-32 | CH$_2$OMe | Et | Cl | —SO$_2$-n-Pr | |
| 6-33 | CH$_2$SO$_2$Me | Me | Cl | —SO$_2$-n-Pr | |
| 6-34 | CH$_2$SO$_2$Me | Et | Cl | —SO$_2$-n-Pr | |
| 6-35 | CH$_2$OCH$_2$CH$_2$OMe | Me | Cl | —SO$_2$-n-Pr | |
| 6-36 | CH$_2$OCH$_2$CH$_2$OMe | Et | Cl | —SO$_2$-n-Pr | |
| 6-37 | Cl | Me | Br | —SO$_2$-n-Pr | |
| 6-38 | Cl | Et | Br | —SO$_2$-n-Pr | |
| 6-39 | Me | Me | Br | —SO$_2$-n-Pr | |
| 6-40 | Me | Et | Br | —SO$_2$-n-Pr | |
| 6-41 | CF$_3$ | Me | Br | —SO$_2$-n-Pr | |
| 6-42 | CF$_3$ | Et | Br | —SO$_2$-n-Pr | |
| 6-43 | OMe | Me | Br | —SO$_2$-n-Pr | |
| 6-44 | OMe | Et | Br | —SO$_2$-n-Pr | |
| 6-45 | NO$_2$ | Me | Br | —SO$_2$-n-Pr | |
| 6-46 | NO$_2$ | Et | Br | —SO$_2$-n-Pr | |
| 6-47 | SO$_2$Me | Me | Br | —SO$_2$-n-Pr | |
| 6-48 | SO$_2$Me | Et | Br | —SO$_2$-n-Pr | |
| 6-49 | CH$_2$OMe | Me | Br | —SO$_2$-n-Pr | |
| 6-50 | CH$_2$OMe | Et | Br | —SO$_2$-n-Pr | |
| 6-51 | CH$_2$SO$_2$Me | Me | Br | —SO$_2$-n-Pr | |
| 6-52 | CH$_2$SO$_2$Me | Et | Br | —SO$_2$-n-Pr | |
| 6-53 | CH$_2$OCH$_2$CH$_2$OMe | Me | Br | —SO$_2$-n-Pr | |
| 6-54 | CH$_2$OCH$_2$CH$_2$OMe | Et | Br | —SO$_2$-n-Pr | |
| 6-55 | Cl | Me | I | —SO$_2$-n-Pr | |
| 6-56 | Cl | Et | I | —SO$_2$-n-Pr | |
| 6-57 | Me | Me | I | —SO$_2$-n-Pr | |
| 6-58 | Me | Et | I | —SO$_2$-n-Pr | |
| 6-59 | CF$_3$ | Me | I | —SO$_2$-n-Pr | |
| 6-60 | CF$_3$ | Et | I | —SO$_2$-n-Pr | |
| 6-61 | OMe | Me | I | —SO$_2$-n-Pr | |
| 6-62 | OMe | Et | I | —SO$_2$-n-Pr | |

TABLE 6-continued

Compounds of the formula (I) according to the invention in which $R^1$ is ethyl and $R^2$ is hydrogen.

| No. | X | $R^3$ | Y | $R^4$ | Physical data: $^1$H-NMR: δ [CDCl$_3$] |
|---|---|---|---|---|---|
| 6-63 | NO$_2$ | Me | I | —SO$_2$-n-Pr | |
| 6-64 | NO$_2$ | Et | I | —SO$_2$-n-Pr | |
| 6-65 | SO$_2$Me | Me | I | —SO$_2$-n-Pr | |
| 6-66 | SO$_2$Me | Et | I | —SO$_2$-n-Pr | |
| 6-67 | CH$_2$OMe | Me | I | —SO$_2$-n-Pr | |
| 6-68 | CH$_2$OMe | Et | I | —SO$_2$-n-Pr | |
| 6-69 | CH$_2$SO$_2$Me | Me | I | —SO$_2$-n-Pr | |
| 6-70 | CH$_2$SO$_2$Me | Et | I | —SO$_2$-n-Pr | |
| 6-71 | CH$_2$OCH$_2$CH$_2$OMe | Me | I | —SO$_2$-n-Pr | |
| 6-72 | CH$_2$OCH$_2$CH$_2$OMe | Et | I | —SO$_2$-n-Pr | |
| 6-73 | Cl | Me | NO$_2$ | —SO$_2$-n-Pr | |
| 6-74 | Cl | Et | NO$_2$ | —SO$_2$-n-Pr | |
| 6-75 | Me | Me | NO$_2$ | —SO$_2$-n-Pr | |
| 6-76 | Me | Et | NO$_2$ | —SO$_2$-n-Pr | |
| 6-77 | CF$_3$ | Me | NO$_2$ | —SO$_2$-n-Pr | |
| 6-78 | CF$_3$ | Et | NO$_2$ | —SO$_2$-n-Pr | |
| 6-79 | OMe | Me | NO$_2$ | —SO$_2$-n-Pr | |
| 6-80 | OMe | Et | NO$_2$ | —SO$_2$-n-Pr | |
| 6-81 | NO$_2$ | Me | NO$_2$ | —SO$_2$-n-Pr | |
| 6-82 | NO$_2$ | Et | NO$_2$ | —SO$_2$-n-Pr | |
| 6-83 | SO$_2$Me | Me | NO$_2$ | —SO$_2$-n-Pr | |
| 6-84 | SO$_2$Me | Et | NO$_2$ | —SO$_2$-n-Pr | |
| 6-85 | CH$_2$OMe | Me | NO$_2$ | —SO$_2$-n-Pr | |
| 6-86 | CH$_2$OMe | Et | NO$_2$ | —SO$_2$-n-Pr | |
| 6-87 | CH$_2$SO$_2$Me | Me | NO$_2$ | —SO$_2$-n-Pr | |
| 6-88 | CH$_2$SO$_2$Me | Et | NO$_2$ | —SO$_2$-n-Pr | |
| 6-89 | CH$_2$OCH$_2$CH$_2$OMe | Me | NO2 | —SO$_2$-n-Pr | |
| 6-90 | CH$_2$OCH$_2$CH$_2$OMe | Et | NO$_2$ | —SO$_2$-n-Pr | |
| 6-91 | Cl | Me | SO$_2$Me | —CO-Ph | |
| 6-92 | Cl | Et | SO$_2$Me | —CO-Ph | |
| 6-93 | Me | Me | SO$_2$Me | —CO-Ph | |
| 6-94 | Me | Et | SO$_2$Me | —CO-Ph | |
| 6-95 | CF$_3$ | Me | SO$_2$Me | —CO-Ph | |
| 6-96 | CF$_3$ | Et | SO$_2$Me | —CO-Ph | |
| 6-97 | OMe | Me | SO$_2$Me | —CO-Ph | |
| 6-98 | OMe | Et | SO$_2$Me | —CO-Ph | |
| 6-99 | NO$_2$ | Me | SO$_2$Me | —CO-Ph | |
| 6-100 | NO$_2$ | Et | SO$_2$Me | —CO-Ph | |
| 6-101 | SO$_2$Me | Me | SO$_2$Me | —CO-Ph | |
| 6-102 | SO$_2$Me | Et | SO$_2$Me | —CO-Ph | |
| 6-103 | CH$_2$OMe | Me | SO$_2$Me | —CO-Ph | |
| 6-104 | CH$_2$OMe | Et | SO$_2$Me | —CO-Ph | |
| 6-105 | CH$_2$SO$_2$Me | Me | SO$_2$Me | —CO-Ph | |
| 6-106 | CH$_2$SO$_2$Me | Et | SO$_2$Me | —CO-Ph | |
| 6-107 | CH$_2$OCH$_2$CH$_2$OMe | Me | SO$_2$Me | —CO-Ph | |
| 6-108 | CH$_2$OCH$_2$CH$_2$OMe | Et | SO$_2$Me | —CO-Ph | |
| 6-109 | Cl | Me | Cl | —CO-Ph | |
| 6-110 | Cl | Et | Cl | —CO-Ph | |
| 6-111 | Me | Me | Cl | —CO-Ph | |
| 6-112 | Me | Et | Cl | —CO-Ph | |
| 6-113 | CF$_3$ | Me | Cl | —CO-Ph | |
| 6-114 | CF$_3$ | Et | Cl | —CO-Ph | |
| 6-115 | OMe | Me | Cl | —CO-Ph | |
| 6-116 | OMe | Et | Cl | —CO-Ph | |
| 6-117 | NO$_2$ | Me | Cl | —CO-Ph | |
| 6-118 | NO$_2$ | Et | Cl | —CO-Ph | |
| 6-119 | SO$_2$Me | Me | Cl | —CO-Ph | |
| 6-120 | SO$_2$Me | Et | Cl | —CO-Ph | |
| 6-121 | CH$_2$OMe | Me | Cl | —CO-Ph | |
| 6-122 | CH$_2$OMe | Et | Cl | —CO-Ph | |
| 6-123 | CH$_2$SO$_2$Me | Me | Cl | —CO-Ph | |
| 6-124 | CH$_2$SO$_2$Me | Et | Cl | —CO-Ph | |
| 6-125 | CH$_2$OCH$_2$CH$_2$OMe | Me | Cl | —CO-Ph | |
| 6-126 | CH$_2$OCH$_2$CH$_2$OMe | Et | Cl | —CO-Ph | |
| 6-127 | Cl | Me | Br | —CO-Ph | |
| 6-128 | Cl | Et | Br | —CO-Ph | |
| 6-129 | Me | Me | Br | —CO-Ph | |
| 6-130 | Me | Et | Br | —CO-Ph | |
| 6-131 | CF$_3$ | Me | Br | —CO-Ph | |
| 6-132 | CF$_3$ | Et | Br | —CO-Ph | |
| 6-133 | OMe | Me | Br | —CO-Ph | |
| 6-134 | OMe | Et | Br | —CO-Ph | |
| 6-135 | NO$_2$ | Me | Br | —CO-Ph | |
| 6-136 | NO$_2$ | Et | Br | —CO-Ph | |
| 6-137 | SO$_2$Me | Me | Br | —CO-Ph | |
| 6-138 | SO$_2$Me | Et | Br | —CO-Ph | |
| 6-139 | CH$_2$OMe | Me | Br | —CO-Ph | |
| 6-140 | CH$_2$OMe | Et | Br | —CO-Ph | |
| 6-141 | CH$_2$SO$_2$Me | Me | Br | —CO-Ph | |
| 6-142 | CH$_2$SO$_2$Me | Et | Br | —CO-Ph | |
| 6-143 | CH$_2$OCH$_2$CH$_2$OMe | Me | Br | —CO-Ph | |
| 6-144 | CH$_2$OCH$_2$CH$_2$OMe | Et | Br | —CO-Ph | |
| 6-145 | Cl | Me | I | —CO-Ph | |
| 6-146 | Cl | Et | I | —CO-Ph | |
| 6-147 | Me | Me | I | —CO-Ph | |
| 6-148 | Me | Et | I | —CO-Ph | |
| 6-149 | CF$_3$ | Me | I | —CO-Ph | |
| 6-150 | CF$_3$ | Et | I | —CO-Ph | |
| 6-151 | OMe | Me | I | —CO-Ph | |
| 6-152 | OMe | Et | I | —CO-Ph | |
| 6-153 | NO$_2$ | Me | I | —CO-Ph | |
| 6-154 | NO$_2$ | Et | I | —CO-Ph | |
| 6-155 | SO$_2$Me | Me | I | —CO-Ph | |
| 6-156 | SO$_2$Me | Et | I | —CO-Ph | |
| 6-157 | CH$_2$OMe | Me | I | —CO-Ph | |
| 6-158 | CH$_2$OMe | Et | I | —CO-Ph | |
| 6-159 | CH$_2$SO$_2$Me | Me | I | —CO-Ph | |
| 6-160 | CH$_2$SO$_2$Me | Et | I | —CO-Ph | |
| 6-161 | CH$_2$OCH$_2$CH$_2$OMe | Me | I | —CO-Ph | |
| 6-162 | CH$_2$OCH$_2$CH$_2$OMe | Et | I | —CO-Ph | |
| 6-163 | Cl | Me | NO$_2$ | —CO-Ph | |
| 6-164 | Cl | Et | NO$_2$ | —CO-Ph | |
| 6-165 | Me | Me | NO$_2$ | —CO-Ph | |
| 6-166 | Me | Et | NO$_2$ | —CO-Ph | |
| 6-167 | CF$_3$ | Me | NO$_2$ | —CO-Ph | |
| 6-168 | CF$_3$ | Et | NO$_2$ | —CO-Ph | |
| 6-169 | OMe | Me | NO$_2$ | —CO-Ph | |
| 6-170 | OMe | Et | NO$_2$ | —CO-Ph | |
| 6-171 | NO$_2$ | Me | NO$_2$ | —CO-Ph | |
| 6-172 | NO$_2$ | Et | NO$_2$ | —CO-Ph | |
| 6-173 | SO$_2$Me | Me | NO$_2$ | —CO-Ph | |
| 6-174 | SO$_2$Me | Et | NO$_2$ | —CO-Ph | |
| 6-175 | CH$_2$OMe | Me | NO$_2$ | —CO-Ph | |
| 6-176 | CH$_2$OMe | Et | NO$_2$ | —CO-Ph | |
| 6-177 | CH$_2$SO$_2$Me | Me | NO$_2$ | —CO-Ph | |
| 6-178 | CH$_2$SO$_2$Me | Et | NO$_2$ | —CO-Ph | |
| 6-179 | CH$_2$OCH$_2$CH$_2$OMe | Me | NO$_2$ | —CO-Ph | |
| 6-180 | CH$_2$OCH$_2$CH$_2$OMe | Et | NO$_2$ | —CO-Ph | |
| 6-181 | Cl | Me | SO$_2$Me | CH$_2$—CO-(4-Me-Ph) | |
| 6-182 | Cl | Et | SO$_2$Me | CH$_2$—CO-(4-Me-Ph) | |
| 6-183 | Me | Me | SO$_2$Me | CH$_2$—CO-(4-Me-Ph) | |

TABLE 6-continued

Compounds of the formula (I) according to the invention in which R¹ is ethyl and R² is hydrogen.

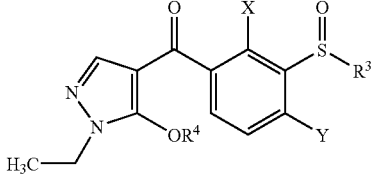

| No. | X | R³ | Y | R⁴ | Physical data: ¹H-NMR: δ [CDCl₃] |
|---|---|---|---|---|---|
| 6-184 | Me | Et | SO₂Me | CH₂—CO-(4-Me-Ph) | |
| 6-185 | CF₃ | Me | SO₂Me | CH₂—CO-(4-Me-Ph) | |
| 6-186 | CF₃ | Et | SO₂Me | CH₂—CO-(4-Me-Ph) | |
| 6-187 | OMe | Me | SO₂Me | CH₂—CO-(4-Me-Ph) | |
| 6-188 | OMe | Et | SO₂Me | CH₂—CO-(4-Me-Ph) | |
| 6-189 | NO₂ | Me | SO₂Me | CH₂—CO-(4-Me-Ph) | |
| 6-190 | NO₂ | Et | SO₂Me | —CH₂—CO-(4-Me-Ph) | |
| 6-191 | SO₂Me | Me | SO₂Me | —CH₂—CO-(4-Me-Ph) | |
| 6-192 | SO₂Me | Et | SO₂Me | —CH₂—CO-(4-Me-Ph) | |
| 6-193 | CH₂OMe | Me | SO₂Me | —CH₂—CO-(4-Me-Ph) | |
| 6-194 | CH₂OMe | Et | SO₂Me | —CH₂—CO-(4-Me-Ph) | |
| 6-195 | CH₂SO₂Me | Me | SO₂Me | —CH₂—CO-(4-Me-Ph) | |
| 6-196 | CH₂SO₂Me | Et | SO₂Me | —CH₂—CO-(4-Me-Ph) | |
| 6-197 | CH₂OCH₂CH₂OMe | Me | SO₂Me | —CH₂—CO-(4-Me-Ph) | |
| 6-198 | CH₂OCH₂CH₂OMe | Et | SO₂Me | —CH₂—CO-(4-Me-Ph) | |
| 6-199 | Cl | Me | Cl | —CH₂—CO-(4-Me-Ph) | |
| 6-200 | Cl | Et | Cl | —CH₂—CO-(4-Me-Ph) | |
| 6-201 | Me | Me | Cl | —CH₂—CO-(4-Me-Ph) | |
| 6-202 | Me | Et | Cl | —CH₂—CO-(4-Me-Ph) | |
| 6-203 | CF₃ | Me | Cl | —CH₂—CO-(4-Me-Ph) | |
| 6-204 | CF₃ | Et | Cl | —CH₂—CO-(4-Me-Ph) | |
| 6-205 | OMe | Me | Cl | —CH₂—CO-(4-Me-Ph) | |
| 6-206 | OMe | Et | Cl | —CH₂—CO-(4-Me-Ph) | |
| 6-207 | NO₂ | Me | Cl | —CH₂—CO-(4-Me-Ph) | |
| 6-208 | NO₂ | Et | Cl | —CH₂—CO-(4-Me-Ph) | |
| 6-209 | SO₂Me | Me | Cl | —CH₂—CO-(4-Me-Ph) | |
| 6-210 | SO₂Me | Et | Cl | —CH₂—CO-(4-Me-Ph) | |
| 6-211 | CH₂OMe | Me | Cl | —CH₂—CO-(4-Me-Ph) | |
| 6-212 | CH₂OMe | Et | Cl | —CH₂—CO-(4-Me-Ph) | |
| 6-213 | CH₂SO₂Me | Me | Cl | —CH₂—CO-(4-Me-Ph) | |
| 6-214 | CH₂SO₂Me | Et | Cl | —CH₂—CO-(4-Me-Ph) | |
| 6-215 | CH₂OCH₂CH₂OMe | Me | Cl | —CH₂—CO-(4-Me-Ph) | |
| 6-216 | CH₂OCH₂CH₂OMe | Et | Cl | —CH₂—CO-(4-Me-Ph) | |
| 6-217 | Cl | Me | Br | —CH₂—CO-(4-Me-Ph) | |
| 6-218 | Cl | Et | Br | —CH₂—CO-(4-Me-Ph) | |
| 6-219 | Me | Me | Br | —CH₂—CO-(4-Me-Ph) | |
| 6-220 | Me | Et | Br | —CH₂—CO-(4-Me-Ph) | |
| 6-221 | CF₃ | Me | Br | —CH₂—CO-(4-Me-Ph) | |
| 6-222 | CF₃ | Et | Br | —CH₂—CO-(4-Me-Ph) | |
| 6-223 | OMe | Me | Br | —CH₂—CO-(4-Me-Ph) | |
| 6-224 | OMe | Et | Br | —CH₂—CO-(4-Me-Ph) | |
| 6-225 | NO₂ | Me | Br | —CH₂—CO-(4-Me-Ph) | |
| 6-226 | NO₂ | Et | Br | —CH₂—CO-(4-Me-Ph) | |
| 6-227 | SO₂Me | Me | Br | —CH₂—CO-(4-Me-Ph) | |
| 6-228 | SO₂Me | Et | Br | —CH₂—CO-(4-Me-Ph) | |
| 6-229 | CH₂OMe | Me | Br | —CH₂—CO-(4-Me-Ph) | |
| 6-230 | CH₂OMe | Et | Br | —CH₂—CO-(4-Me-Ph) | |
| 6-231 | CH₂SO₂Me | Me | Br | —CH₂—CO-(4-Me-Ph) | |
| 6-232 | CH₂SO₂Me | Et | Br | —CH₂—CO-(4-Me-Ph) | |
| 6-233 | CH₂OCH₂CH₂OMe | Me | Br | —CH₂—CO-(4-Me-Ph) | |
| 6-234 | CH₂OCH₂CH₂OMe | Et | Br | —CH₂—CO-(4-Me-Ph) | |
| 6-235 | Cl | Me | I | —CH₂—CO-(4-Me-Ph) | |
| 6-236 | Cl | Et | I | —CH₂—CO-(4-Me-Ph) | |
| 6-237 | Me | Me | I | —CH₂—CO-(4-Me-Ph) | |
| 6-238 | Me | Et | I | —CH₂—CO-(4-Me-Ph) | |
| 6-239 | CF₃ | Me | I | —CH₂—CO-(4-Me-Ph) | |
| 6-240 | CF₃ | Et | I | —CH₂—CO-(4-Me-Ph) | |
| 6-241 | OMe | Me | I | —CH₂—CO-(4-Me-Ph) | |
| 6-242 | OMe | Et | I | —CH₂—CO-(4-Me-Ph) | |
| 6-243 | NO₂ | Me | I | —CH₂—CO-(4-Me-Ph) | |
| 6-244 | NO₂ | Et | I | —CH₂—CO-(4-Me-Ph) | |
| 6-245 | SO₂Me | Me | I | —CH₂—CO-(4-Me-Ph) | |

TABLE 6-continued

Compounds of the formula (I) according to the invention in which $R^1$ is ethyl and $R^2$ is hydrogen.

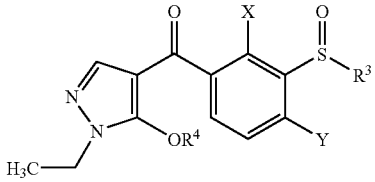

| No. | X | $R^3$ | Y | $R^4$ | Physical data: $^1$H-NMR: δ [CDCl$_3$] |
|---|---|---|---|---|---|
| 6-246 | SO$_2$Me | Et | I | —CH$_2$—CO-(4-Me-Ph) | |
| 6-247 | CH$_2$OMe | Me | I | —CH$_2$—CO-(4-Me-Ph) | |
| 6-248 | CH$_2$OMe | Et | I | —CH$_2$—CO-(4-Me-Ph) | |
| 6-249 | CH$_2$SO$_2$Me | Me | I | —CH$_2$—CO-(4-Me-Ph) | |
| 6-250 | CH$_2$SO$_2$Me | Et | I | —CH$_2$—CO-(4-Me-Ph) | |
| 6-251 | CH$_2$OCH$_2$CH$_2$OMe | Me | I | —CH$_2$—CO-(4-Me-Ph) | |
| 6-252 | CH$_2$OCH$_2$CH$_2$OMe | Et | I | —CH$_2$—CO-(4-Me-Ph) | |
| 6-253 | Cl | Me | NO$_2$ | —CH$_2$—CO-(4-Me-Ph) | |
| 6-254 | Cl | Et | NO$_2$ | —CH$_2$—CO-(4-Me-Ph) | |
| 6-255 | Me | Me | NO$_2$ | —CH$_2$—CO-(4-Me-Ph) | |
| 6-256 | Me | Et | NO$_2$ | —CH$_2$—CO-(4-Me-Ph) | |
| 6-257 | CF$_3$ | Me | NO$_2$ | —CH$_2$—CO-(4-Me-Ph) | |
| 6-258 | CF$_3$ | Et | NO$_2$ | —CH$_2$—CO-(4-Me-Ph) | |
| 6-259 | OMe | Me | NO$_2$ | —CH$_2$—CO-(4-Me-Ph) | |
| 6-260 | OMe | Et | NO$_2$ | —CH$_2$—CO-(4-Me-Ph) | |
| 6-261 | NO$_2$ | Me | NO$_2$ | —CH$_2$—CO-(4-Me-Ph) | |
| 6-262 | NO$_2$ | Et | NO$_2$ | —CH$_2$—CO-(4-Me-Ph) | |
| 6-263 | SO$_2$Me | Me | NO$_2$ | —CH$_2$—CO-(4-Me-Ph) | |
| 6-264 | SO$_2$Me | Et | NO$_2$ | —CH$_2$—CO-(4-Me-Ph) | |
| 6-265 | CH$_2$OMe | Me | NO$_2$ | —CH$_2$—CO-(4-Me-Ph) | |
| 6-266 | CH$_2$OMe | Et | NO$_2$ | —CH$_2$—CO-(4-Me-Ph) | |
| 6-267 | CH$_2$SO$_2$Me | Me | NO$_2$ | —CH$_2$—CO-(4-Me-Ph) | |
| 6-268 | CH$_2$SO$_2$Me | Et | NO$_2$ | —CH$_2$—CO-(4-Me-Ph) | |
| 6-269 | CH$_2$OCH$_2$CH$_2$OMe | Me | NO$_2$ | —CH$_2$—CO-(4-Me-Ph) | |
| 6-270 | CH$_2$OCH$_2$CH$_2$OMe | Et | NO$_2$ | —CH$_2$—CO-(4-Me-Ph) | |

TABLE 7

Compounds of the formula (I) according to the invention in which $R^1$ and $R^2$ are each methyl.

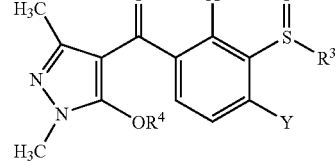

| No. | X | $R^3$ | Y | $R^4$ | Physical data: $^1$H-NMR: δ [CDCl$_3$] |
|---|---|---|---|---|---|
| 7-1 | Cl | Me | SO$_2$Me | —SO$_2$-n-Pr | |
| 7-2 | Cl | Et | SO$_2$Me | —SO$_2$-n-Pr | |
| 7-3 | Me | Me | SO$_2$Me | —SO$_2$-n-Pr | |
| 7-4 | Me | Et | SO$_2$Me | —SO$_2$-n-Pr | |
| 7-5 | CF$_3$ | Me | SO$_2$Me | —SO$_2$-n-Pr | |
| 7-6 | CF$_3$ | Et | SO$_2$Me | —SO$_2$-n-Pr | |
| 7-7 | OMe | Me | SO$_2$Me | —SO$_2$-n-Pr | |
| 7-8 | OMe | Et | SO$_2$Me | —SO$_2$-n-Pr | |
| 7-9 | NO$_2$ | Me | SO$_2$Me | —SO$_2$-n-Pr | |
| 7-10 | NO$_2$ | Et | SO$_2$Me | —SO$_2$-n-Pr | |
| 7-11 | SO$_2$Me | Me | SO$_2$Me | —SO$_2$-n-Pr | |
| 7-12 | SO$_2$Me | Et | SO$_2$Me | —SO$_2$-n-Pr | |
| 7-13 | CH$_2$OMe | Me | SO$_2$Me | —SO$_2$-n-Pr | |
| 7-14 | CH$_2$OMe | Et | SO$_2$Me | —SO$_2$-n-Pr | |
| 7-15 | CH$_2$SO$_2$Me | Me | SO$_2$Me | —SO$_2$-n-Pr | |
| 7-16 | CH$_2$SO$_2$Me | Et | SO$_2$Me | —SO$_2$-n-Pr | |
| 7-17 | CH$_2$OCH$_2$CH$_2$OMe | Me | SO$_2$Me | —SO$_2$-n-Pr | |
| 7-18 | CH$_2$OCH$_2$CH$_2$OMe | Et | SO$_2$Me | —SO$_2$-n-Pr | |
| 7-19 | Cl | Me | Cl | —SO$_2$-n-Pr | |
| 7-20 | Cl | Et | Cl | —SO$_2$-n-Pr | |
| 7-21 | Me | Me | Cl | —SO$_2$-n-Pr | |
| 7-22 | Me | Et | Cl | —SO$_2$-n-Pr | |
| 7-23 | CF$_3$ | Me | Cl | —SO$_2$-n-Pr | |
| 7-24 | CF$_3$ | Et | Cl | —SO$_2$-n-Pr | |
| 7-25 | OMe | Me | Cl | —SO$_2$-n-Pr | |
| 7-26 | OMe | Et | Cl | —SO$_2$-n-Pr | |
| 7-27 | NO$_2$ | Me | Cl | —SO$_2$-n-Pr | |
| 7-28 | NO$_2$ | Et | Cl | —SO$_2$-n-Pr | |
| 7-29 | SO$_2$Me | Me | Cl | —SO$_2$-n-Pr | |
| 7-30 | SO$_2$Me | Et | Cl | —SO$_2$-n-Pr | |
| 7-31 | CH$_2$OMe | Me | Cl | —SO$_2$-n-Pr | |
| 7-32 | CH$_2$OMe | Et | Cl | —SO$_2$-n-Pr | |
| 7-33 | CH$_2$SO$_2$Me | Me | Cl | —SO$_2$-n-Pr | |
| 7-34 | CH$_2$SO$_2$Me | Et | Cl | —SO$_2$-n-Pr | |
| 7-35 | CH$_2$OCH$_2$CH$_2$OMe | Me | Cl | —SO$_2$-n-Pr | |
| 7-36 | CH$_2$OCH$_2$CH$_2$OMe | Et | Cl | —SO$_2$-n-Pr | |
| 7-37 | Cl | Me | Br | —SO$_2$-n-Pr | |
| 7-38 | Cl | Et | Br | —SO$_2$-n-Pr | |
| 7-39 | Me | Me | Br | —SO$_2$-n-Pr | |
| 7-40 | Me | Et | Br | —SO$_2$-n-Pr | |
| 7-41 | CF$_3$ | Me | Br | —SO$_2$-n-Pr | |
| 7-42 | CF$_3$ | Et | Br | —SO$_2$-n-Pr | |
| 7-43 | OMe | Me | Br | —SO$_2$-n-Pr | |
| 7-44 | OMe | Et | Br | —SO$_2$-n-Pr | |
| 7-45 | NO$_2$ | Me | Br | —SO$_2$-n-Pr | |
| 7-46 | NO$_2$ | Et | Br | —SO$_2$-n-Pr | |
| 7-47 | SO$_2$Me | Me | Br | —SO$_2$-n-Pr | |
| 7-48 | SO$_2$Me | Et | Br | —SO$_2$-n-Pr | |
| 7-49 | CH$_2$OMe | Me | Br | —SO$_2$-n-Pr | |
| 7-50 | CH$_2$OMe | Et | Br | —SO$_2$-n-Pr | |
| 7-51 | CH$_2$SO$_2$Me | Me | Br | —SO$_2$-n-Pr | |
| 7-52 | CH$_2$SO$_2$Me | Et | Br | —SO$_2$-n-Pr | |
| 7-53 | CH$_2$OCH$_2$CH$_2$OMe | Me | Br | —SO$_2$-n-Pr | |
| 7-54 | CH$_2$OCH$_2$CH$_2$OMe | Et | Br | —SO$_2$-n-Pr | |
| 7-55 | Cl | Me | I | —SO$_2$-n-Pr | |
| 7-56 | Cl | Et | I | —SO$_2$-n-Pr | |
| 7-57 | Me | Me | I | —SO$_2$-n-Pr | |
| 7-58 | Me | Et | I | —SO$_2$-n-Pr | |
| 7-59 | CF$_3$ | Me | I | —SO$_2$-n-Pr | |
| 7-60 | CF$_3$ | Et | I | —SO$_2$-n-Pr | |
| 7-61 | OMe | Me | I | —SO$_2$-n-Pr | |
| 7-62 | OMe | Et | I | —SO$_2$-n-Pr | |

TABLE 7-continued

Compounds of the formula (I) according to the invention in which $R^1$ and $R^2$ are each methyl.

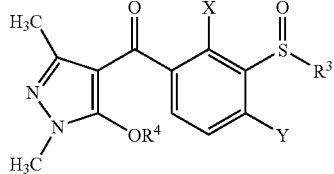

| No. | X | $R^3$ | Y | $R^4$ | Physical data: $^1$H-NMR: δ [CDCl$_3$] |
|---|---|---|---|---|---|
| 7-63 | NO$_2$ | Me | I | —SO$_2$-n-Pr | |
| 7-64 | NO$_2$ | Et | I | —SO$_2$-n-Pr | |
| 7-65 | SO$_2$Me | Me | I | —SO$_2$-n-Pr | |
| 7-66 | SO$_2$Me | Et | I | —SO$_2$-n-Pr | |
| 7-67 | CH$_2$OMe | Me | I | —SO$_2$-n-Pr | |
| 7-68 | CH$_2$OMe | Et | I | —SO$_2$-n-Pr | |
| 7-69 | CH$_2$SO$_2$Me | Me | I | —SO$_2$-n-Pr | |
| 7-70 | CH$_2$SO$_2$Me | Et | I | —SO$_2$-n-Pr | |
| 7-71 | CH$_2$OCH$_2$CH$_2$OMe | Me | I | —SO$_2$-n-Pr | |
| 7-72 | CH$_2$OCH$_2$CH$_2$OMe | Et | I | —SO$_2$-n-Pr | |
| 7-73 | Cl | Me | NO$_2$ | —SO$_2$-n-Pr | |
| 7-74 | Cl | Et | NO$_2$ | —SO$_2$-n-Pr | |
| 7-75 | Me | Me | NO$_2$ | —SO$_2$-n-Pr | |
| 7-76 | Me | Et | NO$_2$ | —SO$_2$-n-Pr | |
| 7-77 | CF$_3$ | Me | NO$_2$ | —SO$_2$-n-Pr | |
| 7-78 | CF$_3$ | Et | NO$_2$ | —SO$_2$-n-Pr | |
| 7-79 | OMe | Me | NO$_2$ | —SO$_2$-n-Pr | |
| 7-80 | OMe | Et | NO$_2$ | —SO$_2$-n-Pr | |
| 7-81 | NO$_2$ | Me | NO$_2$ | —SO$_2$-n-Pr | |
| 7-82 | NO$_2$ | Et | NO$_2$ | —SO$_2$-n-Pr | |
| 7-83 | SO$_2$Me | Me | NO$_2$ | —SO$_2$-n-Pr | |
| 7-84 | SO$_2$Me | Et | NO$_2$ | —SO$_2$-n-Pr | |
| 7-85 | CH$_2$OMe | Me | NO$_2$ | —SO$_2$-n-Pr | |
| 7-86 | CH$_2$OMe | Et | NO$_2$ | —SO$_2$-n-Pr | |
| 7-87 | CH$_2$SO$_2$Me | Me | NO$_2$ | —SO$_2$-n-Pr | |
| 7-88 | CH$_2$SO$_2$Me | Et | NO$_2$ | —SO$_2$-n-Pr | |
| 7-89 | CH$_2$OCH$_2$CH$_2$OMe | Me | NO$_2$ | —SO$_2$-n-Pr | |
| 7-90 | CH$_2$OCH$_2$CH$_2$OMe | Et | NO$_2$ | —SO$_2$-n-Pr | |
| 7-91 | Cl | Me | SO$_2$Me | —CO-Ph | |
| 7-92 | Cl | Et | SO$_2$Me | —CO-Ph | |
| 7-93 | Me | Me | SO$_2$Me | —CO-Ph | |
| 7-94 | Me | Et | SO$_2$Me | —CO-Ph | |
| 7-95 | CF$_3$ | Me | SO$_2$Me | —CO-Ph | |
| 7-96 | CF$_3$ | Et | SO$_2$Me | —CO-Ph | |
| 7-97 | OMe | Me | SO$_2$Me | —CO-Ph | |
| 7-98 | OMe | Et | SO$_2$Me | —CO-Ph | |
| 7-99 | NO$_2$ | Me | SO$_2$Me | —CO-Ph | |
| 7-100 | NO$_2$ | Et | SO$_2$Me | —CO-Ph | |
| 7-101 | SO$_2$Me | Me | SO$_2$Me | —CO-Ph | |
| 7-102 | SO$_2$Me | Et | SO$_2$Me | —CO-Ph | |
| 7-103 | CH$_2$OMe | Me | SO$_2$Me | —CO-Ph | |
| 7-104 | CH$_2$OMe | Et | SO$_2$Me | —CO-Ph | |
| 7-105 | CH$_2$SO$_2$Me | Me | SO$_2$Me | —CO-Ph | |
| 7-106 | CH$_2$SO$_2$Me | Et | SO$_2$Me | —CO-Ph | |
| 7-107 | CH$_2$OCH$_2$CH$_2$OMe | Me | SO$_2$Me | —CO-Ph | |
| 7-108 | CH$_2$OCH$_2$CH$_2$OMe | Et | SO$_2$Me | —CO-Ph | |
| 7-109 | Cl | Me | Cl | —CO-Ph | |
| 7-110 | Cl | Et | Cl | —CO-Ph | |
| 7-111 | Me | Me | Cl | —CO-Ph | |
| 7-112 | Me | Et | Cl | —CO-Ph | |
| 7-113 | CF$_3$ | Me | Cl | —CO-Ph | |
| 7-114 | CF$_3$ | Et | Cl | —CO-Ph | |
| 7-115 | OMe | Me | Cl | —CO-Ph | |
| 7-116 | OMe | Et | Cl | —CO-Ph | |
| 7-117 | NO$_2$ | Me | Cl | —CO-Ph | |
| 7-118 | NO$_2$ | Et | Cl | —CO-Ph | |
| 7-119 | SO$_2$Me | Me | Cl | —CO-Ph | |
| 7-120 | SO$_2$Me | Et | Cl | —CO-Ph | |
| 7-121 | CH$_2$OMe | Me | Cl | —CO-Ph | |
| 7-122 | CH$_2$OMe | Et | Cl | —CO-Ph | |
| 7-123 | CH$_2$SO$_2$Me | Me | Cl | —CO-Ph | |
| 7-124 | CH$_2$SO$_2$Me | Et | Cl | —CO-Ph | |

TABLE 7-continued

Compounds of the formula (I) according to the invention in which $R^1$ and $R^2$ are each methyl.

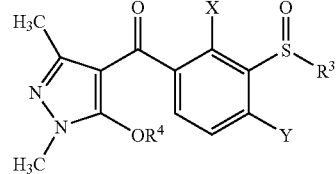

| No. | X | $R^3$ | Y | $R^4$ | Physical data: $^1$H-NMR: δ [CDCl$_3$] |
|---|---|---|---|---|---|
| 7-125 | CH$_2$OCH$_2$CH$_2$OMe | Me | Cl | —CO-Ph | |
| 7-126 | CH$_2$OCH$_2$CH$_2$OMe | Et | Cl | —CO-Ph | |
| 7-127 | Cl | Me | Br | —CO-Ph | |
| 7-128 | Cl | Et | Br | —CO-Ph | |
| 7-129 | Me | Me | Br | —CO-Ph | |
| 7-130 | Me | Et | Br | —CO-Ph | |
| 7-131 | CF$_3$ | Me | Br | —CO-Ph | |
| 7-132 | CF$_3$ | Et | Br | —CO-Ph | |
| 7-133 | OMe | Me | Br | —CO-Ph | |
| 7-134 | OMe | Et | Br | —CO-Ph | |
| 7-135 | NO$_2$ | Me | Br | —CO-Ph | |
| 7-136 | NO$_2$ | Et | Br | —CO-Ph | |
| 7-137 | SO$_2$Me | Me | Br | —CO-Ph | |
| 7-138 | SO$_2$Me | Et | Br | —CO-Ph | |
| 7-139 | CH$_2$OMe | Me | Br | —CO-Ph | |
| 7-140 | CH$_2$OMe | Et | Br | —CO-Ph | |
| 7-141 | CH$_2$SO$_2$Me | Me | Br | —CO-Ph | |
| 7-142 | CH$_2$SO$_2$Me | Et | Br | —CO-Ph | |
| 7-143 | CH$_2$OCH$_2$CH$_2$OMe | Me | Br | —CO-Ph | |
| 7-144 | CH$_2$OCH$_2$CH$_2$OMe | Et | Br | —CO-Ph | |
| 7-145 | Cl | Me | I | —CO-Ph | |
| 7-146 | Cl | Et | I | —CO-Ph | |
| 7-147 | Me | Me | I | —CO-Ph | |
| 7-148 | Me | Et | I | —CO-Ph | |
| 7-149 | CF$_3$ | Me | I | —CO-Ph | |
| 7-150 | CF$_3$ | Et | I | —CO-Ph | |
| 7-151 | OMe | Me | I | —CO-Ph | |
| 7-152 | OMe | Et | I | —CO-Ph | |
| 7-153 | NO$_2$ | Me | I | —CO-Ph | |
| 7-154 | NO$_2$ | Et | I | —CO-Ph | |
| 7-155 | SO$_2$Me | Me | I | —CO-Ph | |
| 7-156 | SO$_2$Me | Et | I | —CO-Ph | |
| 7-157 | CH$_2$OMe | Me | I | —CO-Ph | |
| 7-158 | CH$_2$OMe | Et | I | —CO-Ph | |
| 7-159 | CH$_2$SO$_2$Me | Me | I | —CO-Ph | |
| 7-160 | CH$_2$SO$_2$Me | Et | I | —CO-Ph | |
| 7-161 | CH$_2$OCH$_2$CH$_2$OMe | Me | I | —CO-Ph | |
| 7-162 | CH$_2$OCH$_2$CH$_2$OMe | Et | I | —CO-Ph | |
| 7-163 | Cl | Me | NO$_2$ | —CO-Ph | |
| 7-164 | Cl | Et | NO$_2$ | —CO-Ph | |
| 7-165 | Me | Me | NO$_2$ | —CO-Ph | |
| 7-166 | Me | Et | NO$_2$ | —CO-Ph | |
| 7-167 | CF$_3$ | Me | NO$_2$ | —CO-Ph | |
| 7-168 | CF$_3$ | Et | NO$_2$ | —CO-Ph | |
| 7-169 | OMe | Me | NO$_2$ | —CO-Ph | |
| 7-170 | OMe | Et | NO$_2$ | —CO-Ph | |
| 7-171 | NO$_2$ | Me | NO$_2$ | —CO-Ph | |
| 7-172 | NO$_2$ | Et | NO$_2$ | —CO-Ph | |
| 7-173 | SO$_2$Me | Me | NO$_2$ | —CO-Ph | |
| 7-174 | SO$_2$Me | Et | NO$_2$ | —CO-Ph | |
| 7-175 | CH$_2$OMe | Me | NO$_2$ | —CO-Ph | |
| 7-176 | CH$_2$OMe | Et | NO$_2$ | —CO-Ph | |
| 7-177 | CH$_2$SO$_2$Me | Me | NO$_2$ | —CO-Ph | |
| 7-178 | CH$_2$SO$_2$Me | Et | NO$_2$ | —CO-Ph | |
| 7-179 | CH$_2$OCH$_2$CH$_2$OMe | Me | NO$_2$ | —CO-Ph | |
| 7-180 | CH$_2$OCH$_2$CH$_2$OMe | Et | NO$_2$ | —CO-Ph | |
| 7-181 | Cl | Me | SO$_2$Me | —CH$_2$—CO-(4-Me-Ph) | |
| 7-182 | Cl | Et | SO$_2$Me | —CH$_2$—CO-(4-Me-Ph) | |
| 7-183 | Me | Me | SO$_2$Me | —CH$_2$—CO-(4-Me-Ph) | |

TABLE 7-continued

Compounds of the formula (I) according to the invention in which $R^1$ and $R^2$ are each methyl.

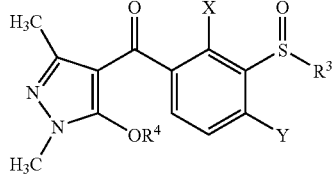

| No. | X | $R^3$ | Y | $R^4$ | Physical data: $^1$H-NMR: δ [CDCl$_3$] |
|---|---|---|---|---|---|
| 7-184 | Me | Et | SO$_2$Me | —CH$_2$—CO-(4-Me-Ph) | |
| 7-185 | CF$_3$ | Me | SO$_2$Me | —CH$_2$—CO-(4-Me-Ph) | |
| 7-186 | CF$_3$ | Et | SO$_2$Me | —CH$_2$—CO-(4-Me-Ph) | |
| 7-187 | OMe | Me | SO$_2$Me | —CH$_2$—CO-(4-Me-Ph) | |
| 7-188 | OMe | Et | SO$_2$Me | —CH$_2$—CO-(4-Me-Ph) | |
| 7-189 | NO$_2$ | Me | SO$_2$Me | —CH$_2$—CO-(4-Me-Ph) | |
| 7-190 | NO$_2$ | Et | SO$_2$Me | —CH$_2$—CO-(4-Me-Ph) | |
| 7-191 | SO$_2$Me | Me | SO$_2$Me | —CH$_2$—CO-(4-Me-Ph) | |
| 7-192 | SO$_2$Me | Et | SO$_2$Me | —CH$_2$—CO-(4-Me-Ph) | |
| 7-193 | CH$_2$OMe | Me | SO$_2$Me | —CH$_2$—CO-(4-Me-Ph) | |
| 7-194 | CH$_2$OMe | Et | SO$_2$Me | —CH$_2$—CO-(4-Me-Ph) | |
| 7-195 | CH$_2$SO$_2$Me | Me | SO$_2$Me | —CH$_2$—CO-(4-Me-Ph) | |
| 7-196 | CH$_2$SO$_2$Me | Et | SO$_2$Me | —CH$_2$—CO-(4-Me-Ph) | |
| 7-197 | CH$_2$OCH$_2$CH$_2$OMe | Me | SO$_2$Me | —CH$_2$—CO-(4-Me-Ph) | |
| 7-198 | CH$_2$OCH$_2$CH$_2$OMe | Et | SO$_2$Me | —CH$_2$—CO-(4-Me-Ph) | |
| 7-199 | Cl | Me | Cl | —CH$_2$—CO-(4-Me-Ph) | |
| 7-200 | Cl | Et | Cl | —CH$_2$—CO-(4-Me-Ph) | |
| 7-201 | Me | Me | Cl | —CH$_2$—CO-(4-Me-Ph) | |
| 7-202 | Me | Et | Cl | —CH$_2$—CO-(4-Me-Ph) | |
| 7-203 | CF$_3$ | Me | Cl | —CH$_2$—CO-(4-Me-Ph) | |
| 7-204 | CF$_3$ | Et | Cl | —CH$_2$—CO-(4-Me-Ph) | |
| 7-205 | OMe | Me | Cl | —CH$_2$—CO-(4-Me-Ph) | |
| 7-206 | OMe | Et | Cl | —CH$_2$—CO-(4-Me-Ph) | |
| 7-207 | NO$_2$ | Me | Cl | —CH$_2$—CO-(4-Me-Ph) | |
| 7-208 | NO$_2$ | Et | Cl | —CH$_2$—CO-(4-Me-Ph) | |
| 7-209 | SO$_2$Me | Me | Cl | —CH$_2$—CO-(4-Me-Ph) | |
| 7-210 | SO$_2$Me | Et | Cl | —CH$_2$—CO-(4-Me-Ph) | |
| 7-211 | CH$_2$OMe | Me | Cl | —CH$_2$—CO-(4-Me-Ph) | |
| 7-212 | CH$_2$OMe | Et | Cl | —CH$_2$—CO-(4-Me-Ph) | |
| 7-213 | CH$_2$SO$_2$Me | Me | Cl | —CH$_2$—CO-(4-Me-Ph) | |
| 7-214 | CH$_2$SO$_2$Me | Et | Cl | —CH$_2$—CO-(4-Me-Ph) | |
| 7-215 | CH$_2$OCH$_2$CH$_2$OMe | Me | Cl | —CH$_2$—CO-(4-Me-Ph) | |
| 7-216 | CH$_2$OCH$_2$CH$_2$OMe | Et | Cl | —CH$_2$—CO-(4-Me-Ph) | |
| 7-217 | Cl | Me | Br | —CH$_2$—CO-(4-Me-Ph) | |
| 7-218 | Cl | Et | Br | —CH$_2$—CO-(4-Me-Ph) | |
| 7-219 | Me | Me | Br | —CH$_2$—CO-(4-Me-Ph) | |
| 7-220 | Me | Et | Br | —CH$_2$—CO-(4-Me-Ph) | |
| 7-221 | CF$_3$ | Me | Br | —CH$_2$—CO-(4-Me-Ph) | |
| 7-222 | CF$_3$ | Et | Br | —CH$_2$—CO-(4-Me-Ph) | |
| 7-223 | OMe | Me | Br | —CH$_2$—CO-(4-Me-Ph) | |
| 7-224 | OMe | Et | Br | —CH$_2$—CO-(4-Me-Ph) | |
| 7-225 | NO$_2$ | Me | Br | —CH$_2$—CO-(4-Me-Ph) | |
| 7-226 | NO$_2$ | Et | Br | —CH$_2$—CO-(4-Me-Ph) | |
| 7-227 | SO$_2$Me | Me | Br | —CH$_2$—CO-(4-Me-Ph) | |
| 7-228 | SO$_2$Me | Et | Br | —CH$_2$—CO-(4-Me-Ph) | |
| 7-229 | CH$_2$OMe | Me | Br | —CH$_2$—CO-(4-Me-Ph) | |
| 7-230 | CH$_2$OMe | Et | Br | —CH$_2$—CO-(4-Me-Ph) | |
| 7-231 | CH$_2$SO$_2$Me | Me | Br | —CH$_2$—CO-(4-Me-Ph) | |
| 7-232 | CH$_2$SO$_2$Me | Et | Br | —CH$_2$—CO-(4-Me-Ph) | |
| 7-233 | CH$_2$OCH$_2$CH$_2$OMe | Me | Br | —CH$_2$—CO-(4-Me-Ph) | |
| 7-234 | CH$_2$OCH$_2$CH$_2$OMe | Et | Br | —CH$_2$—CO-(4-Me-Ph) | |
| 7-235 | Cl | Me | I | —CH$_2$—CO-(4-Me-Ph) | |
| 7-236 | Cl | Et | I | —CH$_2$—CO-(4-Me-Ph) | |
| 7-237 | Me | Me | I | —CH$_2$—CO-(4-Me-Ph) | |
| 7-238 | Me | Et | I | —CH$_2$—CO-(4-Me-Ph) | |
| 7-239 | CF$_3$ | Me | I | —CH$_2$—CO-(4-Me-Ph) | |
| 7-240 | CF$_3$ | Et | I | —CH$_2$—CO-(4-Me-Ph) | |
| 7-241 | OMe | Me | I | —CH$_2$—CO-(4-Me-Ph) | |
| 7-242 | OMe | Et | I | —CH$_2$—CO-(4-Me-Ph) | |
| 7-243 | NO$_2$ | Me | I | —CH$_2$—CO-(4-Me-Ph) | |
| 7-244 | NO$_2$ | Et | I | —CH$_2$—CO-(4-Me-Ph) | |
| 7-245 | SO$_2$Me | Me | I | —CH$_2$—CO-(4-Me-Ph) | |

TABLE 7-continued

Compounds of the formula (I) according to the invention in which R¹ and R² are each methyl.

Structure: 3-methyl-1-methyl-pyrazole with C(=O) at position 4 connected to a phenyl ring bearing OR⁴ (ortho to carbonyl), X (ortho to S(=O)R³), S(=O)R³ and Y substituents.

| No. | X | R³ | Y | R⁴ | Physical data: ¹H-NMR: δ [CDCl₃] |
|---|---|---|---|---|---|
| 7-246 | SO₂Me | Et | I | —CH₂—CO-(4-Me-Ph) | |
| 7-247 | CH₂OMe | Me | I | —CH₂—CO-(4-Me-Ph) | |
| 7-248 | CH₂OMe | Et | I | —CH₂—CO-(4-Me-Ph) | |
| 7-249 | CH₂SO₂Me | Me | I | —CH₂—CO-(4-Me-Ph) | |
| 7-250 | CH₂SO₂Me | Et | I | —CH₂—CO-(4-Me-Ph) | |
| 7-251 | CH₂OCH₂CH₂OMe | Me | I | —CH₂—CO-(4-Me-Ph) | |
| 7-252 | CH₂OCH₂CH₂OMe | Et | I | —CH₂—CO-(4-Me-Ph) | |
| 7-253 | Cl | Me | NO₂ | —CH₂—CO-(4-Me-Ph) | |
| 7-254 | Cl | Et | NO₂ | —CH₂—CO-(4-Me-Ph) | |
| 7-255 | Me | Me | NO₂ | —CH₂—CO-(4-Me-Ph) | |
| 7-256 | Me | Et | NO₂ | —CH₂—CO-(4-Me-Ph) | |
| 7-257 | CF₃ | Me | NO₂ | —CH₂—CO-(4-Me-Ph) | |
| 7-258 | CF₃ | Et | NO₂ | —CH₂—CO-(4-Me-Ph) | |
| 7-259 | OMe | Me | NO₂ | —CH₂—CO-(4-Me-Ph) | |
| 7-260 | OMe | Et | NO₂ | —CH₂—CO-(4-Me-Ph) | |
| 7-261 | NO₂ | Me | NO₂ | —CH₂—CO-(4-Me-Ph) | |
| 7-262 | NO₂ | Et | NO₂ | —CH₂—CO-(4-Me-Ph) | |
| 7-263 | SO₂Me | Me | NO₂ | —CH₂—CO-(4-Me-Ph) | |
| 7-264 | SO₂Me | Et | NO₂ | —CH₂—CO-(4-Me-Ph) | |
| 7-265 | CH₂OMe | Me | NO₂ | —CH₂—CO-(4-Me-Ph) | |
| 7-266 | CH₂OMe | Et | NO₂ | —CH₂—CO-(4-Me-Ph) | |
| 7-267 | CH₂SO₂Me | Me | NO₂ | —CH₂—CO-(4-Me-Ph) | |
| 7-268 | CH₂SO₂Me | Et | NO₂ | —CH₂—CO-(4-Me-Ph) | |
| 7-269 | CH₂OCH₂CH₂OMe | Me | NO₂ | —CH₂—CO-(4-Me-Ph) | |
| 7-270 | CH₂OCH₂CH₂OMe | Et | NO₂ | —CH₂—CO-(4-Me-Ph) | |

B. FORMULATION EXAMPLES a) A dust is obtained by mixing 10 parts by weight of a compound of the formula (I) and/or its salts and 90 parts by weight of talc as inert substance and comminuting the mixture in a hammer mill.

b) A wettable powder which is readily dispersible in water is obtained by mixing 25 parts by weight of a compound of the formula (I) and/or its salts, 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (I) and/or its salts with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 up to over 277° C.) and grinding the mixture in a bowl mill to a fineness of below 5 microns.

d) An emulsifiable concentrate is obtained from 15 parts by weight of a compound of the formula (I) and/or its salts, 75 parts by weight of cyclohexanone as solvent and 10 parts by weight of oxyethylated nonylphenol as emulsifier.

e) Water-dispersible granules are obtained by mixing
  75 parts by weight of a compound of the formula (I) and/or its salts,
  10 parts by weight of calcium lignosulfonate,
  5 parts by weight of sodium lauryl sulfate,
  3 parts by weight of polyvinyl alcohol and
  7 parts by weight of kaolin,
  grinding the mixture in a pinned-disk mill and granulating the powder in a fluidized bed by spraying on water as granulation liquid.

f) Water-dispersible granules are also obtained by homogenizing and precomminuting, in a colloid mill,
  25 parts by weight of a compound of the formula (I) and/or its salts,
  5 parts by weight of sodium 2,2'-dinaphthylmethane-6,6'-disulfonate,
  2 parts by weight of sodium oleoylmethyltaurinate,
  1 part by weight of polyvinyl alcohol,
  17 parts by weight of calcium carbonate and
  50 parts by weight of water,
  subsequently grinding the mixture in a bead mill, and atomizing and drying the resulting suspension in a spray tower by means of a single-substance nozzle.

C. BIOLOGICAL EXAMPLES

1. Herbicidal Pre-Emergence Effect Against Harmful Plants

Seeds of monocotyledonous or dicotyledonous weeds or crop plants are placed in sandy loam soil in wood-fiber pots and covered with soil. The compounds according to the invention, formulated in the form of wettable powders (WP) or emulsion concentrates (EC), are then applied to the surface of the soil cover in the form of an aqueous suspension or emulsion at a water application rate of 600 to 800 l/ha (converted), with addition of 0.2% wetter. After the treatment, the pots are placed in the greenhouse and kept under good growth conditions for the test plants. The damage to the test plants is scored visually in comparison with untreated controls after an experimental time of 3 weeks has elapsed (herbicidal activity in percent (%): 100% activity=plants have died, 0% activity=like control plants). Here, for example the compounds Nos. 1-2, 2-9, 2-10, 2-11 and 3-238 show, at an application rate of 80 g/ha, each at least 90% strength activity against *Amaranthus retroflexus* and *Veronica Persica*.

The compounds Nos. 1-237, 1-238, 2-9, 2-10, 2-237 and 2-238 show, at an application rate of 80 g/ha, each at least 90% strength activity against *Abutilon theophrasti, Amaranthus retroflexus* and *Echinochloa crus galli*. The compounds Nos. 1-10, 2-9 and 2-238 show, at an application rate of 80 g/ha, each at least 90% strength activity against *Abutilon theophrasti* and *Matricaria inodora*.

2. Herbicidal Post-Emergence Activity Against Harmful Plants

Seeds of monocotyledonous or dicotyledonous weeds or crop plants are placed in sandy loam soil in wood-fiber pots, covered with soil and grown in the greenhouse under good growth conditions. 2 to 3 weeks after sowing, the test plants are treated in the one-leaf stage. The compounds according to the invention, formulated in the form of wettable powders (WP) or emulsion concentrates (EC), are then sprayed onto the green plant parts in the form of an aqueous suspension or emulsion at a water application rate of 600 to 800 l/ha (converted), with addition of 0.2% wetter. After the test plants have been left to stand under optimal growth conditions in the greenhouse for approximately 3 weeks, the activity of the preparations is scored visually in comparison with untreated controls (herbicidal activity in percent (%): 100% activity=plants have died, 0% activity=like control plants).

Here, for example the compounds Nos. 1-10, 1-237 and 2-9 show, at an application rate of 80 g/ha, each at least 90% strength activity against *Stellaria media* and *Veronica Persica*. The compounds Nos. 1-238, 2-10 and 2-238 show, at an application rate of 80 g/ha, each at least 90% strength activity against *Setaria viridis* and *Viola tricolor*. The compounds Nos. 1-2, 1-237, 1-238 and 2-11 show, at an application rate of 80 g/ha, each at least 90% strength activity against *Abutilon theophrasti* and *Echinochloa crus galli*.

The invention claimed is:

1. A 4-(3-alkylsulfinylbenzoyl)pyrazole of the formula (I) or a salt thereof

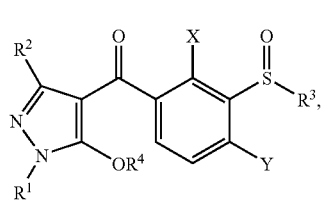

(I)

in which
$R^1$ is $(C_1-C_4)$-alkyl,
$R^2$ is hydrogen or $(C_1-C_4)$-alkyl,
$R^3$ is $(C_1-C_6)$-alkyl,
$R^4$ is hydrogen, $(C_1-C_6)$-alkylsulfonyl, $(C_1-C_4)$-alkoxy-$(C_1-C_6)$-alkylsulfonyl, or is phenylsulfonyl, thiophenyl-2-sulfonyl, benzoyl, benzoyl-$(C_1-C_6)$-alkyl or benzyl, each of which is substituted by m identical or different radicals from the group consisting of halogen, $(C_1-C_4)$-alkyl and $(C_1-C_4)$-alkoxy,
X is hydrogen, mercapto, nitro, halogen, cyano, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^5$, $OCOR^5$, $OSO_2R^5$, $S(O)_nR^5$, $SO_2OR^5$, $SO_2N(R^5)_2$, $NR^5SO_2R^5$, $NR^5COR^5$, $(C_1-C_6)$-alkyl-$S(O)_nR^5$, $(C_1-C_6)$-alkyl-$OR^5$, $(C_1-C_6)$-alkyl-$OCOR^5$, $(C_1-C_6)$-alkyl-$OSO_2R^5$, $(C_1-C_6)$-alkyl-$SO_2OR^5$, $(C_1-C_6)$-alkyl-$SO_2N(R^5)_2$ or $(C_1-C_6)$-alkyl-$NR^5COR^5$;
Y is fluorine, chlorine, bromine, iodine, nitro or the group $SO_2R^7$,
$R^5$ is hydrogen, $(C_1-C_6)$-alkyl, $(C_2-C_6)$-alkenyl, $(C_2-C_6)$-alkynyl, $(C_3-C_6)$-cycloalkyl, phenyl or phenyl-$(C_1-C_6)$-alkyl, where the six last-mentioned radicals are substituted by s radicals from the group consisting of hydroxy, mercapto, amino, cyano, nitro, thiocyanato, $OR^6$, $SR^6$, $N(R^6)_2$, $NOR^6$, $OCOR^6$, $SCOR^6$, $NR^6COR^6$, $CO_2R^6$, $COSR^6$, $CON(R^6)_2$, $(C_1)$-$C_4$-alkyliminooxy, $(C_1-C_4)$-alkylcarbonyl, $(C_1-C_4)$-alkoxy-$(C_2-C_6)$-alkoxycarbonyl and $(C_1-C_4)$-alkylsulfonyl;
$R^6$ is hydrogen, $(C_1-C_6)$-alkyl, $(C_2-C_6)$-alkenyl or $(C_2-C_6)$-alkynyl,
$R^7$ is $(C_1-C_4)$-alkyl,
m is 0, 1, 2, 3, 4 or 5,
n is 0, 1 or 2,
s is 0, 1, 2 or 3.

2. The 4-(3-alkylsulfinylbenzoyl)pyrazole as claimed in claim 1 in which
$R^1$ is methyl, ethyl, n-propyl or isopropyl,
$R^2$ is hydrogen, methyl, ethyl, n-propyl or isopropyl,
$R^3$ is $(C_1-C_4)$-alkyl,
$R^4$ is hydrogen, $(C_1-C_3)$-alkylsulfonyl, $(C_1-C_2)$-alkoxy-$(C_1-C_4)$-alkylsulfonyl, or is phenylsulfonyl, thiophenyl-2-sulfonyl, benzoyl, benzoyl-$(C_1-C_6)$-alkyl or benzyl, each of which is substituted by m methyl groups,
X is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl,
Y is fluorine, chlorine, bromine, iodine or the group $SO_2R^7$,
$R^7$ is methyl, ethyl, n-propyl or isopropyl,
m is 0, 1, 2 or 3.

3. The 4-(3-alkylsulfinylbenzoyl)pyrazole as claimed in claim 1 in which
$R^1$ is methyl or ethyl,
$R^2$ is hydrogen, methyl or ethyl,
$R^3$ is methyl, ethyl, n-propyl or isopropyl,
$R^4$ is hydrogen,
X is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl,
Y is fluorine, chlorine, bromine, iodine or the group $SO_2R^7$,
$R^7$ is methyl or ethyl.

4. A herbicidal composition which comprises a herbicidally active amount of at least one compound of the formula (I) as claimed in claim 1.

5. The herbicidal composition as claimed in claim 4 in a mixture with formulation auxiliaries.

6. A method of controlling unwanted plants, which comprises applying an effective amount of at least one compound of the formula (I) as claimed in claim 1 to plants and/or to a location of unwanted plant growth.

7. A compound of the formula (I) as claimed in claim 1 capable of controlling unwanted plants.

8. A method for using a compound as claimed in claim 7, wherein a compound of the formula (I) is employed for controlling unwanted plants in crops of useful plants.

9. A method as claimed in claim 8, wherein the useful plants are transgenic useful plants.

10. A method for making a herbicidically active 4-(3-alkylsulfinylbenzol) pyrazole as claimed in claim 1 comprising reacting a compound of formula (II),

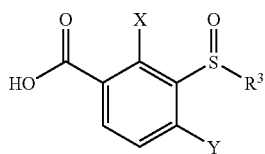

with a pyrazole,
in which
$R^3$ is $(C_1-C_6)$-alkyl
X is hydrogen, mercapto, nitro, halogen, cyano, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$alkynyl, $(C_3-C_6)$-haloalkynyl, $(C_3-C_6)$ cycloalkyl, $OR^5$, $OCOR^5$, $OSO_2R^5$, $S(O)_nR^5$, $SO_2OR^5$, $SO_2N(R^5)_2$, $NR^5SO_2R^5$, $NR^5COR^5$, $(C_1-C_6)$-alkyl-$S(O)_nR^5$, $(C_1-C_6)$-alkyl-$OR^5$, $(C_1-C_6)$-alkyl-$OCOR^5$, $(C_1-C_6)$-alkyl-$OSO2R^5$, $(C_1-C6)$-alkyl-$SO_2OR^5$, $(C_1-C_6)$-alkyl-$SO_2N(R^5)_2$ or $(C_1-C_6)$-alkyl-$NR^5COR^5$;
Y is fluorine, chlorine, bromine, iodine, nitro or the group $SO_2R^7$.

11. A compound of formula (Ia) or a salt thereof

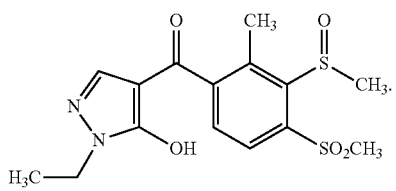

12. A herbicidal composition, comprising a herbicidally active amount of at least one compound of formula (Ia) or salt as claimed in claim 11.

13. The herbicidal composition as claimed in claim 12 in a mixture with formulation auxillaries.

14. A method of controlling undesired plants, comprising applying an effective amount of at least one compound of the formula (Ia) as claimed in claim 11 to plants and/or to a location of unwanted plant growth.

15. The 4-(3-alkylsulfinylbenzoyl)pyrazole as claimed in claim 1 in which
$R^1$ is methyl or ethyl,
$R^2$ is hydrogen,
$R^3$ is methyl, ethyl, n-propyl or isopropyl,
$R^4$ is hydrogen,
X is methyl, chlorine, or methoxymethyl,
Y is chlorine, bromine, or the group $SO_2R^7$,
$R^7$ is methyl.

16. The 4-(3-alkylsulfinylbenzoyl)pyrazole as claimed in claim 1 in which
$R^2$ is $(C_1-C_4)$-alkyl.

17. The 4-(3-alkylsulfinylbenzoyl)pyrazole as claimed in claim 1 in which
$R^4$ is $(C_1-C_6)$-alkylsulfonyl, $(C_1-C_4)$-alkoxy-$(C_1-C_6)$-alkylsulfonyl, or is phenylsulfonyl, thiophenyl-2-sulfonyl, benzoyl, benzoyl-$(C_1-C_6)$-alkyl or benzyl, each of which is substituted by m identical or different radicals from the group consisting of halogen, $(C_1-C_4)$-alkyl and $(C_1-C_4)$-alkoxy.

18. The 4-(3-alkylsulfinylbenzoyl)pyrazole as claimed in claim 1 in which
X is hydrogen, mercapto, nitro, fluorine, bromine, iodine, cyano, thiocyanato, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^5$, $OCOR^5$, $OSO_2R^5$, $S(O)_nR^5$, $SO_2OR^5$, $SO_2N(R^5)_2$, $NR^5SO_2R^5$, $NR^5COR^5$, $(C_1-C_6)$-alkyl-$S(O)_nR^5$, $(C_1-C_6)$-alkyl-$OR^5$, $(C_1-C_6)$-alkyl-$OCOR^5$, $(C_1-C_6)$-alkyl-$OSO2R^5$, $(C_1-C_6)$-alkyl-$SO_2OR^5$, $(C_1-C_6)$-alkyl-$SO_2N(R^5)_2$ or $(C_1-C_6)$-alkyl-$NR^5COR^5$.

19. The 4-(3-alkylsulfinylbenzoyl)pyrazole as claimed in claim 1 in which
Y is fluorine, chlorine, bromine, iodine, or nitro.

* * * * *